United States Patent
Godbout et al.

(10) Patent No.: US 12,240,828 B2
(45) Date of Patent: *Mar. 4, 2025

(54) HETEROAROMATIC COMPOUNDS AS VANIN INHIBITORS

(71) Applicant: Boehringer Ingelheim International GmbH, Ingelheim am Rhein (DE)

(72) Inventors: Cedrickx Godbout, Attenweiler (DE); Martin Thomas Fleck, Munich (DE); Hannes Fiepko Koolman, Biberach an der Riss (DE); Thomas Martin Kirrane, Jr., San Ramon, CA (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 711 days.

This patent is subject to a terminal disclaimer.

(21) Appl. No.: 17/299,148

(22) PCT Filed: Dec. 2, 2019

(86) PCT No.: PCT/EP2019/083259
§ 371 (c)(1),
(2) Date: Jun. 2, 2021

(87) PCT Pub. No.: WO2020/114947
PCT Pub. Date: Jun. 11, 2020

(65) Prior Publication Data
US 2022/0048889 A1    Feb. 17, 2022

Related U.S. Application Data

(60) Provisional application No. 62/774,412, filed on Dec. 3, 2018.

(51) Int. Cl.
| C07D 401/14 | (2006.01) |
| A61K 45/06  | (2006.01) |
| C07D 401/06 | (2006.01) |
| C07D 413/14 | (2006.01) |

(52) U.S. Cl.
CPC ........... *C07D 401/14* (2013.01); *A61K 45/06* (2013.01); *C07D 401/06* (2013.01); *C07D 413/14* (2013.01)

(58) Field of Classification Search
CPC .......... A61P 1/00; A61P 35/00; C07D 401/14; C07D 401/06; C07D 413/14
See application file for complete search history.

(56) References Cited

U.S. PATENT DOCUMENTS

| 9,585,891 B2 | 3/2017 | Muzerelle et al. |
| 10,308,615 B2 | 6/2019 | Casimiro-Garcia et al. |
| 10,364,255 B2 | 7/2019 | Bosanac et al. |
| 11,078,182 B2 * | 8/2021 | Fleck .................. C07D 401/14 |
| 2003/0195192 A1 | 10/2003 | Haviv et al. |
| 2015/0250792 A1 | 9/2015 | Muzerelle et al. |
| 2018/0148420 A1 | 5/2018 | Casimiro-Garcia et al. |
| 2018/0354968 A1 | 12/2018 | Bosanac et al. |
| 2019/0263828 A1 | 8/2019 | Bosanac et al. |
| 2020/0069663 A1 | 3/2020 | Godbout et al. |
| 2020/0172508 A1 | 6/2020 | Fleck et al. |
| 2023/0295112 A1 * | 9/2023 | Fleck ..................... A61P 17/00 |
| | | 514/343 |

FOREIGN PATENT DOCUMENTS

| WO | 2005035524 A1 | 4/2005 | |
| WO | 2014048547 A1 | 4/2014 | |
| WO | WO-2016193844 A1 * | 12/2016 | ........... A61K 31/505 |
| WO | WO-2018011681 A1 * | 1/2018 | ........... A61K 31/506 |
| WO | 2018228934 A1 | 12/2018 | |

OTHER PUBLICATIONS

Barluenga, Jose et al. "Arylation of a-Chiral Ketones by Palladium-Catalyzed Cross-Coupling Reactions of Tosylhydrazones with Aryl Halides**" (2010) Angew. Chem. Int. Ed., 49, 6856-6859.
Berge, Stephen M. et al. "Journal of Pharmaceutical Salts" Jan. 1977, vol. 66, No. 1, 1-19.
Berruyer, C. et al. "Vanin-1 -/- Mice Exhibit a Glutathione-Mediated Tissue Resistance to Oxidative Stress" (2004) Molecular and Cellular Biology, vol. 24, No. 16, 7214-7224.
Berruyer, Carole et al. "Vanin-1 licenses inflammatory mediator production by gut epithelial cells and controls colitis by antagonizing peroxisome proliferator-activated receptor y activity" (2006) The Journal of Experimental Medicine, vol. 203, No. 13, 2817-2827.
CAS Registry No. 2128587-10-8, Sep. 19, 2017, 1 pg.
CAS Registry No. 2175416-99-4, Feb. 18, 2018, 1 pg.
Chai, Chi-Young et al. "VNN1 overexpression is associated with poor response to preoperative chemoradiotherapy and adverse prognosis in patients with rectal cancers" (2016) Am J Transl Res, 8(10): 4455-4463.

(Continued)

*Primary Examiner* — Eric Olson
*Assistant Examiner* — Samuel L Galster
(74) *Attorney, Agent, or Firm* — David L. Kershner

(57) ABSTRACT

The present invention encompasses compounds of the formula I

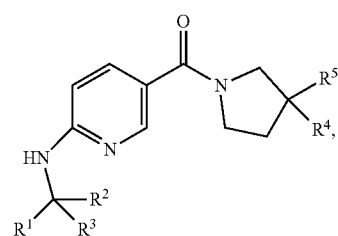

which are suitable for the treatment of diseases related to Vanin, and processes for making these compounds, pharmaceutical preparations containing these compounds, and their methods of use.

11 Claims, No Drawings

(56) References Cited

OTHER PUBLICATIONS

Gensollen, Thomas et al. "Functional Polymorphisms in the Regulatory Regions of the VNN1 Gene are associated with Susceptibility to Inflammatory Bowel Diseases" (2013) Inflammatory Bowel Diseases, vol. 19, No. 11, 2315-2325.
International Search Report PCT/EP2018/065140 mailed Jul. 31, 2018.
International Search Report PCT/EP2019/072699 mailed on Nov. 12, 2019.
International Search Report PCT/EP2019/083252 mailed Feb. 17, 2020.
Jansen, Patrick A.M. et al. "Expression of the Vanin Gene Family in Normal and Inflamed Human Skin: Induction by Proinflammatory Cytokines" (2009) The Journal of Investigative Dermatology, vol. 129, No. 9, 2167-2174.
Kang, Muxing et al. "VNN1, a potential biomarker for pancreatic cancer-associated new-onset diabetes, aggravates paraneoplastic islet dysfunction by increasing oxidative stress" (2016) Cancer Letters, 373, 241-250.
Kavian, Niloufar et al. "Imbalance of the Vanin-1 Pathway in Systemic Sclerosis" (2016) The Journal of Immunology, vol. 197, 3326-3335.
Khor, Bernard et al. "Genetics and pathogenesis of inflammatory bowel disease" (2011) Nature, vol. 474, 307-317.
Lipinski, Boguslaw "Pathophysiology of oxidative stress in diabetes mellitus" (2001) Journal of Diabetes and its Complications, vol. 15, 203-210.
Martin, Florent et al. "Vanin genes are clustered (human 6q22-24 and mouse 10A2B1) and encode isoforms of pantetheinase ectoenzymes" (2001) Immunogenetics, 53: 296-306.
Martin, Florent et al. "Vanin-1 -/- mice show decreased NSAID- and Schistosoma-induced intestinal inflammation assoicated with higher glutathione stores" (2004) The Journal of Clinical Investigation, vol. 113, No. 4, 591-597.
Naquet, Philippe et al. "Role of the Vnn1 pantetheinase in tissue tolerance to stress" (2014) Biochemical Society Transactions, vol. 42, part 4, 1094-1100.
Pouyet, Laurent et al. "Epithelial vanin-1 controls inflammation-driven carcinogenesis in the colitis-associated colon cancer model" (2010) Inflammatory Bowel Diseases, vol. 16, No. 1, 96-104.
Sosa, Venus et al. "Oxidative stress and cancer: An overview" (2013) Ageing Research Reviews, vol. 12, 376-390.
Zhang, Bing et al. "The role of vanin-1 and oxidative stress-related pathways in distinguishing acute and chronic pediatric ITP" (2011) Blood, vol. 117, No. 17, 4569-4579.

* cited by examiner

HETEROAROMATIC COMPOUNDS AS VANIN INHIBITORS

BACKGROUND OF THE INVENTION

1. Technical Field

The present invention relates to novel compounds which inhibit Vanin, pharmaceutical compositions containing the same and their use as medicaments.

2. Background Information

Isoforms 1 and 2 of Vanin enzymes are single-domain extracellular pantetheinases that catalyze the cleavage of pantethine and pantetheine into pantothenic acid and cystamine and cysteamine, respectively (Martin, Immunogenetics, (2001 May-June) Vol. 53, No. 4, pp. 296-306). Generation of cysteamine has been linked to increased oxidative in tissue stress resulting from decreased glutathione levels, a condition characteristic of many pathological conditions, including IBD (Xavier, Nature. 2011 Jun. 15; 474 (7351): 307-17), cancer (Sosa, Ageing research reviews, (2013 January) Vol. 12, No. 1, pp. 376-90) and diabetes (Lipinski, Journal of diabetes and its complications, (2001 July-August) Vol. 15, No. 4, pp. 203-10).

Increased Vanin-1 activity in the gut epithelium has been implicated in promoting tissue damage and inflammation by reducing resistance to oxidative stress in murine models (Naquet, Biochem Soc Trans. 2014 August; 42(4):1094-100); (Berruyer, Molecular and cellular biology, (2004 August) Vol. 24, No. 16, pp. 7214-24); (Berruyer, The Journal of experimental medicine, (2006 Dec. 25) Vol. 203, No. 13, pp. 2817-27); (Pouyet, Inflammatory bowel diseases, (2010 January) Vol. 16, No. 1, pp. 96-104). Homozygous VNN1 knock-out (KO) mice lack appreciable levels of cysteamine in blood and tissues and show glutathione-mediated tissue resistance to oxidative stress (Berruyer, The Journal of experimental medicine, (2006 Dec. 25) Vol. 203, No. 13, pp. 2817-27). In addition, these mice are protected from intestinal injury in TNBS, DSS and Schistosoma-induced colitis models (Berruyer, The Journal of experimental medicine, (2006 Dec. 25) Vol. 203, No. 13, pp. 2817-27; Pouyet, Inflammatory bowel diseases, (2010 January) Vol. 16, No. 1, pp. 96-104; Martin, The Journal of clinical investigation, (2004 February) Vol. 113, No. 4, pp. 591-7). Given rodents lack Vanin-2, their only source of cysteamine is from Vanin-1, therefore the protective phenotype of the VNN1 KO mouse is attributed to the lack of cysteamine.

In humans, Vanin-1 was observed to be upregulated in intestinal epithelium in tissue biopsies from UC and CD patients and a functional polymorphism in the regulatory region of the VNN1 gene which led to increased VNN1 expression was associated with increased IBD susceptibility (P=0.0003 heterozygous vs. wild-type) (Gensollen, Inflammatory bowel diseases, (2013 October) Vol. 19, No. 11, pp. 2315-25).

In addition, upregulation of Vanin-1 activity in the skin and blood has been linked to development and severity of fibrosis in Systemic Sclerosis patients (Kavian, Journal of immunology (Baltimore, Md.: 1950), (20161015) Vol. 197, No. 8, pp. 3326-3335), and elevated levels of Vanin-1 have been observed in chronic Juvenile Idiopathic Thrombocytopenia (Zhang, Blood, (2011 Apr. 28) Vol. 117, No. 17, pp. 4569-79), Psoriasis and Atopic Dermatitis (Jansen, The Journal of investigative dermatology, (2009 September) Vol. 129, No. 9, pp. 2167-74).

Elevated Vanin-1 expression and activity are also present and serve as biomarkers for pancreatic cancer associated new-onset diabetes (Kang, Cancer Letters (New York, NY., United States) (2016), 373(2), 241-250) and are also correlated with poor prognosis and response to treatment in colorectal cancer (Chai, American journal of translational research, (2016) Vol. 8, No. 10, pp. 4455-4463).

WO2018011681 and WO2016193844 disclose Vanin inhibitors for the treatment of a series of diseases e.g. Crohn's disease and ulcerative colitis.

The problem to be solved by the present invention is to provide novel compounds which act as inhibitors of Vanin enzymes, preferably as inhibitors of the Vanin-1 enzyme. It has been surprisingly found that the compounds of the present invention have potent Vanin-1 inhibitors activity, preferably exhibiting an inhibition of VNN-1 $IC_{50}$ [nM]<100, more preferred $IC_{50}$ [nM]<10, particularly preferred $IC_{50}$ [nM]<1.

Drugs with long residence times in the body are preferred because they remain effective for a longer period of time and therefore can be used in lower doses. Surprisingly the compounds of the present invention indicate favorable mean residence times (MRT).

Moreover the compounds of the present invention exhibit further capacities, which are favorable for their pharmacokinetic and pharmacological profile, e.g. good solubility and good metabolic stability.

DETAILED DESCRIPTION OF THE INVENTION

It has surprisingly been found that the problem mentioned above is solved by compounds of formula I of the present invention.

The present invention therefore relates to a compound of formula I, or a pharmaceutically acceptable salt thereof,

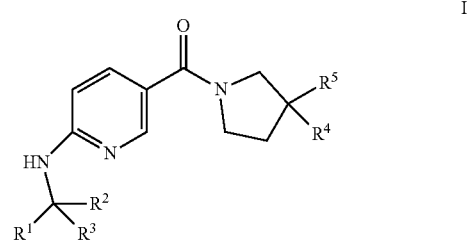

I wherein $R^1$ is selected from the group consisting of H, phenyl substituted by $R^{1.1}$ and $R^{1.3}$, 5-6 membered heteroaryl containing 1 to 3 heteroatoms selected from the group consisting of S, N and O substituted by $R^{1.2}$ and $R^{1.5}$, 5-6 membered heterocyclyl containing 1 or 2 heteroatoms selected from the group consisting of S, N and O substituted by $R^{1.4}$;

Wherein $R^{1.1}$ is selected from the group consisting of H, —CN, Br, Cl, F, $C_{3-5}$-cycloalkyl, 5 membered heteroaryl optionally substituted by $C_{1-3}$-alkyl, $CF_3$, $F_3C$—$CH_2$, $HF_2C$— $H_2N$—$S(O)_2$—, $H_3C$—NH— $S(O)_2$—, $(H_3C)_2N$—$S(O)_2$—, $H_3C$—NH—CO—, $C_{1-4}$-alkyl-O—, $H_3C$—O—CO—, $H_2N$—, $(H_3C)_2$N—, $H_2N$—CO— and $H_3C$—CO—NH—;

$R^{1.2}$ is selected from the group consisting of H, —CN, Br, Cl, F, $C_{3-5}$-cycloalkyl $CF_3$, $F_3C$—$CH_2$, $HF_2C$— $H_2N$—

$S(O)_2$—, $H_3C$—NH—$S(O)_2$—, $(H_3C)_2N$—$S(O)_2$—, $H_3C$—NH—CO—, $C_{1-4}$-alkyl-O—, $H_3C$—O—CO—. $H_2N$—, $(H_3C)_2N$—, $H_2N$—CO— and $H_3C$—CO—NH—;

wherein in the definition of $R^{1.1}$ and $R^{1.2}$ mentioned alkyl is optionally substituted by 1-3 F-atoms $R^{1.3}$ is selected from the group consisting of H, Cl, F, CN, $C_{1-4}$-alkyl, and $C_{1-4}$-alkyl-O—;

$R^{1.4}$ is selected from the group consisting of H, —CN, Br, Cl, F and $C_{1-4}$-alkyl optionally substituted by 1-3 F-atoms, $R^{1.5}$ H or $C_{1-4}$-alkyl, $R^2$ and $R^3$ are independently from each other selected from the group consisting of H and $C_{1-3}$-alkyl, or $R^2$ and $R^3$ together form a 3 to 6 membered carbocycle, a 4 to 6 membered heterocycle containing 1 O atom or 1 N atom or a 5 to 9 membered heteroaryl containing 1-2 N-atoms;

$R^4$ denotes $R^{4.1}R^{4.2}N$— or NC—;

or $R^4$ denotes a group of formula $R^{4.a}$

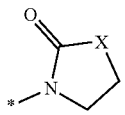

$R^{4.a}$ wherein

X denotes $CH_2$ or O;

$R^{4.1}$ is selected from the group consisting of $C_{1-4}$-alkyl-CO—, 6-membered heteroaryl containing 1-2 N-atoms, $C_{3-5}$-cycloalkyl-CO— substituted by $R^{4.1.1}$ and $R^{4.1.2}$, Phenyl-CO— optionally substituted by 1-2 halogen atoms, $C_{1-4}$-alkyl- or $CH_3$—O— and 5 to 6 membered heteroaryl-CO— optionally substituted by $C_{1-4}$-alkyl- or $CH_3$—O—.

wherein $R^{4.1.1}$, $R^{4.1.2}$ independently from each other are selected from the group consisting of H, —$CH_3$, F, and —CN;

$R^{4.2}$ denotes H or $C_{1-3}$-alkyl, $R^5$ denotes H or methyl;

or $R^4$ and $R^5$ together form 4-6 membered heterocyclyl containing 1-2 heteroatoms selected from the group consisting of N and O;

or a pharmaceutically acceptable salt thereof.

Preferred Embodiments

In another embodiment of the present invention $R^1$ denotes H.

In another embodiment of the present invention $R^1$ denotes phenyl substituted by $R^{1.1}$ and $R^{1.3}$.

In another embodiment of the present invention $R^1$ denotes pyridinyl.

In another embodiment of the present invention $R^1$ denotes 5-6 membered heteroaryl containing 1 to 3 heteroatoms selected from the group consisting of S, N and O substituted by $R^{1.2}$ and $R^{1.5}$.

In another embodiment of the present invention $R^1$ denotes 5-6 membered heterocyclyl containing 1 or 2 heteroatoms selected from the group consisting of S, N and O substituted by $R^{1.4}$.

In another embodiment of the present invention $R^1$ is selected from the group consisting of pyrimidinyl, pyrazinyl, pyridazinyl, thiazolyl, thiophenyl and pyridinyl, independently from each other substituted by $R^{1.2}$.

In another embodiment of the present invention $R^1$ denotes pyrazolyl substituted by $R^{1.5}$.

In another embodiment of the present invention $R^1$ is selected from the group consisting of H, pyrimidinyl, pyrazinyl, pyridazinyl, thiazolyl, thiophenyl, phenyl substituted by $R^{1.1}$ and $R^{1.3}$, pyridinyl substituted by $R^{1.2}$, and pyrazolyl substituted by $R^{1.5}$.

In another embodiment of the present invention $R^{1.1}$ is selected from the group consisting of H, —CN, Cl, F, $CF_3$, $HF_2C$— $H_2N$—$S(O)_2$—, $H_3C$—NH—$S(O)_2$—, $(H_3C)_2N$—$S(O)_2$—, $H_3C$—NH—CO—, $H_3C$—O—CO—. $H_2N$—CO—, $H_3C$—CO—NH—, and 5-membered heteroaryl containing 1-3 heteroatoms selected from the group N and O optionally substituted by $CF_3$, $F_3C$—$CH_2$ or $HF_2C$—;

$R^{1.2}$ is selected from the group consisting of H, —CN, methyl, Br, Cl, F, $H_3C$—O—, $CF_3$, $H_2N$— and $(H_3C)_2N$—;

$R^{1.3}$ denotes H or F;

$R^{1.4}$ denotes H or $F_3C$—$CH_2$—;

and $R^{1.5}$ denotes H, methyl or butyl.

In another embodiment of the present invention $R^{1.1}$ is selected from the group consisting of H, —CN, Cl, F, $CF_3$, $HF_2C$— $H_2N$—$S(O)_2$—, $H_3C$—NH—$S(O)_2$—, $(H_3C)_2N$—$S(O)_2$—, $H_3C$—NH—CO—, $H_3C$—O—CO—. $H_2N$—CO—, $H_3C$—CO—NH— and oxadiazolyl substituted by $F_3C$—$CH_2$—;

In another embodiment of the present invention $R^{1.2}$ is selected from the group consisting of H, —CN, methyl, Br, Cl, F, $H_3C$—O—, $CF_3$, $H_2N$— and $(H_3C)_2N$—, preferably H;

In another embodiment of the present invention $R^{1.3}$ denotes H or F;

In another embodiment of the present invention $R^{1.4}$ denotes H or $F_3C$—$CH_2$—;

In another embodiment of the present invention $R^{1.5}$ denotes H, methyl or butyl.

In another embodiment of the present invention $R^2$ denotes H or $C_{1-2}$-alkyl.

In another embodiment of the present invention $R^2$ denotes H

In another embodiment of the present invention $R^2$ denotes methyl.

In another embodiment of the present invention $R^2$ denotes ethyl.

In another embodiment of the present invention $R^3$ denotes H or $C_{1-2}$-alkyl.

In another embodiment of the present invention $R^3$ denotes H.

In another embodiment of the present invention $R^3$ denotes methyl.

In another embodiment of the present invention $R^3$ denotes ethyl.

In another embodiment of the present invention $R^2$ and $R^3$ denote H

In another embodiment of the present invention $R^2$ and $R^3$ denote methyl.

In another embodiment of the present invention $R^2$ denotes methyl and $R^3$ denotes H.

In another embodiment of the present invention $R^2$ and $R^3$ together form a $C_{3-4}$-cycloalkyl or 8 to 9 membered heteroaryl containing 1-2 N-atoms.

In another embodiment of the present invention $R^2$ and $R^3$ together form cyclopropyl.

In another embodiment of the present invention $R^2$ and $R^3$ together form cyclobutyl.

In another embodiment of the present invention $R^2$ and $R^3$ together form 8 to 9 membered heteroaryl selected from the group consisting of formula (a) to (c).

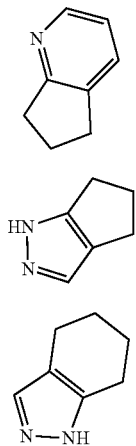

(a)

(b)

(c)

In another embodiment of the present invention $R^4$ denotes $R^{4.1}R^{4.2}N$ or NC—.

In another embodiment of the present invention $R^4$ denotes $R^{4.1}R^{4.2}N$.

In another embodiment of the present invention $R^4$ denotes NC—.

In another embodiment of the present invention $R^4$ denotes a group of formula $R^{4.a}$.

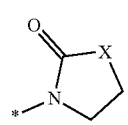

$R^{4.a}$

In another embodiment of the present invention
$R^{4.1}$ is selected from the group consisting of $C_{1-4}$-alkyl-CO—, pyrimidinyl, $C_{3-4}$-cycloalkyl-CO— substituted by $R^{4.1.1}$ and $R^{4.1.2}$,
wherein
$R^{4.1.1}$, $R^{4.1.2}$ independently from each other are selected from the group consisting of H, —$CH_3$, F and —CN; and
$R^{4.2}$ denotes H or methyl.

In another embodiment of the present invention $R^{4.1}$ denotes $C_{1-4}$-alkyl-CO—.

In another embodiment of the present invention $R^{4.1}$ denotes $H_3C$—CO—.

In another embodiment of the present invention $R^{4.2}$ denotes H.

In another embodiment of the present invention $R^{4.2}$ denotes methyl.

In another embodiment of the present invention $R^{4.1}$ denotes $H_3C$—CO— and $R^{4.2}$ denotes methyl.

In another embodiment of the present invention $R^{4.1}$ denotes pyrimidinyl.

In another embodiment of the present invention $R^{4.1}$ denotes $C_{3-4}$-cycloalkyl-CO— substituted by $R^{4.1.1}$ and $R^{4.1.2}$ In another embodiment of the present invention $R^{4.1.1}$ is selected from the group consisting of H, $CH_3$, F and —CN;

In another embodiment of the present invention $R^{4.1.1}$ denotes H.

In another embodiment of the present invention $R^{4.1.2}$ denotes H or F.

In another embodiment of the present invention $R^{4.1.2}$ denotes H.

In another embodiment of the present invention $R^5$ denotes H or methyl.

In another embodiment of the present invention $R^5$ denotes H.

In another embodiment of the present invention $R^5$ denotes methyl.

In another embodiment of the present invention $R^4$ denotes $R^{4.1}R^{4.2}N$, $R^{4.1}$ denotes $C_{1-4}$-alkyl-CO— and $R^5$ denotes H.

Another embodiment of the present invention is a compound of formula I, wherein
wherein
$R^1$ is selected from the group consisting of H, phenyl substituted by $R^{1.1}$ and $R^{1.3}$, 5-6 membered heteroaryl containing 1 to 3 heteroatoms selected from the group consisting of S, N and O substituted by $R^{1.2}$ and $R^{1.5}$, 5-6 membered heterocyclyl containing 1 or 2 heteroatoms selected from the group consisting of S, N and O substituted by $R^{1.4}$;
Wherein
$R^{1.1}$ is selected from the group consisting of H, —CN, Br, Cl, F, $CF_3$, $F_3C$—$CH_2$, $HF_2C$— $H_2N$—$S(O)_2$—, $H_3C$—NH—$S(O)_2$—, $(H_3C)_2N$—$S(O)_2$—, $H_3C$—NH—CO—, $H_3C$—O—, $H_3C$—O—CO—. $H_2N$—, $(H_3C)_2N$—, $H_2N$—CO—, $H_3C$—CO—NH— and 5-membered heteroaryl containing 1-3 heteroatoms selected from the group N and O optionally substituted by $CF_3$, $F_3C$—$CH_2$ or $HF_2C$—;
$R^{1.2}$ is selected from the group consisting of H, —CN, Br, Cl, F, $CF_3$, $F_3C$—$CH_2$, $HF_2C$— $H_2N$—$S(O)_2$—, $H_3C$—NH—$S(O)_2$—, $(H_3C)_2N$—$S(O)_2$—, $H_3C$—NH—CO—, $H_3C$—O—, $H_3C$—O—CO—. $H_2N$—, $(H_3C)_2N$—, $H_2N$—CO— and $H_3C$—CO—NH—;
$R^{1.3}$ denotes H or F;
$R^{1.4}$ is selected from the group consisting of H, —CN, Br, Cl, F, $C_{1-4}$-alkyl, $CF_3$, $F_3C$—$CH_2$, $HF_2C$— $H_2N$—$S(O)_2$—, $H_3C$—NH—$S(O)_2$—, $(H_3C)_2N$—$S(O)_2$—, $H_3C$—NH—CO—, $H_3C$—O—, $H_3C$—O—CO—. $H_2N$—, $(H_3C)_2N$—, $H_2N$—CO— and $H_3C$—CO—NH—;
$R^{1.5}$ H or $C_{1-4}$-alkyl,
$R^2$ and $R^3$ are independently from each other selected from the group consisting of H and $C_{1-3}$-alkyl,
or
$R^2$ and $R^3$ together form a 3-6 membered carbocycle or a 5 to 9 membered heteroaryl containing 1-2 N-atoms;
$R^4$ denotes $R^{4.1}R^{4.2}N$— or NC—;
or
$R^4$ denotes a group of formula $R^{4.a}$

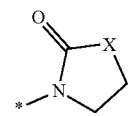

$R^{4.a}$ wherein
X denotes $CH_2$ or O;
$R^{4.1}$ is selected from the group consisting of $C_{1-4}$-alkyl-CO—, 6-membered heteroaryl containing 1-2 N-atoms, $C_{3-4}$-cycloalkyl-CO— substituted by $R^{4.1.1}$ and $R^{4.1.2}$
wherein
$R^{4.1.1}$, $R^{4.1.2}$ independently from each other are selected from the group consisting of H, —$CH_3$, F, and —CN;
$R^{4.2}$ denotes H or methyl,
$R^5$ denotes H or methyl;
or
$R^4$ and $R^5$ together form 5-6 membered heterocyclyl containing 1-2 heteroatoms selected from the group consisting of N and O.

Another embodiment of the present invention is a compound of formula I, wherein
$R^1$ is selected from the group consisting of H, pyrimidinyl, pyrazinyl, pyridazinyl, thiazolyl, thiophenyl, phenyl substituted by $R^{1.1}$ and $R^{1.3}$, pyridinyl substituted by $R^{1.2}$, and pyrazolyl substituted by $R^{1.5}$;
wherein
$R^{1.1}$ is selected from the group consisting of H, —CN, Cl, F, $CF_3$, $HF_2C$— $H_2N$—$S(O)_2$—, $H_3C$—NH—S$(O)_2$—, $(H_3C)_2N$—$S(O)_2$—, $H_3C$—NH—CO—, $H_3C$—O—CO—. $H_2N$—CO—, $H_3C$—CO—NH— and oxadiazolyl optionally substituted by $CF_3$, $F_3C$—$CH_2$ and $HF_2C$—;
$R^{1.2}$ is selected from the group consisting of H, —CN, methyl, Br, Cl, F, $H_3C$—O—, $CF_3$, $H_2N$— and $(H_3C)_2N$—;
$R^{1.3}$ denotes H or F;
$R^{1.4}$ denotes H or $F_3C$—$CH_2$—;
$R^{1.5}$ denotes H, methyl or butyl;
$R^2$ and $R^3$ are independently from each other selected from the group consisting of H and $C_{1-2}$-alkyl, or
$R^2$ and $R^3$ together form a $C_{3-4}$-cycloalkyl or a 8 to 9 membered heteroaryl containing 1-2 N-atoms;
$R^4$ denotes $R^{4.1}R^{4.2}N$— or NC—;
or $R^4$ denotes a group of formula $R^{4.a}$ $R^{4.a}$ wherein
X denotes $CH_2$ or O;
$R^{4.1}$ is selected from the group consisting of $C_{1-4}$-alkyl-CO—, pyrimidinyl, $C_{3-4}$-cycloalkyl-CO— substituted by $R^{4.1.1}$ and $R^{4.1.2}$, wherein
$R^{4.1.1}$, $R^{4.1.2}$ independently from each other are selected from the group consisting of H, —$CH_3$, F and —CN;
$R^{4.2}$ denotes H or methyl
$R^5$ denotes H or methyl;
or
$R^4$ and $R^5$ together form oxanyl;
or a pharmaceutically acceptable salt thereof.

Any and each of the definitions of $R^1$, $R^2$, $R^3$, $R^4$, $R^5$, $R^{4.1}$, $R^{4.2}$, $R^{4.1.1}$, $R^{4.1.2}$, $R^{1.1}$, $R^{1.2}$, $R^{1.3}$, $R^{1.4}$, $R^{1.5}$ and X may be combined with each other.

In a preferred embodiment of the present invention a compound of formula I is selected from the group consisting of examples 1.11, 1.28, 1.44, 2.2, 2.3, 3.2, 4.1, 4.3, 7.1, 9.3, 9.4 and 9.6.

Ex. 1.11

Ex. 1.28

Ex. 1.44

Ex. 2.2

Ex. 2.3

Ex. 3.2

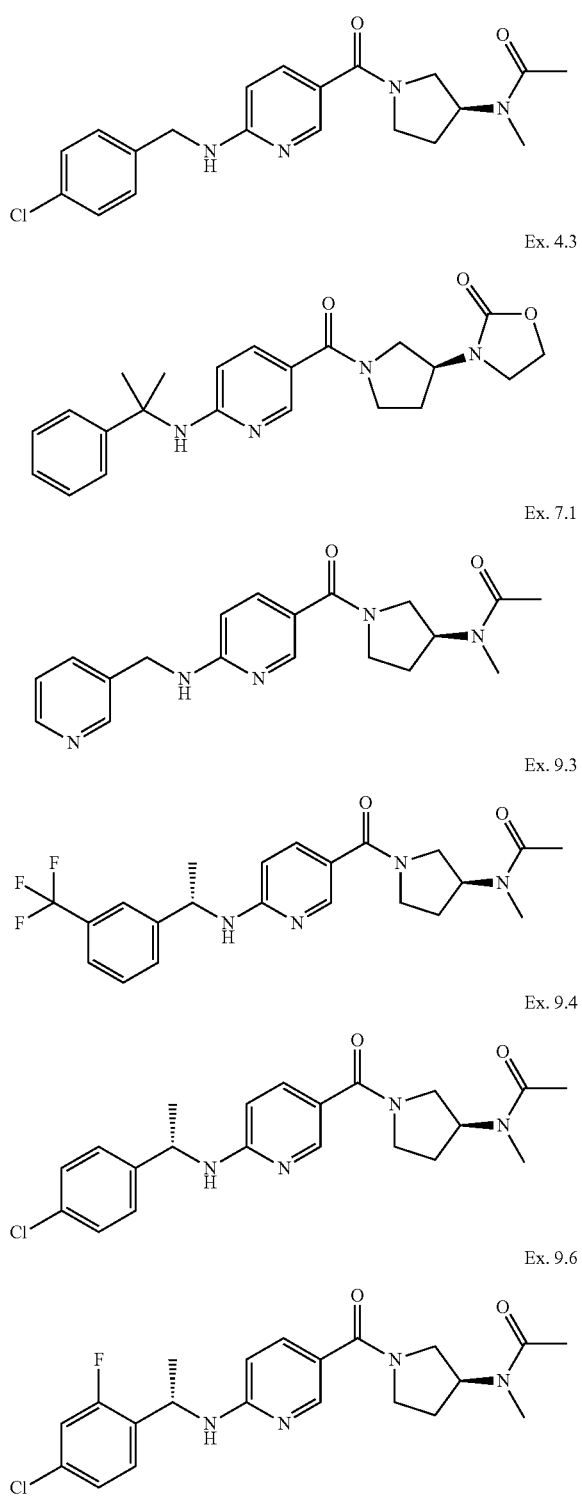

* The stereochemistry at the chiral center of the enantiomerically and diastereomerically pure compound was not determined.

or a pharmaceutically acceptable salt thereof.

A further preferred embodiment of the current invention are the above compounds of formula I, selected from the group consisting of examples 1.11, 1.28, 1.44, 2.2, 2.3, 3.2, 4.1, 4.3, 7.1, 9.3, 9.4 and 9.6.

A further preferred embodiment of the current invention are the above compounds of formula I, selected from the group consisting of examples 1.11, 1.28, 1.44, 2.2, 2.3, 4.1, 7.1, 9.3, 9.4 and 9.6.

A further preferred embodiment of the current invention is the compound of example 1.11.

A further preferred embodiment of the current invention is the compound of example 1.28

A further preferred embodiment of the current invention is the compound of example 1.44.

A further preferred embodiment of the current invention is the compound of example 2.2.

A further preferred embodiment of the current invention is the compound of example 2.3.

A further preferred embodiment of the current invention is the compound of example 3.2.

A further preferred embodiment of the current invention is the compound of example 4.1.

A further preferred embodiment of the current invention is the compound of example 4.3.

A further preferred embodiment of the current invention is the compound of example 7.1.

A further preferred embodiment of the current invention is the compound of example 9.3.

A further preferred embodiment of the current invention is the compound of example 9.4.

A further preferred embodiment of the current invention is the compound of example 9.6.

A further preferred embodiment of the current invention are pharmaceutically acceptable salts of the above compounds of formula I, selected from the group consisting of examples 1.11, 1.28, 1.44, 2.2, 2.3, 3.2, 4.1, 4.3, 7.1, 9.3, 9.4 and 9.6.

A further preferred embodiment of the current invention are pharmaceutically acceptable salts of the above compounds of formula I, selected from the group consisting of examples 1.11, 1.28, 1.44, 2.2, 2.3, 4.1, 7.1, 9.3, 9.4 and 9.6.

A further preferred embodiment of the current invention are pharmaceutically acceptable salts of the compound of example 1.11.

A further preferred embodiment of the current invention are pharmaceutically acceptable salts of the compound of example 1.28.

A further preferred embodiment of the current invention are pharmaceutically acceptable salts of the compound of example 1.44.

A further preferred embodiment of the current invention are pharmaceutically acceptable salts of the compound of example 2.2.

A further preferred embodiment of the current invention are pharmaceutically acceptable salts of the compound of example 2.3.

A further preferred embodiment of the current invention are pharmaceutically acceptable salts of the compound of example 4.1.

A further preferred embodiment of the current invention are pharmaceutically acceptable salts of the compound of example 7.1.

A further preferred embodiment of the current invention are pharmaceutically acceptable salts of the compound of example 9.3.

A further preferred embodiment of the current invention are pharmaceutically acceptable salts of the compound of example 9.4.

A further preferred embodiment of the current invention are pharmaceutically acceptable salts of the compound of example 9.6.

A further embodiment of the present invention is a pharmaceutical composition comprising a therapeutically effective amount of at least one compound of formula I or a pharmaceutically acceptable salt thereof and one or more pharmaceutically acceptable excipients.

A further embodiment of the current invention is a compound of formula I or a pharmaceutically acceptable salt thereof for use as a medicament.

A further embodiment of the current invention is a pharmaceutical composition comprising a therapeutically effective amount of at least one compound of formula I or a pharmaceutically acceptable salt thereof and one or more pharmaceutically acceptable excipients.

Furthermore, the present invention relates to the use of a compound of general formula I for the treatment and/or prevention of a disease and/or condition associated with or modulated by Vanin-1 or Vanin-2, especially Vanin-1, including but not limited to the treatment and/or prevention of inflammatory diseases, preferably inflammatory bowel diseases.

A further embodiment of the current invention is the use of a compound of formula I for treating a patient suffering from Crohn's disease, ulcerative colitis, atopic dermatitis, systemic sclerosis, Non-Alcoholic Steatohepathitis (NASH), psoriasis, chronic kidney disease, chronic obstructive pulmonary disease, idiopathic pulmonary fibrosis, rheumatoid arthritis, scleroderma, asthma, allergic rhinitis, allergic eczema, juvenile rheumatoid arthritis, juvenile idiopathic arthritis, graft versus host disease, psoriatic arthritis, Hyperlipidemia, colorectal cancer or pancreatic cancer related new onset diabetes.

A further embodiment of the current invention is the use of a compound of formula I for treating a patient suffering from Crohn's disease, ulcerative colitis, systemic sclerosis, Non-Alcoholic Steatohepathitis (NASH), chronic obstructive pulmonary disease or atopic dermatitis, preferably Crohn's disease, ulcerative colitis, systemic sclerosis, Non-Alcoholic Steatohepathitis (NASH) or atopic dermatitis, particularly preferred from Crohn's disease or ulcerative colitis.

A further embodiment of the current invention is the use of a compound of formula I for treating a patient suffering from moderate to severe Crohn's disease.

A further embodiment of the current invention is the use of a compound of formula I for treating a patient suffering from ulcerative colitis.

A further embodiment of the current invention is the use of a compound of formula I for treating a patient suffering from atopic dermatitis.

A further embodiment of the current invention is the use of a compound of formula I for treating a patient suffering from NASH.

In a further embodiment, there is provided a method of treating a disease chosen from Crohn's disease, ulcerative colitis, atopic dermatitis, systemic sclerosis, Non-Alcoholic Steatohepathitis (NASH), psoriasis, chronic kidney disease, chronic obstructive pulmonary disease, idiopathic pulmonary fibrosis, rheumatoid arthritis, scleroderma, asthma, allergic rhinitis, allergic eczema, juvenile rheumatoid arthritis, juvenile idiopathic arthritis, graft versus host disease, psoriatic arthritis, Hyperlipidemia, colorectal cancer or pancreatic cancer related new onset diabetes comprising administering to a patient a therapeutically effective amount of a compound according to the first embodiment or any of its related embodiments or a pharmaceutically acceptable salt thereof.

In a further embodiment, there is provided a process for preparation of a compound according to the first embodiment or any of its related embodiments by the methods shown herein below.

In a further aspect the present invention relates to a compound of general formula 1 for use in the treatment and/or prevention of above mentioned diseases and conditions.

In a further aspect the present invention relates to the use of a compound of general formula 1 for the preparation of a medicament for the treatment and/or prevention of above mentioned diseases and conditions.

In a further aspect the present invention relates to methods for the treatment or prevention of above mentioned diseases and conditions, which method comprises the administration of an effective amount of a compound of general formula 1 to a human being.

The actual pharmaceutically effective amount or therapeutic dosage will usually depend on factors known by those skilled in the art such as age and weight of the patient, route of administration and severity of disease. In any case the compounds will be administered at dosages and in a manner which allows a pharmaceutically effective amount to be delivered based upon patient's unique condition.

A further embodiment of the current invention is a pharmaceutical composition comprising additionally to a compound of formula I, a pharmaceutically active compound selected from the group consisting of an immunomodulatory agent, anti-inflammatory agent, or a chemotherapeutic agent. Examples of such agents include but are not limited to cyclophosphamide, mycophenolate (MMF), hydroxychloroquine, glucocorticoids, corticosteroids, immunosuppressants, NSAIDs, non-specific and COX-2 specific cyclooxygenase enzyme inhibitors, tumour necrosis factor receptor (TNF) receptors antagonists, IL12/23 and IL23 antagonists, α4β7 integrin blocking antibodies, non-selective and selective JAK kinase inhibitors and methotrexate, but also combinations of two or three active substances.

Another embodiment of the present invention are compounds of formula IA or the pharmaceutically acceptable salts thereof.

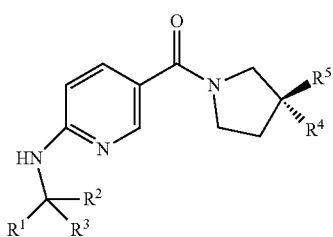

IA

Another embodiment of the present invention are compounds of formula IB or the pharmaceutically acceptable salts thereof.

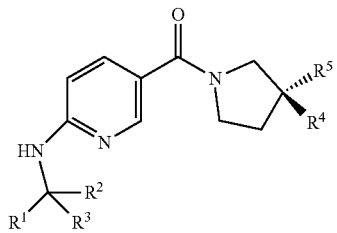

Another embodiment of the present invention are compounds of formula IC or the pharmaceutically acceptable salts thereof.

Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms. In general in groups like HO, $H_2N$, (O)S, (O)$_2$S, CN (cyano), HOOC, $F_3C$ or the like, the skilled artisan can see the radical attachment point(s) to the molecule from the free valences of the group itself. For combined groups comprising two or more subgroups, the last named subgroup is the radical attachment point, for example, the substituent "aryl-$C_{1-3}$-alkyl" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

The numeration of the atoms of a substituent starts with the atom which is closest to the core or to the group to which the substituent is attached.

For example, the term "3-carboxypropyl-group" represents the following substituent:

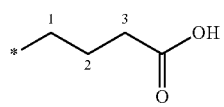

wherein the carboxy group is attached to the third carbon atom of the propyl group. The terms "1-methylpropyl-", "2,2-dimethylpropyl-" or "cyclopropylmethyl-" group represent the following groups:

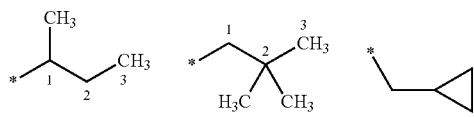

The asterisk may be used in sub-formulas to indicate the bond which is connected to the core molecule as defined.

The term "substituted" as used herein, means that any one or more hydrogens on the designated atom is replaced with a selection from the indicated group, provided that the designated atom's normal valence is not exceeded, and that the substitution results in a stable compound. Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

In general, substantially pure stereoisomers can be obtained according to synthetic principles known to a person skilled in the field, e.g. by separation of corresponding mixtures, by using stereochemically pure starting materials and/or by stereoselective synthesis. It is known in the art how to prepare optically active forms, such as by resolution of racemic forms or by synthesis, e.g. starting from optically active starting materials and/or by using chiral reagents. Enantiomerically pure compounds of this invention or intermediates may be prepared via asymmetric synthesis, for example by preparation and subsequent separation of appropriate diastereomeric compounds or intermediates which can be separated by known methods (e.g. by chromatographic separation or crystallization) and/or by using chiral reagents, such as chiral starting materials, chiral catalysts or chiral auxiliaries.

Further, it is known to the person skilled in the art how to prepare enantiomerically pure compounds from the corresponding racemic mixtures, such as by chromatographic separation of the corresponding racemic mixtures on chiral stationary phases; or by resolution of a racemic mixture using an appropriate resolving agent, e.g. by means of diastereomeric salt formation of the racemic compound with optically active acids or bases, subsequent resolution of the salts and release of the desired compound from the salt; or by derivatization of the corresponding racemic compounds with optically active chiral auxiliary reagents, subsequent diastereomer separation and removal of the chiral auxiliary group; or by kinetic resolution of a racemate (e.g. by enzymatic resolution); by enantioselective crystallization from a conglomerate of enantiomorphous crystals under suitable conditions; or by (fractional) crystallization from a suitable solvent in the presence of an optically active chiral auxiliary.

The phrase "pharmaceutically acceptable" is employed herein to refer to those compounds, materials, compositions, and/or dosage forms which are, within the scope of sound medical judgment, suitable for use in contact with the tissues of human beings without excessive toxicity, irritation, allergic response, or other problem or complication, and commensurate with a reasonable benefit/risk ratio.

As used herein, "pharmaceutically acceptable salt" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid.

Further pharmaceutically acceptable salts can be formed with cations from ammonia, L-arginine, calcium, 2,2'-iminobisethanol, L-lysine, magnesium, N-methyl-D-glucamine, potassium, sodium and tris(hydroxymethyl)-aminomethane.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

The term halogen generally denotes fluorine, chlorine, bromine and iodine.

The term "$C_{1-n}$-alkyl", wherein n is an integer selected from 2, 3, 4, 5 or 6, preferably 4 or 6, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{3-n}$-cycloalkyl", wherein n is an integer from 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The term "carbocyclyl" or "carbocycle" as used either alone or in combination with another radical, means a mono- bi- or tricyclic ring structure consisting of 3 to 14 carbon atoms. The term "carbocyclyl" or "carbocycle" refers to fully saturated and aromatic ring systems and partially saturated ring systems. The term "carbocyclyl" or "carbocycle" encompasses fused, bridged and spirocyclic systems.

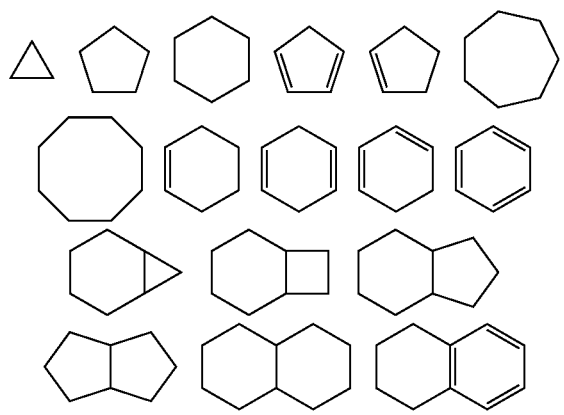

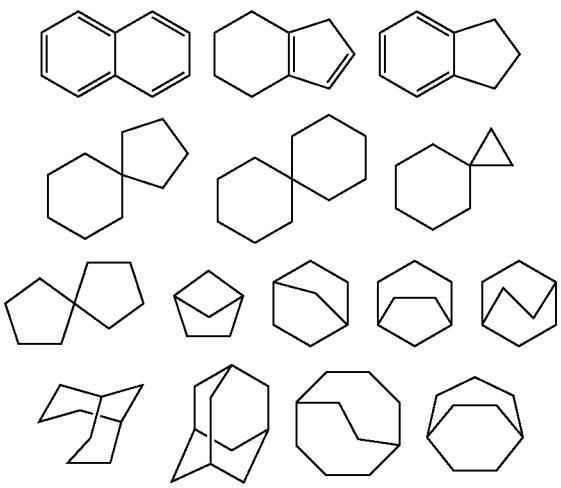

The term "aryl" as used herein, either alone or in combination with another radical, denotes a carbocyclic aromatic monocyclic group containing 6 carbon atoms which is optionally further fused to a second five- or six-membered, carbocyclic group which is optionally aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heterocyclyl" or "heterocycle" means a saturated or unsaturated mono- or polycyclic-ring systems including aromatic ring system containing one or more heteroatoms selected from N, O or $S(O)_r$, wherein r=0, 1 or 2, consisting of 3 to 14 ring atoms wherein none of the heteroatoms is part of the aromatic ring. The term "heterocyclyl" or "heterocycle" is intended to include all the possible isomeric forms.

Thus, the term "heterocyclyl" or "heterocycle" includes the following exemplary structures which are not depicted as radicals as each form are optionally attached through a covalent bond to any atom so long as appropriate valences are maintained:

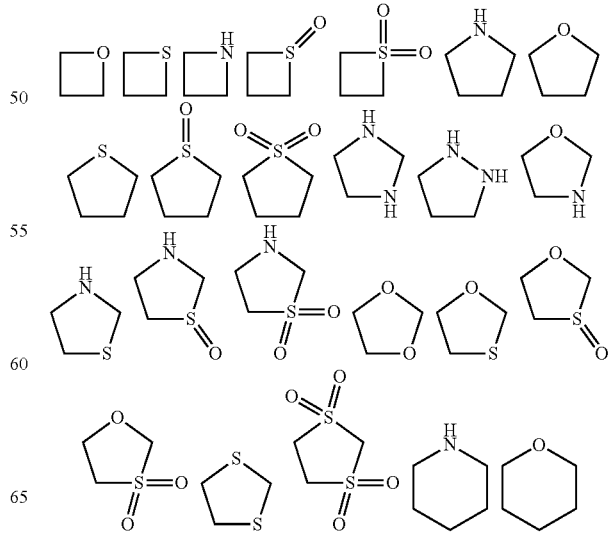

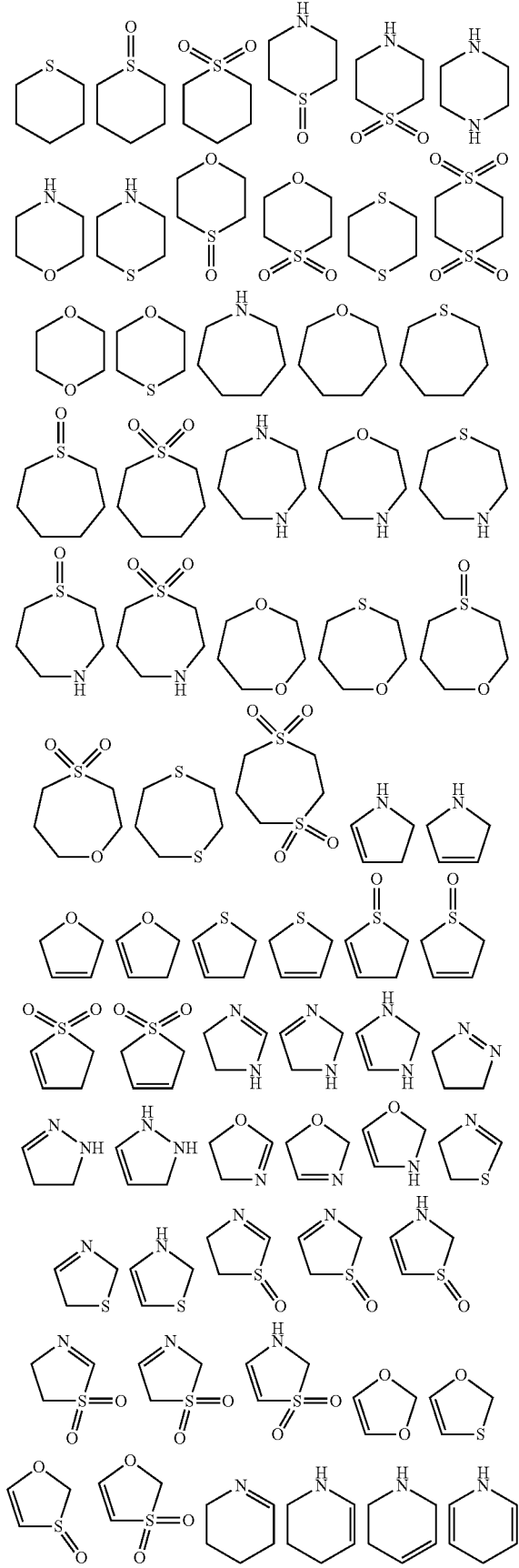
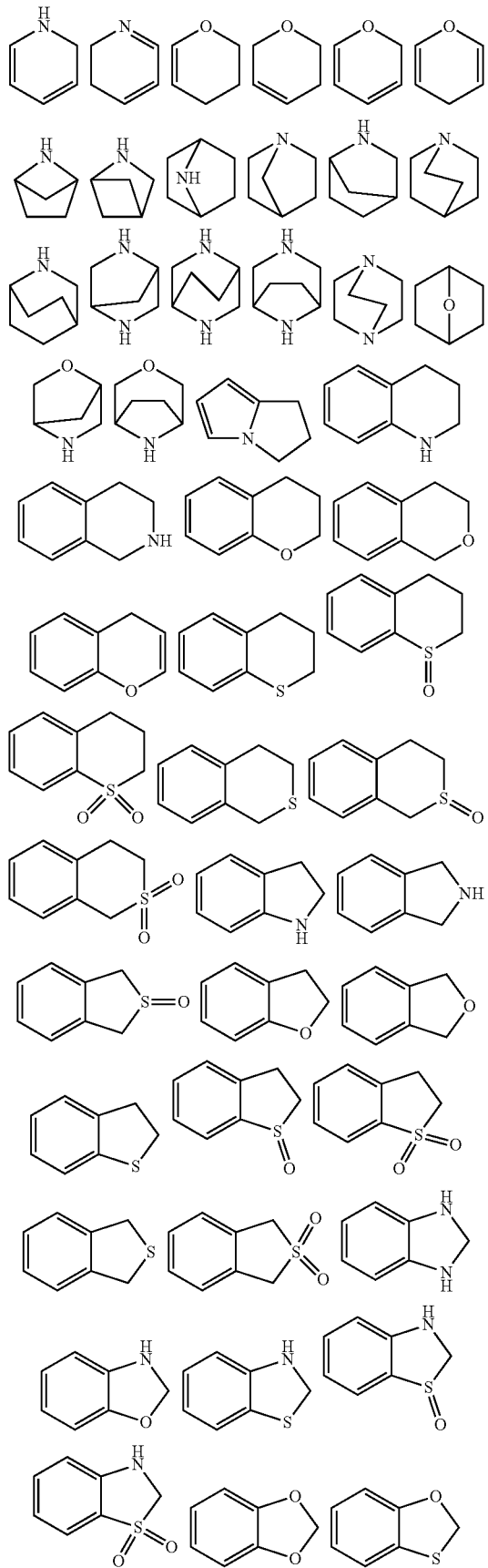

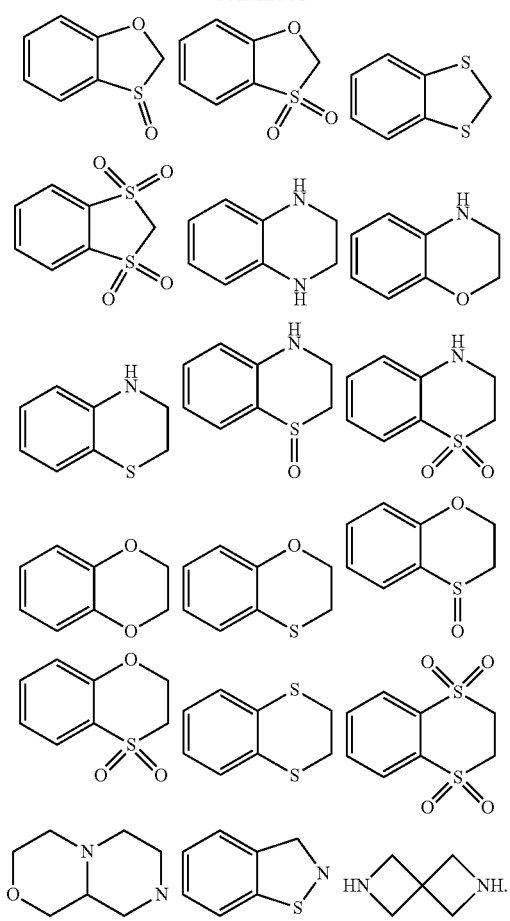

The term "heteroaryl" means a mono- or polycyclic-ring systems containing one or more heteroatoms selected from N, O or S(O)$_r$, wherein r=0, 1 or 2, consisting of 5 to 14 ring atoms wherein at least one of the heteroatoms is part of aromatic ring. The term "heteroaryl" is intended to include all the possible isomeric forms.

Thus, the term "heteroaryl" includes the following exemplary structures which are not depicted as radicals as each form are optionally attached through a covalent bond to any atom so long as appropriate valences are maintained:

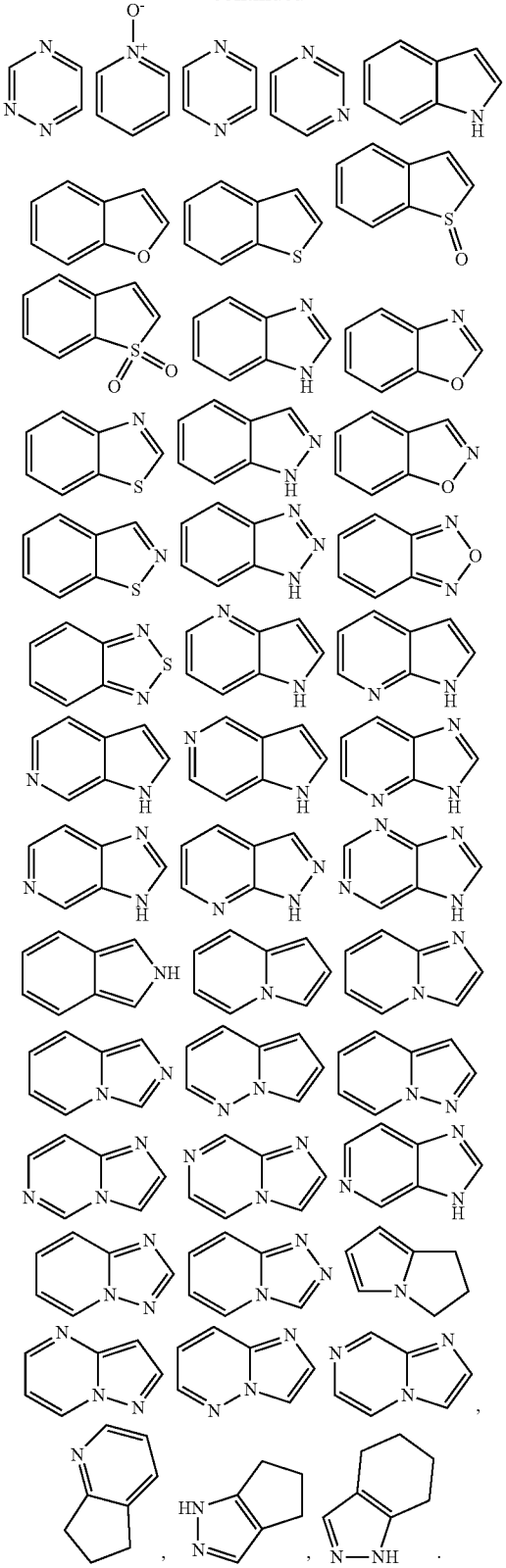

Many of the terms given above may be used repeatedly in the definition of a formula or group and in each case have one of the meanings given above, independently of one another.

Suitable preparations for administering the compounds of formula 1 will be apparent to those with ordinary skill in the art and include for example tablets, pills, capsules, suppositories, lozenges, troches, solutions, syrups, elixirs, sachets, injectables, inhalatives and powders etc., preferably tablets.

Suitable tablets may be obtained, for example, by mixing one or more compounds according to formula I with known excipients, for example inert diluents, carriers, disintegrants, adjuvants, surfactants, binders and/or lubricants.

By a therapeutically effective amount for the purposes of this invention is meant a quantity of substance that is capable of obviating symptoms of illness or alleviating these symptoms, or which prolong the survival of a treated patient.

Features and advantages of the present invention will become apparent from the following detailed examples which illustrate the fundamentals of the invention by way of example without restricting its scope:

Preparation of the Compounds According to the Invention

General Synthetic Methods

The compounds according to the present invention and their intermediates may be obtained using methods of synthesis which are known to the one skilled in the art and described in the literature of organic synthesis. Preferably, the compounds are obtained in analogous fashion to the methods of preparation explained more fully hereinafter, in particular as described in the experimental section. In some cases, the order in carrying out the reaction steps may be varied. Variants of the reaction methods that are known to the one skilled in the art but not described in detail here may also be used.

The general processes for preparing the compounds according to the invention will become apparent to the one skilled in the art studying the following schemes. Starting materials may be prepared by methods that are described in the literature or herein, or may be prepared in an analogous or similar manner. Any functional groups in the starting materials or intermediates may be protected using conventional protecting groups. These protecting groups may be cleaved again at a suitable stage within the reaction sequence using methods familiar to the one skilled in the art.

The compounds according to the invention are prepared by the methods of synthesis described hereinafter in which the substituents of the general formulae have the meanings given hereinbefore. These methods are intended as an illustration of the invention without restricting its subject matter and the scope of the compounds claimed to these examples. Where the preparation of starting compounds is not described, they are commercially obtainable or may be prepared analogously to known compounds or methods described herein. Substances described in the literature are prepared according to the published methods of synthesis.

Compounds of formula (I) may be prepared as shown in Scheme I below.

Scheme I

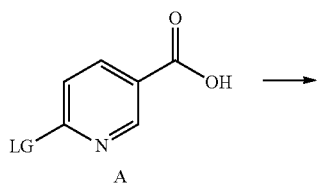

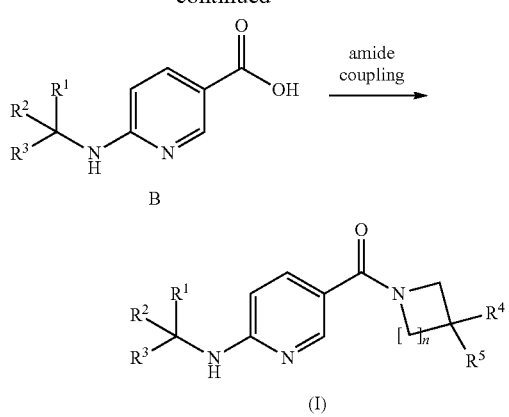

In scheme I, pyridine A, is treated with an appropriate primary amine under elevated temperature to generate pyridine B. An amide coupling (e.g. TBTU or HATU as coupling reagent) with an appropriate heterocycle as next step affords the compound of general formula (I).

Alternatively compounds of formula (I) may be prepared as shown in Scheme II below.

Scheme II

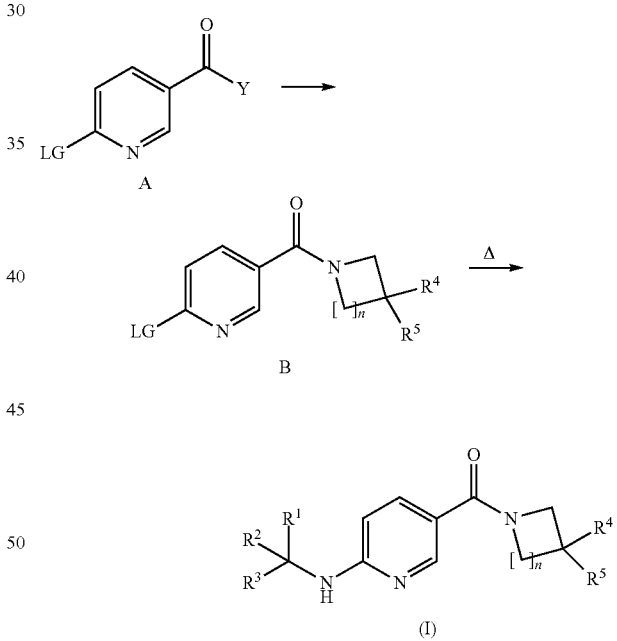

In scheme II, acid chloride A (Y=Cl) is treated with an appropriate heterocycle to generate pyridine B. Alternatively carboxylic acid (Y=OH) is treated with an appropriate heterocycle in the presence of a coupling reagent (e.g. TBTU or HATU) to generate pyridine B. The leaving group (LG) in pyridine B can be replaced by an appropriate primary amine using elevated temperature to afford the compound of general formula (I).

The heterocyclic amines used in the previously described reactions can be obtained by using methods known to those skilled in the art, as exemplified in the Scheme III below:

Scheme III

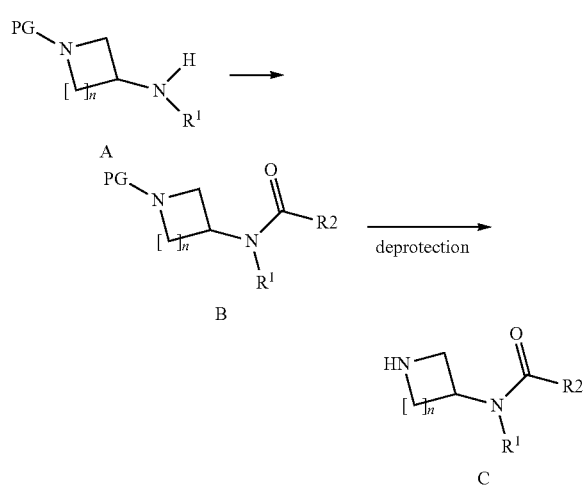

In scheme III, amine A is acylated with an appropriate acylating agent to generate amide B which can be further deprotected (e.g. HCl or TFA for PG=BOC) to yield the desired amine C.

A further option of generating these desired amines is depicted in Scheme IV below:

Scheme IV

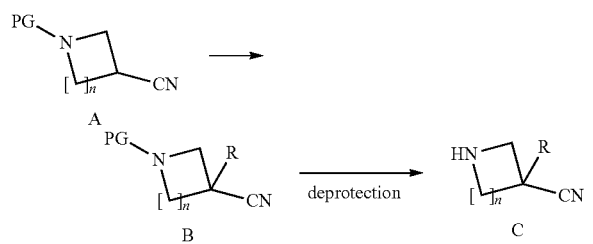

In scheme IV, nitrile A is treated with an alkylating agent under basic conditions to generate nitrile B and subsequently deprotected (e.g. HCl or TFA for PG=BOC) to yield the amine C.

Compounds of formula (II) may be prepared as shown in Scheme V:

Scheme V

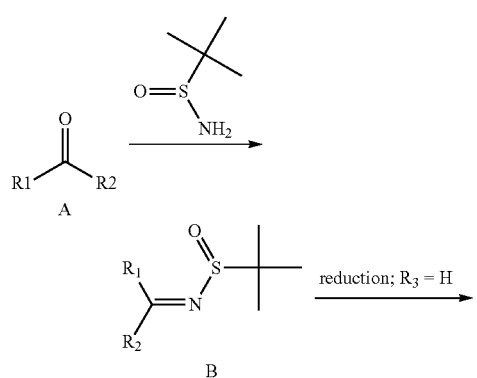

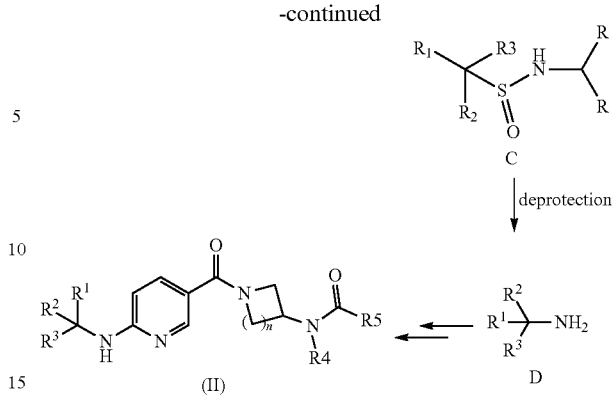

In scheme V, a ketone or aldehyde A is reacted with an appropriate auxiliary (e.g. alkyl sulfinamide) to yield compound B. This imin is reduced with a borohydride reagent to yield intermediates C. After deprotection to amine D (e.g. with HCl), compounds of formula (II) are then obtained.

Experimental Part

Features and advantages of the present invention will become apparent from the following detailed examples which illustrate the fundamentals of the invention by way of example without restricting its scope.

The terms "ambient temperature" and "room temperature" are used interchangeably and designate a temperature of about 20° C., e.g. between 19 and 24° C.

Abbreviations

| | |
|---|---|
| ACN | Acetonitrile |
| Aq. | Aqueous |
| BOC | tert-Butoxycarbonyl |
| ° C. | Degree celsius |
| CDI | Carbonyldiimidazole |
| $CO_2$ | Carbon dioxide |
| Conc. | Concentrated |
| DCM | Dichloromethane |
| DIPEA | N,N-Diisopropylethylamine |
| DMF | N,N-Dimethylformamide |
| DMSO | Dimethyl sulfoxide |
| ESI-MS | Electro spray ionisation mass spectrometry |
| EtOAc/EE | Ethyl acetate |
| EtOH | Ethanol |
| Eq | Equivalent |
| Ex | Example |
| Exc. | Excess |
| h | Hour |
| H2O | Water |
| HATU | N,N,N',N'-Tetramethyl-O-(7-azabenzotriazol-1-yl)uranium hexafluorophosphate |
| HCl | Hydrochlorid acid |
| HPLC | High performance liquid chromatography |
| HCOOH | Formic acid |
| L | Liter |
| LHMDS | Lithium bis(trimethylsilyl)amide |
| MeOH | Methanol |
| M | Molar weight |
| mg | Milligramm |
| min | Minute |
| mL | Milliliter |
| mmol | Millimol |
| MTBE | tert-Butylmethylether |
| MPLC | Medium performance liquid chromatography |
| MW | Molecular Weight |
| $NaHCO_3$ | Sodium bicarbonate |

| | |
|---|---|
| NH₃ | Ammonia |
| NH₄OH | Ammonium hydroxide |
| No. | Number |
| PE | Petroleum Ether |
| PTK | Phase transfer cartridge |
| RT | Room temperature (about 20° C.) |
| $R_t$ | Retention time |
| sat. | Saturated |
| sc | Super critical |
| TBAOH | Tetrabutylammonium hydroxide |
| TB TU | Benzotriazolyl tetramethyluronium tetrafluoroborate |
| TEA | Triethylamine |
| TFA | Trifluoroacetic acid |
| THF | Tetrahydrofuran |
| Ti(iPrO)₄ | Titanium(IV) isopropoxide |
| TLC | Thin-layer chromatography on SiO2 |

Preparation of Starting Compounds

Example I

Example I.1

N-[(3S)-1-(6-Fluoropyridine-3-carbonyl)pyrrolidin-3-yl]-N-methylacetamide

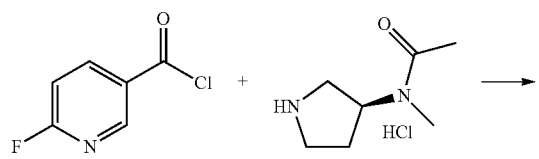

4.00 g (22.38 mmol) N-Methyl-N-[(3S)-pyrrolidin-3-yl] acetamide (CAS No. 1215264-39-3) and 14.83 mL (106.55 mmol) TEA are diluted with 30 mL DCM and cooled with an ice-bath. 3.40 g (21.31 mmol) 2-Fluoropyridine-5-carbonyl chloride (CAS No. 65352-94-5) dissolved in 5 mL DCM is added to the mixture. The reaction mixture is stirred at 0° C. for 10 min. The precipitate is filtered and the filtrate is purified by column chromatography (silica gel; DCM/MeOH) to provide the product.

$C_{13}H_{16}FN_3O_2$ (M=265.28 g/mol)

ESI-MS: 266 [M+H]⁺

$R_t$ (HPLC): 0.63 min (method A)

Example II

Example II.1

(3S)-1-(6-Fluoropyridine-3-carbonyl)-N-methylpyrrolidin-3-amine hydrochloride

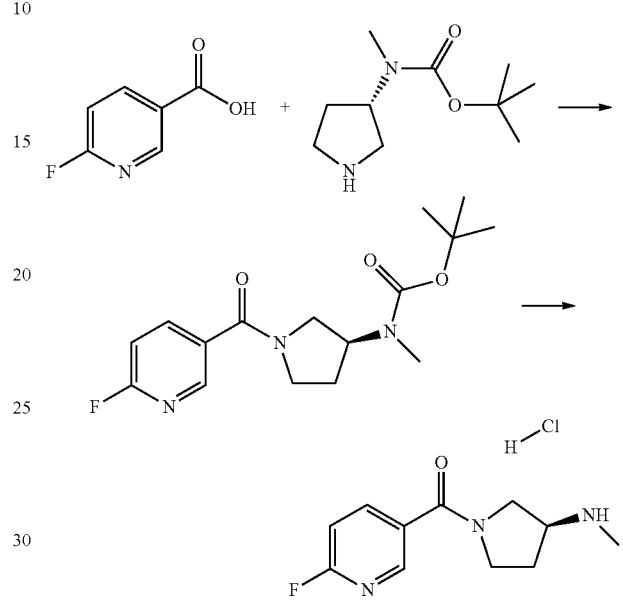

1.00 g (7.09 mmol) 6-Fluoronicotinic acid (CAS No. 403-45-2), 1.56 g (7.80 mmol) (S)-3-(N—BOC—N-methylamino)pyrrolidine (CAS No. 169750-01-0), 2.62 g (8.15 mmol) TBTU and 1.84 mL (10.63 mmol) DIPEA are diluted with 7 mL DMF and stirred at RT. The reaction mixture is treated with water and sat. NaHCO₃ solution and the aqueous layer is extracted three times with EtOAc. The pooled organic phases are dried with MgSO₄, filtered and reduced in vacuo.

The crude product is diluted with 20 mL 1,4-dioxane and 10 mL hydrogenchloride (4 N in 1,4-dioxane) is added, then the reaction mixture is stirred at RT for 3 h. The solvent is evaporated under reduced pressure to obtain the product.

$C_{11}H_{14}FN_3O$*HCl (M=259.71 g/mol)

ESI-MS: 224 [M+H]⁺

$R_t$ (HPLC): 0.60 min (method C)

Example III

Example III. 1

N-[(3S)-1-(6-Fluoropyridine-3-carbonyl)pyrrolidin-3-yl]-N-methylcyclopropane-carboxamide

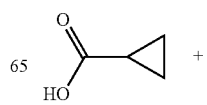 +

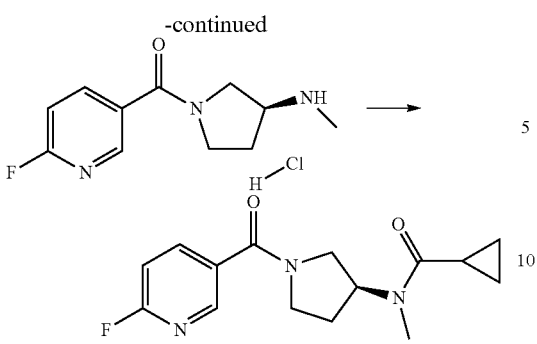

50 mg (0.58 mmol) Cyclopropanecarboxylic acid (CAS No. 1759-53-1), 181 mg (0.70 mmol) N-[(3 S)-1-(6-fluoro-pyridine-3-carbonyl)pyrrolidin-3-yl]-N-methylcyclo-pro-pane-carboxamide (ex. II.1), 214 mg (0.67 mmol) TBTU and 0.30 mL (1.74 mmol) DIPEA are diluted with 4 mL DMF and stirred at RT for 2 h. The reaction mixture is filtered through a microdisk syringe filter and purified by HPLC (ACN/H$_2$O/NH$_4$OH) to give the product.

$C_{15}H_{18}FN_3O_2$ (M=291.32)
ESI-MS: 292 [M+H]$^+$
R$_t$ (HPLC) 0.71 min (method C)

The following compounds are prepared according to the general procedure (example III. 1) described above:

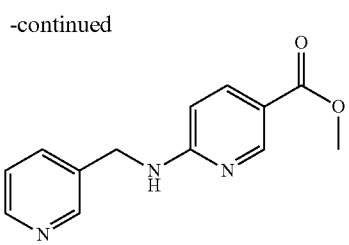

A mixture of 500 mg (3.22 mmol) 6-fluoronicotinic acid methylester (CAS No. 1427-06-1), 349 mg (3.22 mmol) 3-picolylamine (CAS No. 3731-52-0) and 2.21 mL (12.89 mmol) DIPEA in 5 mL DMSO are stirred at 120° C. for 6 h, then filtered through a microdisk syringe filter and purified by HPLC (ACN/H$_2$O/NH$_4$OH) to obtain the product.

$C_{13}H_{13}N_3O_2$ (M=243.26)
ESI-MS: 244 [M+H]$^+$
R$_t$ (HPLC) 0.74 min (method C)

| Ex. | Starting materials | | Structure | ESI-MS | HPLC Rt [min] (method) |
|---|---|---|---|---|---|
| III.2 | ![cyclobutanecarboxylic acid] | II.1 | ![structure] | 306 [M + H]$^+$ | 0.75 (C) |
| III.3 | ![3,3-difluorocyclobutanecarboxylic acid] | II.1 | ![structure] | 342 [M + H]$^+$ | 0.76 (C) |

Example IV

Example IV.1

Methyl 6-{[(pyridin-3-yl)methyl]amino}pyridine-3-carboxylate

Example V

Example V.1

6-{[(Pyridin-3-yl)methyl]amino}pyridine-3-carboxylic acid hydrochloride

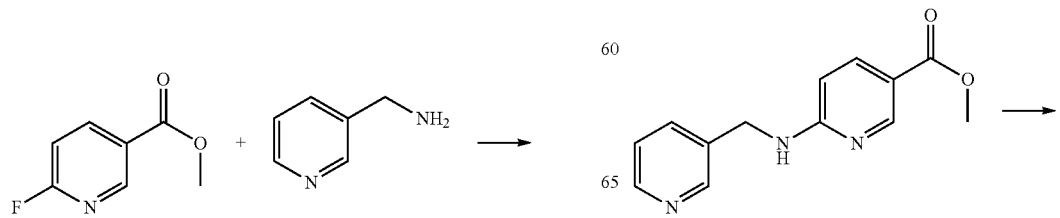

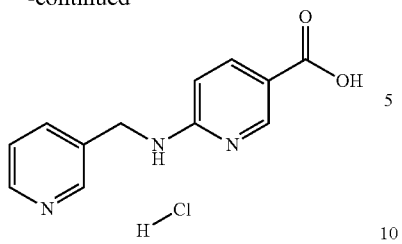

1.6 g (6.58 mmol) Methyl 6-{[(pyridin-3-yl)methyl]amino}pyridine-3-carboxylate (ex. IV.1) and 30.0 mL (180 mmol) 6 N hydrogenchloride are stirred at 95° C. for 3 h. The solvent is evaporated under reduced pressure. The residue is coevaporated once with 30 mL toluene and once with 40 mL ACN, then 30 mL ACN is added. The solid is filtered, washed with 30 mL ACN and dried under reduced pressure at 50° C. for 3 h to provide the product.

$C_{12}H_{11}N_3O_2$*HCl (M=265.70)
ESI-MS: 230 [M+H]$^+$
$R_t$ (HPLC) 0.15 min (method C)

Example VI

Example VI.1

N-Methyl-N-[(3S)-pyrrolidin-3-yl]cyclobutanecarboxamide hydrochloride

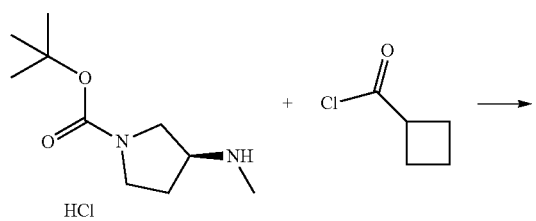

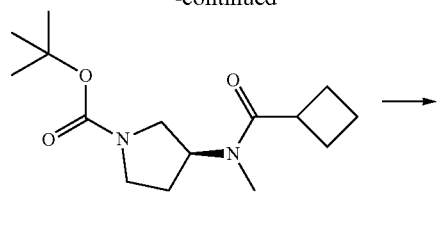

A mixture of 1.00 g (4.22 mmol) tert-butyl (3S)-3-(methylamino)pyrrolidine-1-carboxylate hydrochloride (CAS No. 1004538-30-0) and 2.94 mL (21.12 mmol) TEA in 25 mL DCM is cooled with an ice bath and 0.53 mL (4.65 mmol) cyclobutanecarbonyl chloride (CAS No. 5006-22-4) is added dropwise within 10 min. The precipitate is filtered. The filtrate is diluted with DCM, washed with an aq. sat. NH4Cl solution, then with an aq. sat. NaHCO$_3$ solution and brine, dried with Na$_2$SO$_4$ and reduced in vacuo to provide the BOC-protected product.

$C_{15}H_{20}N_2O_2$ (M=282.38 g/mol)
ESI-MS: 227 [M-tBu+H]$^+$
$R_t$ (HPLC): 0.94 min (method C)

The above mentioned product is dissolved with 3 mL MeOH and 3 mL (12.00 mmol) 4 N hydrogenchloride in 1,4-dioxane is added. The reaction mixture is stirred overnight at RT. The solvent is removed in vacuo to obtain the product.

$C_{10}H_{18}N_2O$*HCl (M=218.72 g/mol)
ESI-MS: 183 [M+H]$^+$
$R_t$ (HPLC): 0.68 min (method C)

The following compound is prepared according to the general procedure (example VI.1) described above:

| Ex. | Starting materials | Structure | Reaction conditions | ESI-MS | HPLC Rt [min] (method) |
|---|---|---|---|---|---|
| VI.2 | ![] ![] | ![] | step 2: 1 h | 169 [M + H]$^+$ | 0.57 (C) |

Example VII

Example VII.1

6-{[(4-Chlorophenyl)methyl]amino}pyridine-3-carboxylic acid

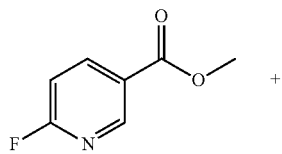 + mmol) DIPEA in 3 mL DMSO is stirred at 120° C. for 2 h. Upon reaction completion, the mixture is diluted with MeOH (2 mL), filtered through a microdisk syringe filter and purified by HPLC to obtain the desired product.

$C_{14}H_{13}ClN_2O_2$ (M=276.72 g/mol)
ESI-MS: 277 [M+H]$^+$
$R_t$ (HPLC): 0.81 min (method C)

The above mentioned product is diluted with 4 mL hydrogenchloride solution (1:1 conc.HCl/H$_2$O) and stirred at 100° C. for 2 h. The solvent is removed in vacuo to obtain the product.

$C_{13}H_{11}ClN_2O_2$ (M=262.69 g/mol)
ESI-MS: 263 [M+H]$^+$
$R_t$ (HPLC): 0.73 min (method A)

The following compounds are prepared according to the general procedure (example VII.1) described above:

| Ex. | Starting materials | Structure | Reaction conditions | ESI-MS | HPLC Rt [min] (method) |
|---|---|---|---|---|---|
| VII.2 | 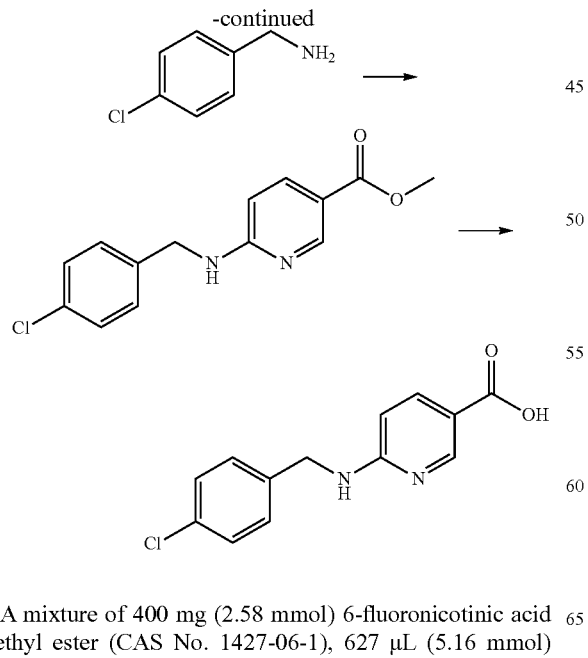 | 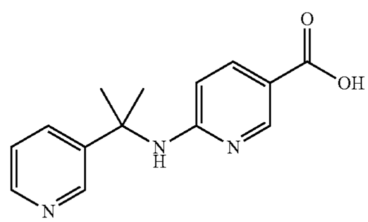 [SMILES: CC(C)(Nc1ccc(C(=O)O)cn1)c1cccnc1] | step 1: overnight; 2 mL semi conc. HCl; 2.5 h at 80° C. | 258 [M + H]$^+$ | 0.28 (A) |
| VII.3 | XIX.1 | 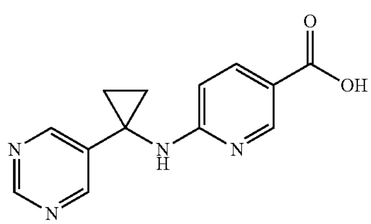 [SMILES: O=C(O)c1ccc(NC2(c3cncnc3)CC2)nc1] | step 1: 4 h step 2: 2.5 h | 257 [M + H]$^+$ | 0.23 (A) |

-continued

A mixture of 400 mg (2.58 mmol) 6-fluoronicotinic acid methyl ester (CAS No. 1427-06-1), 627 µL (5.16 mmol) 4-chlorobenzylamine (CAS No. 104-86-9) and 2.21 mL (10

Example VIII

Example VIII.1

3,3-Difluoro-N-methyl-N-[(3S)-pyrrolidin-3-yl]cyclobutane-1-carboxamide hydrochloride

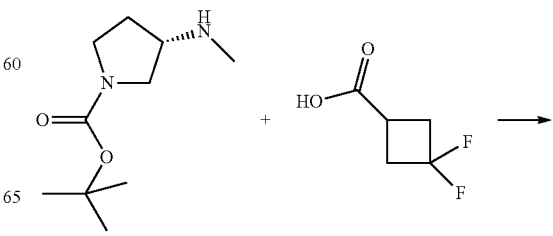

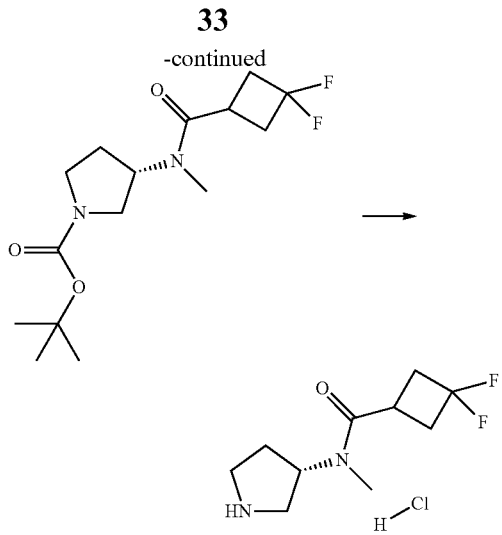

To a mixture containing 1.00 g (4.99 mmol) tert-butyl (3S)-3-(methylamino)pyrrolidine-1-carboxylate (CAS No. 147081-59-2), 0.75 g (5.24 mmol) 3,3-difluorocyclobutanecarboxylic acid (CAS No. 107496-54-8) and 1.72 mL (9.99 mmol) DIPEA dissolved in 10 mL THF is added 1.99 g (5.24 mmol) HATU. The reaction mixture is stirred at RT overnight, then it is reduced in vacuo and the residue is taken up with EtOAc. The organic phase is washed with citric acid (20%) and an aq. sat. NaHCO$_3$ solution, dried with Na$_2$SO$_4$ and the solvent is evaporated under reduced pressure. The crude material is treated with 50 mL hydrogenchloride (1.25 M in EtOH) and the reaction mixture is stirred at RT for 2 h. The mixture is evaporated in vacuo and the residue is coevaporated with iso-propanol to give the product.

$C_{10}H_{16}F_2N_2O_2$*HCl (M=254.70 g/mol)
ESI-MS: 219 [M+H]$^+$
R$_t$ (HPLC): 0.45 min (method B)

Example IX

Example IX.1.A and Example IX.1.B tert-Butyl (3R)-3-cyano-3-methylpyrrolidine-1-carboxylate tert-Butyl (3S)-3-cyano-3-methylpyrrolidine-1-carboxylate

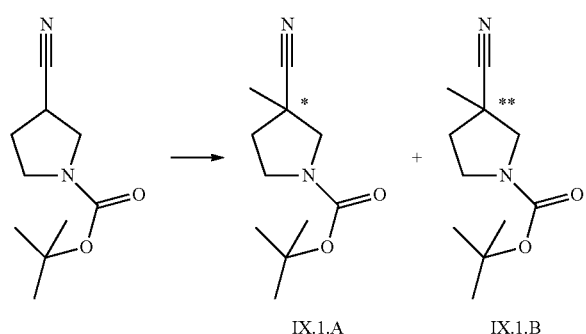

IX.1.A     IX.1.B

To a mixture of 2.70 g (13.8 mmol) tert-butyl 3-cyanopyrrolidine-1-carboxylate (CAS No. 122684-34-8) and 40 mL THF is added 15.1 mL (15.1 mmol) LiHMDS at −78° C. After stirring 30 min at −78° C., 1.28 mL (20.6 mmol) iodomethane is added dropwise. The reaction mixture is stirred 30 min at −78° C. and 30 min at RT. The mixture is poured into 100 mL of a mixture of sat. aq. NH4Cl solution and water (1:1) and extracted twice with EtOAc. The organic layer is washed with brine, dried over MgSO$_4$, filtered and the solvent is evaporated. The crude product is purified by chiral SFC (CHIRAL_ART® Cellulose-SC_20×250 mm_5 µm; scCO$_2$/2-propanol+20 mM NH$_3$ 95:5) to give both enantiomers. The absolute stereochemistry at the chiral center of the enantiomerically pure compounds was not determined.

Product IX.1.A (first eluting):
$C_{11}H_{18}N_2O_2$ (M=210.27 g/mol)
Rt (HPLC): 2.58 min (method F)
Product IX.1.B (second eluting):
$C_{11}H_{18}N_2O_2$ (M=210.27 g/mol)
Rt (HPLC): 3.65 min (method F)

Example X

Example X.1

(3S or 3R)-3-Methylpyrrolidine-3-carbonitrile hydrochloride

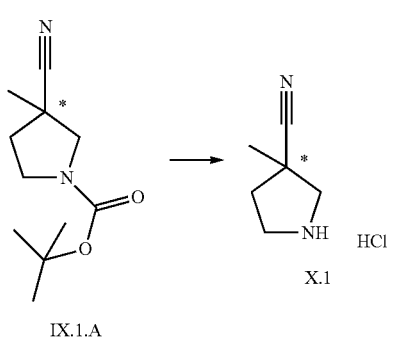

To a mixture of 1.25 g (5.95 mmol) or pure enantiomer tert-butyl 3-cyano-3-methylpyrrolidine-1-carboxylate (example IX.1.A) in 10 mL 1,4-dioxane is added 2.97 mL (11.9 mmol) HCl (4M in 1,4-dioxane) and the mixture is stirred overnight at RT. The obtained precipitate is filtered off, washed with 1,4-dioxane and dried in the open air.

$C_6H_{10}N_2$*HCl (M=146.62 g/mol)
ESI-MS: 111 [M+H]$^+$
Rf (TLC): 0.3 (SiO$_2$, DCM/MeOH/NH$_3$ 9/1/0.1)

The following compounds are prepared according to the general procedure (example X.1) described above:

| Ex. | Starting material | Structure | Reaction conditions | ESI-MS | HPLC Rt [min] (method) |
|---|---|---|---|---|---|
| X.2 | XVIII.1 | (structure) | workup: concentration in vacuo; is used as such in the next step | 194 [M + H]+ | 0.52 (C) |
| X.3 | XXIX.1.A | (structure) | exc. HCl (5M in iPrOH); 2 h; workup: concentration in vacuo; is used as such in the next step | | |
| X.4 | XXVIII.1 | (structure) | exc. HCl; RT; workup: concentration in vacuo; is used as such in the next step | 124 [M + H]+ | 0.21 (C) |

*The stereochemistry at the chiral center of the enantiomerically pure compound was not determined.

Example XI

Example XI.1

6-[(2-Phenylpropan-2-yl)amino]pyridine-3-carboxylic Acid

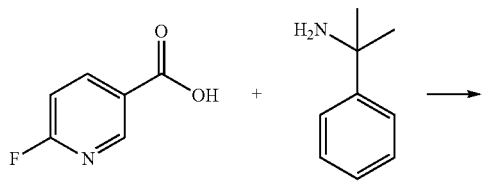

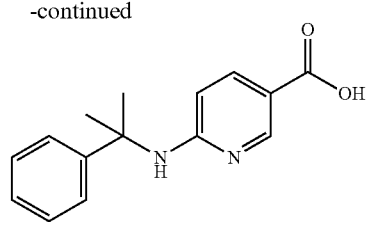

100 mg (0.71 mmol) 6-Fluoropyridine-3-carboxylic acid (CAS No. 403-45-2) and 383 mg (2.83 mmol) cumylamine (CAS No. 585-32-0) are diluted with 2 mL NMP and stirred at 150° C. for 12 h. The reaction mixture is acidified with aq. 4 N hydrogenchloride and purified by HPLC to obtain the product.

$C_{15}H_{16}N_2O_2$ (M=256.30 g/mol)
ESI-MS: 257 [M+H]+
$R_t$ (HPLC): 0.71 min (method A)

The following compounds are prepared according to the general procedure (example XI.1) described above:

| Ex. | Starting material | Structure | Reaction conditions | ESI-MS | HPLC Rt [min] (method) |
|---|---|---|---|---|---|
| XI.2 | (structures) | (structure) | | 269 [M + H]+ | 0.74 (A) |

| Ex. | Starting material | Structure | Reaction conditions | ESI-MS | HPLC Rt [min] (method) |
|---|---|---|---|---|---|
| XI.3 | (6-fluoropyridine-3-carboxylic acid) + (2-(4-chlorophenyl)propan-2-amine) | 6-((2-(4-chlorophenyl)propan-2-yl)amino)nicotinic acid | 3.33 eq amine; purification: HPLC; fractions evaporated and the precipitate filtered, washed with water and dried at 50° C. | 291 [M + H]+ | 0.79 (A) |

Example XII

Example XII.1

(3'S)-[1,3'-Bipyrrolidin]-2-one Hydrochloride

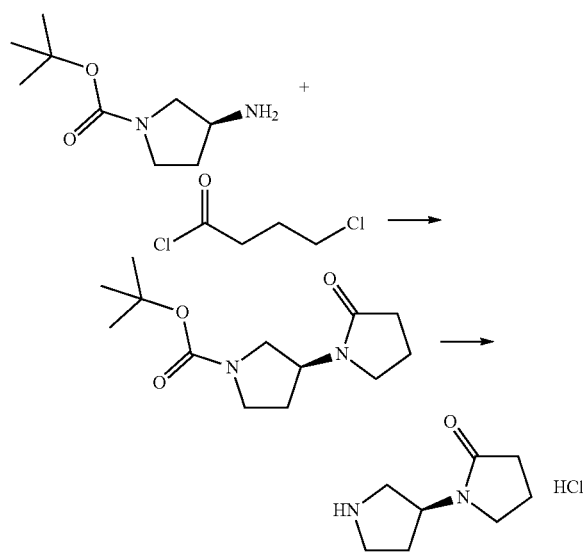

2.00 g (10.74 mmol) tert-Butyl (3S)-3-aminopyrrolidine-1-carboxylate (CAS No. 147081-44-5) is diluted with 20 mL DCM and 4 mL sodium hydroxide (50% in water) and cooled to 0° C. 1.09 mL (9.66 mmol) 4-Chlorobutanoyl chloride (CAS No. 4635-59-0) is dissolved with 10 mL DCM and added dropwise to the reaction mixture. The reaction mixture is stirred for 1 h at 0° C. 3.48 g (5.37 mmol) TBAOH (40% in MeOH) is added to the mixture. The reaction mixture is stirred at RT overnight, diluted with water and the aq. layer is extracted three times with DCM. The pooled organic phases are dried by passing through a PTK and evaporated under reduced pressure. The crude material is purified by column chromatography (silica gel; cyclohexan/EtOAc, 15% to 100%) to give the desired intermediate.

$C_{13}H_{22}N_2O_3$ (M=254.33 g/mol)
ESI-MS: 255 [M+H]+
$R_t$ (HPLC): 0.83 min (method C)

The above mentioned intermediate is dissolved with 2.5 mL 1,4-dioxane and 5.0 mL (20 mmol) hydrogen chloride (4 N in 1,4-dioxane) is added. Some MeOH is also added to solubilize the reaction mixture, then it is stirred at RT overnight and reduced to dryness in vacuo to provide the product.

$C_8H_{14}N_2O$*HCl (M=190.67 g/mol)
ESI-MS: 155 [M+H]+
$R_t$ (HPLC): 0.27 min (method C)

The following compound is prepared according to the general procedure (example XII.1) described above:

| Ex. | Starting materials | Structure | Reaction conditions | ESI-MS | HPLC Rt [min] (method) |
|---|---|---|---|---|---|
| XII.2 | tert-butyl (3S)-3-aminopyrrolidine-1-carboxylate + 2-chloroethyl chloroformate | (S)-3-(2-oxooxazolidin-3-yl)pyrrolidine HCl | | 157 [M + H]+ | 0.17 (C) |

Example XIII

Example XIII.1 tert-Butyl (3S)-3-(1-methylcyclobutaneamido)pyrrolidine-1-carboxylate

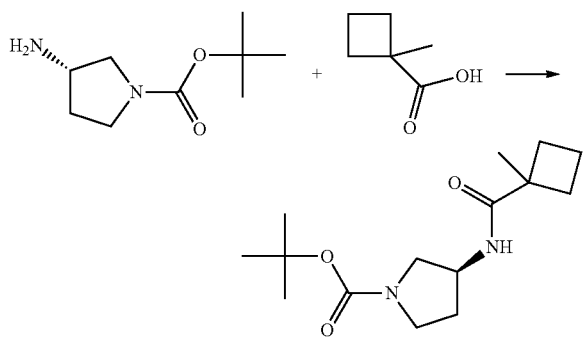

0.55 g (4.83 mmol) 1-Methylcyclobutane-1-carboxylic acid (CAS No. 147081-44-5) is diluted with 7.5 mL DMF and 2.08 mL (12.08 mmol) DIPEA and 1.94 g (6.04 mmol) TBTU are added. After stirring at RT for 30 min, 0.75 g (4.03 mmol) tert-Butyl (3S)-3-aminopyrrolidine-1-carboxylate (CAS No. 147081-44-5) is added and the mixture is stirred at RT overnight. The reaction mixture is diluted with EtOAc, washed once with an aq. NaHCO₃ solution, washed once with an aq. sat. NH4Cl solution and twice with brine. The organic phase is dried with Na₂SO₄ and the solvent is evaporated under reduced pressure to give the product.

$C_{15}H_{26}N_2O_3$ (M=282.38 g/mol)
ESI-MS: 183 [M+H—BOC]⁺
$R_t$ (HPLC): 0.92 min (method C)

Example XIV

Example XIV.1

N,1-Dimethyl-N-[(3S)-pyrrolidin-3-yl]cyclobutane-1-carboxamide hydrochloride

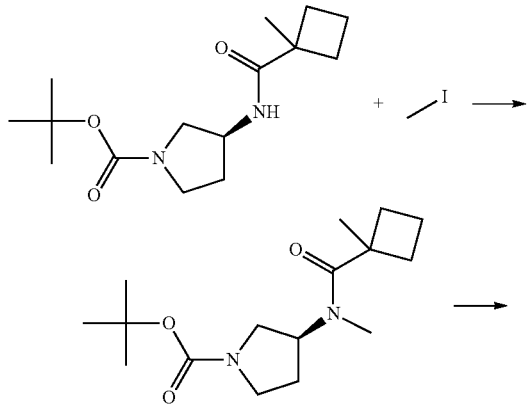

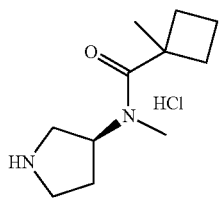

1.37 g (4.85 mmol) tert-Butyl (3S)-3-(1-methylcyclobutaneamido)pyrrolidine-1-carboxylate (ex. XIII 1) is diluted with 10 mL THF and 0.44 mL (7.03 mmol) methyliodide is added. The mixture is cooled to −10° C. and stirred at −10° C. for a short time. After addition of 0.33 g (8.31 mmol) sodium hydride the reaction mixture is stirred at RT overnight. An aq. NaHCO₃ solution and EtOAc are added and the biphasic mixture is vigorously stirred for a short time and then separated. The water phase is extracted twice with EtOAc. The combined organic phases are dried by passing through a PTK and evaporated. The crude material is purified by HPLC to give the desired intermediate.

$C_{16}H_{28}N_2O_3$ (M=296.41 g/mol)
ESI-MS: 297 [M+H]⁺
$R_t$ (HPLC): 0.98 min (method A)

The above mentioned intermediate is dissolved with 4.00 mL MeOH and 4.00 mL (16 mmol) hydrogen chloride (4 N in 1,4-dioxane) and stirred at RT over the weekend. The reaction mixture is reduced to dryness in vacuo to provide the product.

$C_{11}H_{20}N_2O$*HCl (M=232.75 g/mol)
ESI-MS: 197 [M+H]⁺
$R_t$ (HPLC): 0.57 min (method A)

Example XV

Example XV.1

(3S)-1-(6-Fluoropyridine-3-carbonyl)-N-methylpyrrolidin-3-amin trifluoroacetic Acid

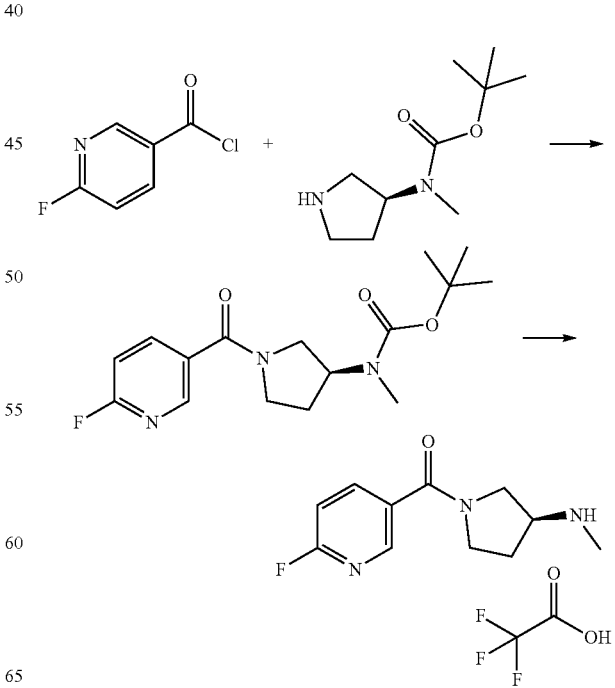

To a ice-cooled mixture of 2.84 g (14.17 mmol) tert-butyl N-methyl-N-[(3S)-pyrrolidin-3-yl]carbamate (CAS No. 169750-01-0) and 9.86 mL (70.83 mmol) TEA in 70 mL DCM is added 2.26 g (14.17 mmol) 6-fluoropyridine-3-carbonyl chloride (CAS No. 65352-94-5) dropwise. The reaction mixture is stirred for 10 min at 0° C. The precipitates are filtered and the filtrate is purified by column chromatography (silica gel, DCM/MeOH, 1% to 10%) to obtain the BOC-protected product.

$C_{16}H_{22}FN_3O_3$ (M=323.36 g/mol)

ESI-MS: 324 [M+H]$^+$

R$_t$ (HPLC): 0.89 min (method C)

The above mentioned intermediate is dissolved with 25 mL DCM, then 5 mL TFA is added and it is stirred at RT overnight. The reaction mixture is evaporated under reduced pressure to give the product.

$C_{11}H_{14}FN_3O*C_2HF_3O_2$ (M=337.27 g/mol)

ESI-MS: 224 [M+H]$^+$

R$_t$ (HPLC): 0.61 min (method C)

Example XVI

Example XVI.1

N-[(3S)-1-(6-Fluoropyridine-3-carbonyl)pyrrolidin-3-yl]-N,1-dimethylcyclobutane-1-carboxamide

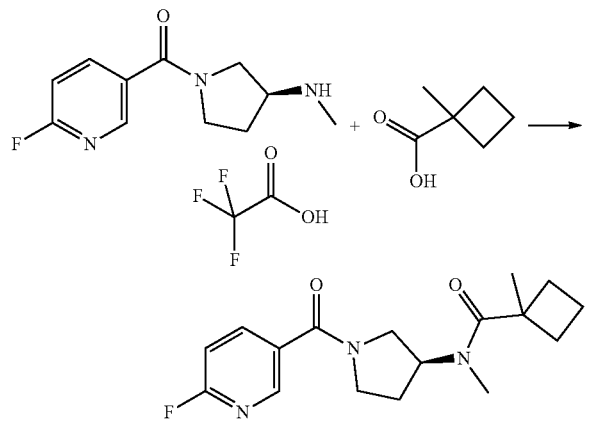

1.1 g (3.26 mmol) (3S)-1-(6-Fluoropyridine-3-carbonyl)-N-methylpyrrolidin-3-amine trifluoroacetic acid (ex. XV.1), 0.45 g (3.91 mmol) 1-methylcyclobutane-1-carboxylic acid (CAS No. 32936-76-8) and 2.79 mL (16.30 mmol) DIPEA are diluted with 10 mL DMF and 1.86 g (4.89 mmol) HATU is added. The reaction mixture is stirred at RT for 10 min, then diluted with DCM and washed once with a sat. NaHCO$_3$ solution, washed once with a sat. NH4Cl solution and brine. The organic phase is dried with Na$_2$SO$_4$ and reduced to dryness in vacuo. The crude material is purified by column chromatography (silica gel, DCM/MeOH, 1% to 10%) to provide the product.

$C_{17}H_{22}FN_3O_2$ (M=319.37 g/mol)

ESI-MS: 320 [M+H]$^+$

R$_t$ (HPLC): 0.80 min (method C)

Example XVII

Example XVII.1

N-Methyl-N-[(3S)-pyrrolidin-3-yl]pyrimidin-2-amine hydrochloride

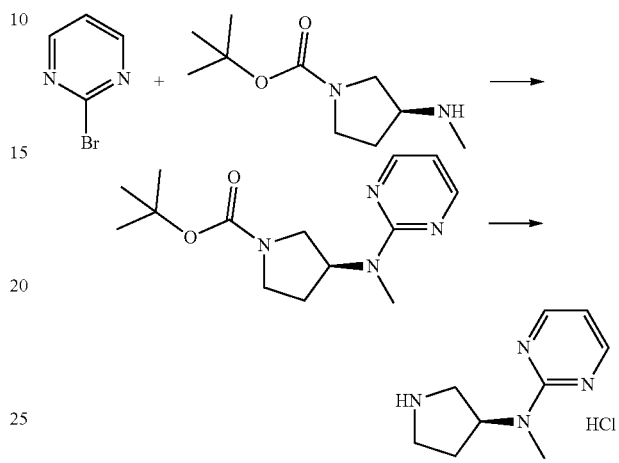

1.00 g (6.29 mmol) 2-Bromopyrimidine (CAS No. 4595-60-2), 1.51 g (7.55 mmol) tert-butyl (3S)-3-(methylamino)pyrrolidine-1-carboxylate (CAS No. 147081-59-2) and 3.81 mL (22.01 mmol) DIPEA are diluted with 10 mL DMF and stirred at 120° C. for 2 h. The reaction mixture is concentrated under reduced pressure and the residue is purified by column chromatography (silica gel, DCM/MeOH, 0% to 4%) to provide the BOC-protected product.

$C_{14}H_{22}N_4O_2$ (M=278.35 g/mol)

ESI-MS: 279 [M+H]$^+$

R$_t$ (HPLC): 0.87 min (method A)

The above mentioned intermediate is dissolved with 10 mL MeOH, 4 mL HCl (4 N in 1,4-dioxane) is added and it is stirred at RT overnight. The reaction mixture is evaporated under reduced pressure to give the product.

$C_9H_{14}FN_4*HCl$ (M=214.70 g/mol)

ESI-MS: 179 [M+H]$^+$

R$_t$ (HPLC): 0.15 min (method A)

Example XVIII

Example XVIII.1 tert-Butyl (3S)-3-(N-methyl1-cyanocyclopropaneamido)pyrrolidine-1-carboxylate

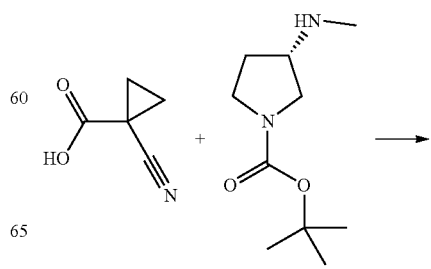

-continued

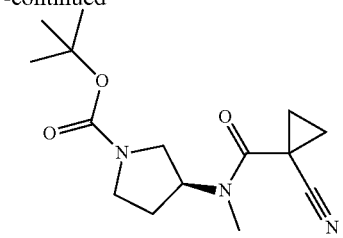

150 mg (1.35 mmol) 1-Cyanocyclopropane-1-carboxylic acid (CAS No. 6914-79-0), 300 mg (1.5 mmol) tert-butyl (3S)-3-(methylamino)pyrrolidine-1-carboxylate (CAS No. 147081-59-2), 500 mg (1.56 mmol) TBTU and 0.6 mL (3.47 mmol) DIPEA are diluted with 4 mL DMF and stirred at RT for 2 h. The reaction mixture is filtered through a microdisk syringe filter and purified by HPLC to provide the product.
$C_{15}H_{23}N_3O_3$ (M=293.36 g/mol)
ESI-MS: 294 [M+H]$^+$
R$_t$ (HPLC): 0.90 min (method C)

Example XIX

Example XIX.1

1-(Pyrimidin-5-yl)cyclopropan-1-amine Trifluoroacetate

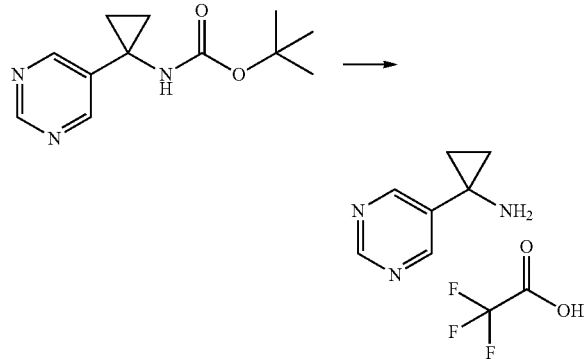

1-(Pyrimidin-5-yl)cyclopropan-1-amine trifluoroacetate is prepared according to the procedure described in WO 2016193844.

Example XX

Example XX.1

Methyl 6-({5H,6H,7H-cyclopenta[b]pyridin-5-yl}amino)pyridine-3-carboxylate

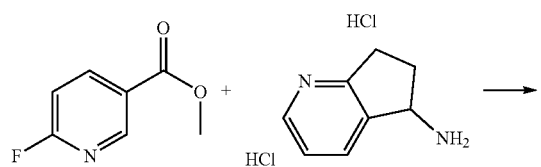

-continued

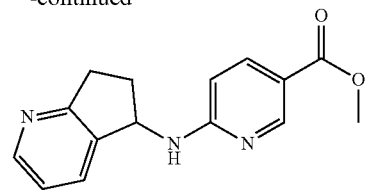

0.37 g (2.41 mmol) Methyl 6-fluoropyridine-3-carboxylate (CAS No. 1427-06-1), 0.50 g (2.41 mmol) 5H,6H,7H-cyclopenta[b]pyridin-5-amine dihydrochloride (CAS No. 1187930-17-1), 2.48 mL (14.49 mmol) DIPEA and 5 mL DMSO are stirred at 120° C. for 1 h. The reaction mixture is diluted with EtOAc and washed twice with an aq. NaHCO$_3$ solution. The organic phase is dried with Na$_2$SO$_4$, filtered and reduced in vacuo to give the product.
$C_{15}H_{15}N_3O_2$ (M=269.30 g/mol)
ESI-MS: 270 [M+H]$^+$
R$_t$ (HPLC): 0.54 min (method A)

Example XXI

Example XXI.1.A and Example XXI.1.B

Methyl 6-{[(5S)-5H,6H,7H-cyclopenta[b]pyridin-5-yl]amino}pyridine-3-carboxylate Methyl 6-{[(5R)-5H,6H,7H-cyclopenta[b]pyridin-5-yl]amino}pyridine-3-carboxylate

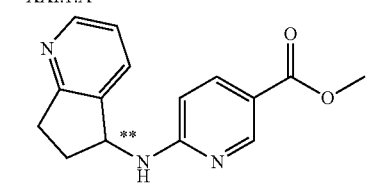

0.65 g (2.41 mmol) Methyl 6-({5H,6H,7H-cyclopenta[b]pyridin-5-yl}amino)pyridine-3-carboxylate (ex. XX.1) is purified by chiral SFC (Lux® Amylose-22.1×250 mm_5 µm; scCO$_2$/MeOH+20 mM NH$_3$ 75:25) to give both enantiomers. The absolute stereochemistry at the chiral center of the enantiomerically pure compounds was not determined.
Product XXI.1.A (first eluting):
$C_{15}H_{15}N_3O_2$ (M=269.30 g/mol)
Rt (HPLC): 2.32 min (method H)
Product XXI.1.B (second eluting):
$C_{15}H_{15}N_3O_2$ (M=269.30 g/mol)
Rt (HPLC): 3.31 min (method H)

Example XXII

Example XXII.1

6-{[5H,6H,7H-Cyclopenta[b]pyridin-5-yl]amino}pyridine-3-carboxylic acid hydrochloride

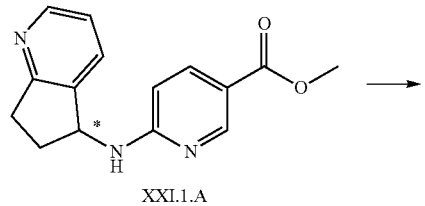

XXI.1.A

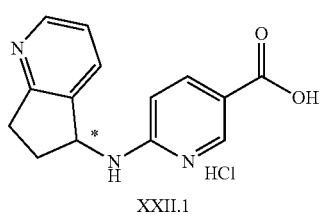

XXII.1

30.0 mg (0.11 mmol) Methyl 6-{[5H,6H,7H-cyclopenta[b]pyridin-5-yl]amino}pyridine-3-carboxylate (ex. XXI.1.A) in 1 mL 6N hydrogenchloride is stirred at 80° C. for 1 h. The reaction mixture is evaporated under reduced pressure to provide the product.

$C_{14}H_{13}N_3O_2$*HCl (M=291.73 g/mol)
ESI-MS: 256 [M+H]$^+$
$R_t$ (HPLC): 0.09 min (method A)

The following compound is prepared according to the general procedure (example XXII.1) described above:

Example XXIII

Example XXIII.1

6-{[(1S)-1-Phenylethyl]amino}pyridine-3-carboxylic Acid

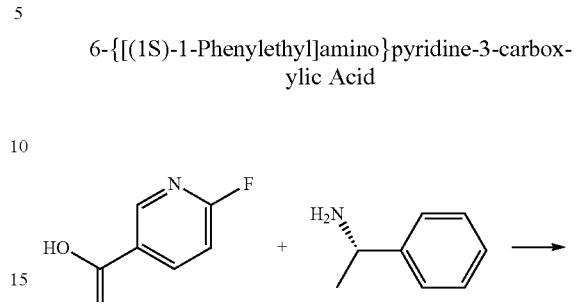

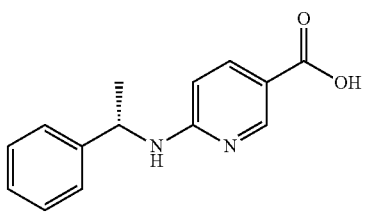

250 mg (1.77 mmol) 6-Fluoropyridine-3-carboxylic acid (CAS No. 403-45-2), 429 mg (3.54 mmol) (1S)-1-phenylethan-1-amine (CAS No. 2627-86-3) and 980 mg (7.09 mmol) potassium carbonate in 2 mL DMSO are stirred at 150° C. overnight. The reaction mixture is filtered through a microdisk syringe filter and purified by HPLC to obtain the product.

$C_{14}H_{14}N_2O_2$ (M=242.27 g/mol)
ESI-MS: 243 [M+H]$^+$
$R_t$ (HPLC): 0.71 min (method I)

The following compound is prepared according to the general procedure (example XXIII.1) described above:

| Ex. | Starting materials | Structure | Reaction conditions | ESI-MS | HPLC Rt [min] (method) |
|---|---|---|---|---|---|
| XXII.2 | XXI.1.B | (structure shown) | 2 h | 256 [M + H]$^+$ | 0.09 (A) |

* and **: The stereochemistry at the chiral center of the enantiomerically pure compound was not determined.

| Ex. | Starting materials | Structure | Reaction conditions | ESI-MS | HPLC Rt [min] (method) |
|---|---|---|---|---|---|
| XXIII.2 | 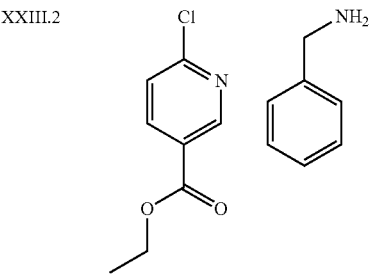 | 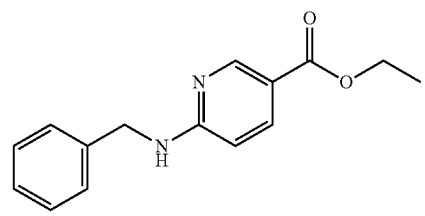 [SMILES: CCOC(=O)c1ccc(NCc2ccccc2)nc1] | 3 eq K₂CO₃; 2 h; in microwave; workup: poured into aq. Na₂CO₃ solution; precipitate filtered | 257 [M + H]⁺ | |

Example XXIV

Example XXIV.1

3-[(1E)-1-{[(S)-2-methylpropane-2-sulfinyl]imino}ethyl]benzene-1-sulfonamide

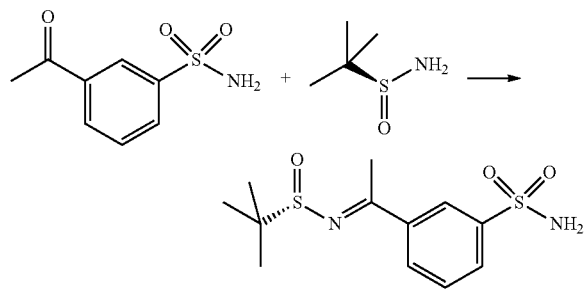

0.20 g (1.00 mmol) 3-Acetylbenzene-1-sulfonamide (CAS No. 35203-88-4), 0.49 g (4.02 mmol) (S)-2-methylpropane-2-sulfinamide (CAS No. 146374-27-8) and 1.95 mL (10.04 mmol) titanium (IV) isopropoxide in 2 mL THF are stirred at 80° C. overnight. The reaction mixture is cooled and diluted with 10 mL brine and 20 mL water. The precipitate is filtered through celite and washed with EtOAc. The organic phase is separated and washed with brine, dried with Na₂SO₄ and reduced to dryness in vacuo to provide the product.

$C_{12}H_{18}N_2O_3S_2$ (M=302.42 g/mol)

ESI-MS: 303 [M+H]⁺

$R_t$ (HPLC): 0.68 min (method C)

The following compounds are prepared according to the general procedure (example XXIV.1) described above:

| Ex. | Starting material | Structure | Reaction conditions | ES-MS | HPLC Rt [min] (method) |
|---|---|---|---|---|---|
| XXIV.2 | 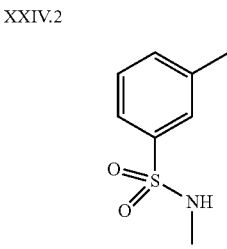 | 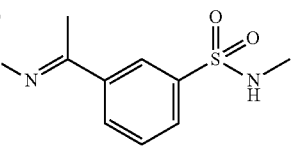 | 5 eq Ti(iPrO)₄; 30 min; workup: drying the organic phase with PTK | 317 [M + H]⁺ | 0.87 (A) |
| XXIV.3 | 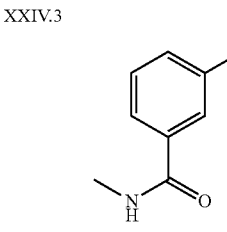 | 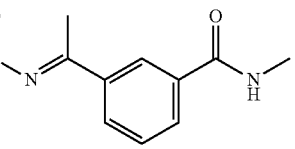 | 2.0 eq sulfinamide; 2.5 eq Ti(iPrO)₄; 30 min; workup: drying the organic phase with PTK | 281 [M + H]⁺ | 0.82 (A) |

| Ex. | Starting material | Structure | Reaction conditions | ES-MS | HPLC Rt [min] (method) |
|---|---|---|---|---|---|
| XXIV.4 | | 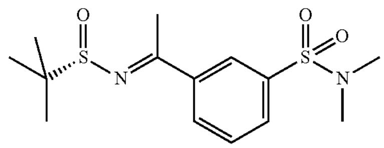 [SMILES: C/C(=N\[S@@](=O)C(C)(C)C)c1cccc(S(=O)(=O)N(C)C)c1] | 2.5 eq sulfinamide; 3.0 eq Ti(iPrO)$_4$; 30 min | 331 [M + H]$^+$ | 0.92 (A) |

Example XXV

Example XXV.1

3-[(1S)-1-aminoethyl]benzene-1-sulfonamide hydrochlorid

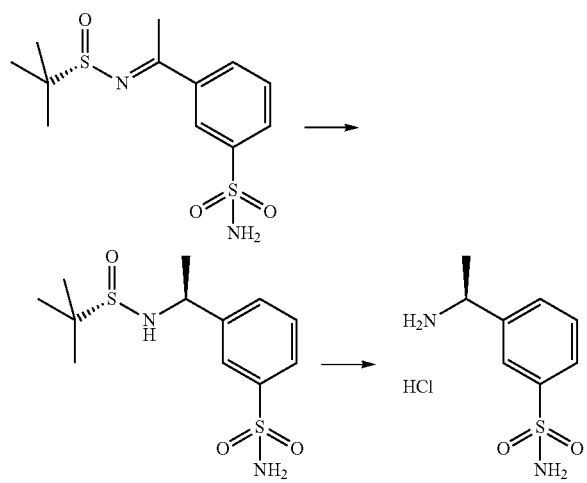

0.57 g (0.94 mmol) 3-[(1E)-{[(S)-2-Methylpropane-2-sulfinyl]imino}ethyl]benzene-1-sulfonamide (ex. XXIV.1) is dissolved with 5 mL THF, 0.1 mL water is added and the mixture is cooled to −50° C. To the cooled mixture is added 0.11 g (2.83 mmol) sodium borohydride. The reaction mixture is warmed to RT, diluted with an aq. sat. ammonium chloride solution and the organic phase is separated, dried and evaporated to give the protected product.

$C_{12}H_{20}N_2O_3S2$ (M=304.43 g/mol)
ESI-MS: 305 [M+H]$^+$
$R_t$ (HPLC): 0.71 min (method C)

The above mentioned intermediate is dissolved with 10 mL THF and cooled to 0° C. The reaction mixture is treated with 2.0 mL (8.00 mmol) hydrogenchloride (4 N in 1,4-dioxane) and warmed to RT. The precipitate is filtered to give the product.

$C_8H_{12}N_2O_2S*HCl$ (M=236.72 g/mol)
ESI-MS: 201 [M+H]$^+$
$R_t$ (HPLC): 0.28 min (method C)

The following compounds are prepared according to the general procedure (example XXV.1) described above:

| Ex. | Starting material | Structure | Reaction conditions | ESI-MS | HPLC Rt [min] (method) |
|---|---|---|---|---|---|
| XXV.2 | XXIV.2 | 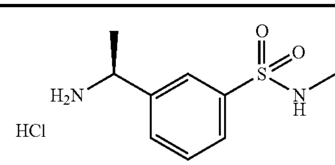 | step 1: dry ice-acetone-bath step 2: 3.4 eq HCl | 215 [M + H]$^+$ | 0.27 (A) |
| XXV.3 | XXIV.3 | 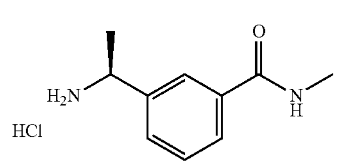 | step 1: dry ice-acetone- bath; drying of the organic phase with PTK step 2: exc. HCl; reaction mixture concentrated in vacuo | 179 [M + H]$^+$ | 0.60 (A) |

| Ex. | Starting material | Structure | Reaction conditions | ESI-MS | HPLC Rt [min] (method) |
|---|---|---|---|---|---|
| XXV.4 | XXIV.4 | 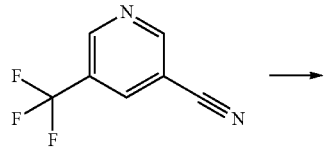 Cl—H | step 1: dry ice-acetone-bath step 2: evaporation | 229 [M + H]+ | 0.56 (A) |

Example XXVI

Example XXVI.1

1-[5-(trifluoromethyl)pyridin-3-yl]cyclopropan-1-amine trifluoroacetate

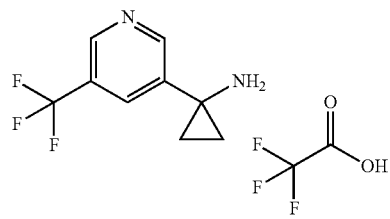

688 mg (4.00 mmol) 5-(Trifluoromethyl)pyridine-3-carbonitrile (CAS No. 951624-83-2) is diluted with 30 mL diethylether. At RT, 1.37 mL (4.67 mmol) Ti(iPrO)$_4$ is added dropwise. To the reaction mixture is added 2.95 mL (8.84 mmol) ethylmagnesiumbromid (3 M in diethylether) and the temperature is held between 15° C. and 20° C. The mixture is stirred at RT for 30 min and then treated with 1.26 mL (9.97 mmol) borotrifluoride diethyletherate under temperature control (18° C.-22° C.). The reaction mixture is stirred at RT, cooled and 20 mL 2 N sodium hydroxide is added. It is stirred at RT for 2 h. The reaction mixture is filtered through Celite and washed with diethylether. The organic phase is separated and the water phase is extracted twice with diethylether. The combined organic phases are evaporated. The residue is taken up with ACN/water and purified by HPLC to obtain the product.

$C_9H_9N_2F_3 * C_2H_1O_2F_3$ (M=316.20 g/mol)

ESI-MS: 203 [M+H]+

R$_t$ (HPLC): 0.49 min (method J)

Example XXVII

Example XXVII.1 tert-Butyl N-[(2E)-2-[(dimethylamino)methylidene]-3-oxocyclopentyl]carbamate

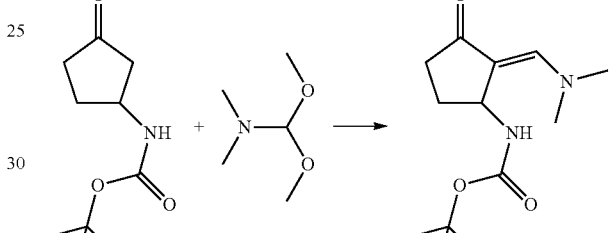

A mixture of 2.00 g tert-butyl N-(3-oxocyclopentyl)carbamate (CAS No. 847416-99-3) in 20 mL N,N-dimethylformamide dimethylacetal is stirred at 80° C. for 12 h. The reaction mixture is evaporated under reduced pressure. The residue is purified by column chromatography (silica gel, PE/EtOAc, 15% to 50%) to obtain the desired product.

$C_{13}H_{22}N_2O_3$ (M=254.33 g/mol)

R$_f$ (TLC): 0.50 (silica gel; DCM/MeOH (10:1))

Example XXVIII

Example XXVIII.1 tert-Butyl N-{1H,4H,5H,6H-cyclopenta[c]pyrazol-4-yl}carbamate

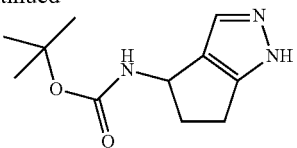

To a stirred solution of 1.00 g (3.93 mmol) tert-butyl N-[(2E)-2-[(dimethylamino)methylidene]-3-oxocyclopentyl]carbamate (ex. XXVII.1) in 12.5 mL MeOH is added 0.30 g (9.36 mmol) hydrazine hydrate. The resulting mixture is heated at 80° C. for 2 h. Upon reaction completion, the mixture is evaporated and dried, then diluted with water and EtOAc. The organic layer is separated, dried over $Na_2SO_4$ and concentrated under reduced pressure. The residue is purified by column chromatography (silica gel, hexane/EtOAc, 20% to 30%) to afford the product.

$C_{11}H_{17}N_3O_2$ (M=223.27 g/mol)
$R_f$ (TLC): 0.30 (silica gel; DCM/MeOH (10:1))

Example XXIX

Example XXIX.1.A and Example XXIX.1.B tert-Butyl N-[(4S)-1H,4H,5H,6H-cyclopenta[c]pyrazol-4-yl]carbamate tert-Butyl N-[(4R)-1H,4H,5H,6H-cyclopenta[c]pyrazol-4-yl]carbamate

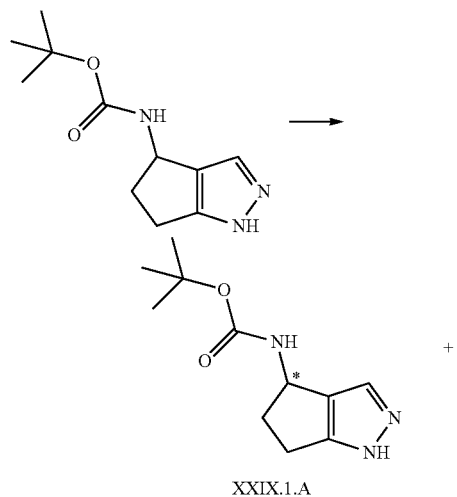

1.50 g (0.01 mol) tert-Butyl N-{1H,4H,5H,6H-cyclopenta[c]pyrazol-4-yl}carbamate (ex. XXVIII.1) is purified by chiral SFC (Lux® Cellulose-4_21.2×250 mm_5 μm; scCO₂/MeOH+20 mM NH₃ 85:15) to give both enantiomers. The absolute stereochemistry at the chiral center of the enantiomerically pure compounds was not determined.

Product XXIX.1.A (first eluting):
$C_{11}H_{17}N_3O_2$ (M=223.27 g/mol)
Rt (HPLC): 2.37 min (method K)
Product XXIX.1.B (second eluting):
$C_{11}H_{17}N_3O_2$ (M=223.27 g/mol)
Rt (HPLC): 3.07 min (method K)

Example XXX

Example XXX.1

Methyl 3-[1-({5-[(3S)-3-(N-methylacetamido)pyrrolidine-1-carbonyl]pyridin-2-yl}amino)ethyl]benzoate

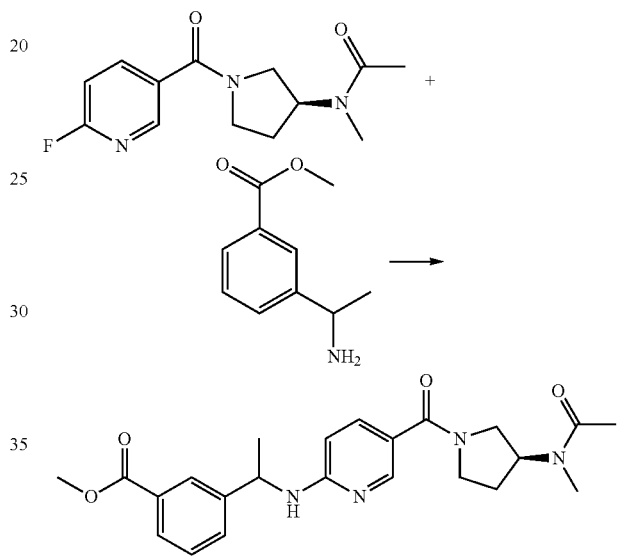

A mixture of 100 mg (0.38 mmol) N-[(3S)-1-(6-fluoropyridine-3-carbonyl)pyrrolidin-3-yl]-N-methylacetamide (ex. I.1), 100 mg (0.56 mmol) methyl 3-(1-aminoethyl)benzoate (CAS No. 153994-69-5) and 0.39 mL (2.26 mmol) DIPEA in 1.5 mL DMSO are stirred at 120° C. overnight. The reaction mixture is purified by HPLC to obtain the product.

$C_{23}H_{28}N_4O_4$ (M=424.49 g/mol)
ESI-MS: 425 [M+H]⁺
$R_t$ (HPLC): 0.84 min (method C)

Example XXXI

Example XXXI.1

3-[1-({5-[(3 S)-3-(N-Methylacetamido)pyrrolidine-1-carbonyl]pyridin-2-yl}amino)ethyl]benzoic Acid

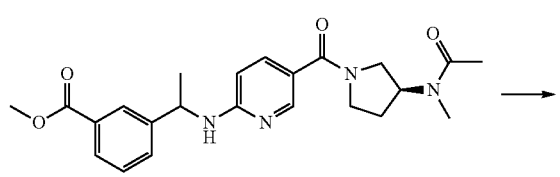

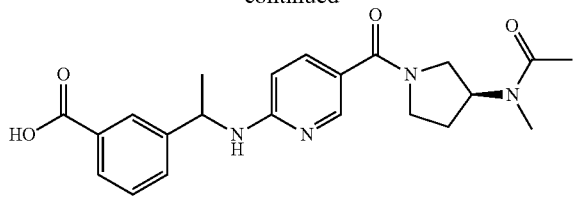

A mixture of 42.0 mg (0.10 mmol) methyl 3-[1-({5-[(3S)-3-(N-methylacetamido)pyrrolidine-1-carbonyl]pyridin-2-yl}amino)ethyl]benzoate (ex. XXX.1) and 0.15 mL (0.30 mmol) lithium hydroxide (2 N in water) in 1 mL THF ist stirred at 70° C. for 1 h. The reaction mixture is concentrated under reduced pressure to obtain the product.

$C_{22}H_{26}N_4O_4$ (M=410.47 g/mol)

The following compound is prepared according to the general procedure (example XXXI.1) described above:

| Ex. | Starting material | Structure | Reaction conditions | ESI-MS | HPLC Rt [min] (method) |
|---|---|---|---|---|---|
| XXXI.2 | XXIII.2 | 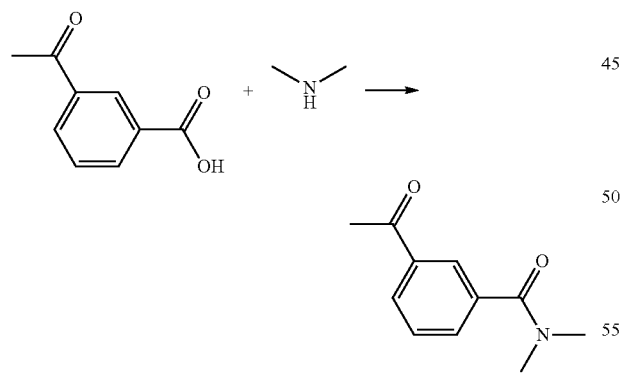 | 1.7N aq. LiOH; 60° C.; 1 h; workup: poured into water, acidified with HCl and product filtered | 229 [M + H]$^+$ | |

Example XXXII

Example XXXII.1

3-Acetyl-N,N-dimethylbenzamide

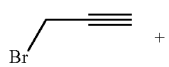

1.34 mL (2.68 mmol) Dimethylamine solution (2 N in THF) and 0.40 g (2.44 mmol) 3-acetylbenzoic acid (CAS No. 586-42-5) are diluted with DMF (3.0 mL), then 1.46 mL (8.53 mmol) DIPEA is added and the mixture is stirred at RT for two minutes. 1.39 g (3.66 mmol) HATU is added to the reaction mixture and it is stirred at RT for 2 h. A sat. aq. NaHCO$_3$ solution is added to the mixture and the water phase is extracted twice with DCM. The organic phases are combined, dried by passing through a PTK and concentrated in vacuo. The residue is dissolved with minimum MeOH, filtered through a microdisk syringe filter and purified by HPLC to obtain the product.

$C_{11}H_{13}NO_2$ (M=191.23 g/mol)
ESI-MS: 192 [M+H]$^+$
R$_t$ (HPLC): 0.67 min (method C)

Example XXXIII

Example XXXIII.1 tert-Butyl N-[(tert-butoxy)carbonyl]-N-(prop-2-yn-1-yl)carbamate

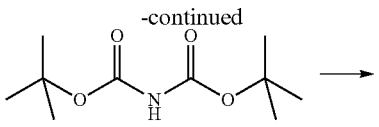

25.0 g (113 mmol) tert-Butyl N-[(tert-butoxy)carbonyl]carbamate (CAS No. 51779-32-9) is diluted with 100 mL DMF and treated with 35.0 g (253 mmol) K2CO3. The mixture is cooled to 0° C. and 14.0 mL (130 mmol) 3-Bromoprop-1-yne (80% in toluene; CAS No. 106-96-7) is added dropwise. The reaction mixture is stirred at RT for 2 h and some additional 3-Bromoprop-1-yne is added to complete reaction. After stirring at RT for 1 h the reaction mixture is diluted with DCM and the organic phase is washed once with a sat. aq. NaHCO$_3$ solution and washed once with brine. The organic phase is concentrated under reduced pressure and the residue is purified by MPLC (SiO$_2$, DCM/MeOH 99:1) to provide the product.

$C_{13}H_{21}NO_4$ (M=255.31 g/mol)

R$_f$ (TLC): 0.82 (SiO$_2$, DCM/MeOH 95:05)

Example XXXIV

Example XXXIV.1 tert-Butyl N-[(tert-butoxy)carbonyl]-N-(4-cyclopropyl-4-oxobut-2-yn-1-yl)carbamate

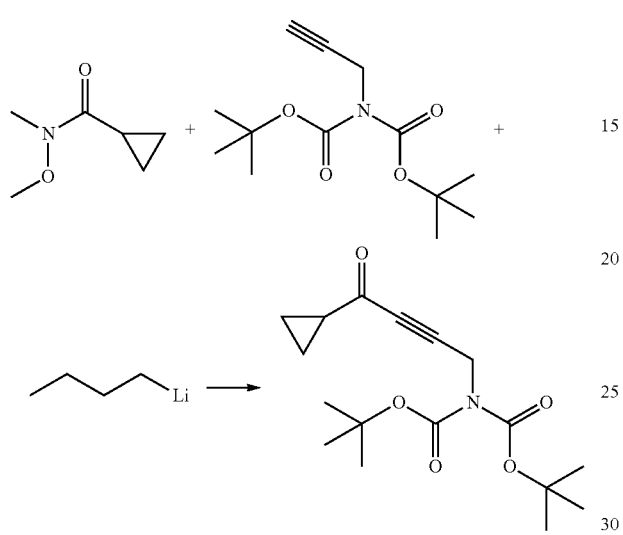

Under an inert Argon atmosphere, 15.2 g (59.5 mmol) tert-Butyl N-[(tert-butoxy)carbonyl]-N-(prop-2-yn-1-yl)carbamate (ex. XXXIII.1) is diluted with THF (200 mL) and cooled to −78° C. To this solution is added dropwise 45.0 mL (70.0 mmol) n-butyllithium (1.60 M in hexane). The reaction mixture is stirred at −78° C. for 30 min. This solution is then slowly transferred to a precooled (−78° C.) solution containing 7.00 g (50.0 mmol) N-methoxy-N-methylcyclopropanecarboxamide (CAS No. 147356-78-3) in THF (50 mL). The reaction mixture is slowly warmed to 0° C. and stirred at this temperature for 3 h. The solution is then acidified with 2 N hydrogenchloride at 0° C. and diluted with EtOAc. The organic phase is separated, washed once with brine, dried with $Na_2SO_4$ and concentrated under reduced pressure to give the product.

$C_{17}H_{25}NO_5$ (M=323.38 g/mol)

Example XXXV

Example XXXV.1

1-(3-Cyclopropyl-1-methyl-1H-pyrazol-5-yl)methanamine hydrochloride

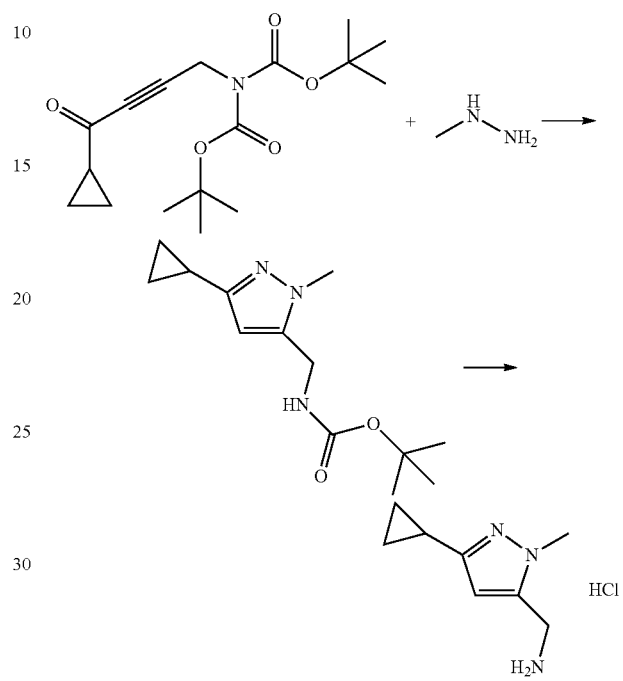

21.0 g (52.0 mmol) tert-Butyl N-[(tert-butoxy)carbonyl]-N-(4-cyclopropyl-4-oxobut-2-yn-1-yl)carbamate (ex. XXXIV.1) and 2.87 g (62.3 mmol) methylhydrazine are diluted with 100 mL EtOH and stirred in a microwave at 130° C. for 12 min. The solvent is evaporated in vacuo and the residue is purified by MPLC (silica gel, eluent: DCM/MeOH). The BOC-protected product is diluted with EtOH (20 mL) and treated with 155 mL (155 mmol) of 1N hydrogenchloride solution in diethylether. The reaction mixture is stirred at RT overnight. The precipitate is filtered, washed with diethylether and dried in vacuo to give the product.

$C_8H_{13}N_3$*HCl (M=187.67 g/mol)
ESI-MS: 152 [M+H]$^+$
$R_t$ (HPLC): 0.32 min (method C)

The following compound is prepared according to the general procedure (example XXXV.1) described above:

| Ex. | Starting materials | Structure | Reaction conditions | ESI-MS | HPLC Rt [min] (method) |
|---|---|---|---|---|---|
| XXXV.2 | XXXXI.1 $H_2N-NH_2 \cdot H_2O$ | (structure) | 2 eq hydrazine; 70° C. overnight under atmospheric condition; purification: HPLC | 254 [M + H]$^+$ | |

Example XXXXI

Example XXXXI.1 tert-Butyl N-(6-methyl-2-oxohept-3-yn-1-yl)carbamate

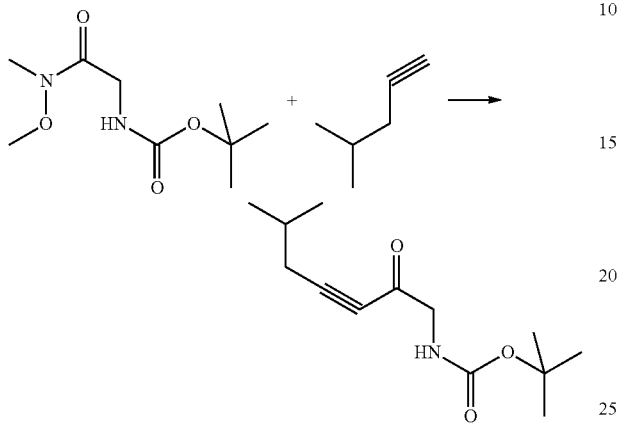

1.50 g (6.74 mmol) tert-butyl N-{[methoxy(methyl)carbamoyl]-methyl}carbamate (CAS No. 121505-93-9) in 50 mL THF is cooled to −70° C. and 2.00 mL (6.00 mmol) chloromethylmagnesium solution (3.0 M in THF) is added dropwise. This suspension is stirred at −70° C. for 90 min. In a separate flask is prepared 0.79 mL (6.74 mmol) 4-methylpent-1-yne (CAS No. 7154-75-8) in THF (50 mL) and cooled to −70° C. before slowly adding 7.60 mL (12.16 mmol) n-buthyllithium solution (1.60 M in n-hexane). This clear solution is stirred at −70° C. for 90 min, then it is slowly transferred to the previous mixture at −70° C. The white suspension is further stirred at this temperature for 1 h, then afterwards warmed to RT. The resulting clear solution is cooled again with an ice bath, treated with 17 mL 1 N hydrogenchloride and let slowly warmed to RT. The water phase is extracted with EtOAc, combined organic layers are dried with Na$_2$SO$_4$ and concentrated under reduced pressure to provide the product.

C$_{13}$H$_{21}$NO$_3$ (M=239.31 g/mol)

R$_f$ (SiO$_2$, DCM/MeOH 95:05) 0.82

Example XXXXII

Example XXXXII.1

1-[3-(2-Methylpropyl)-1H-pyrazol-5-yl]methanamine hydrochloride

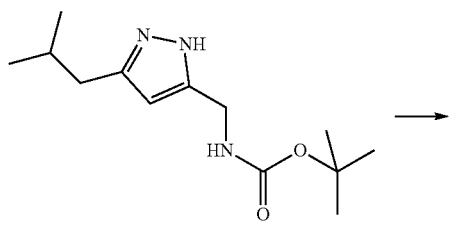

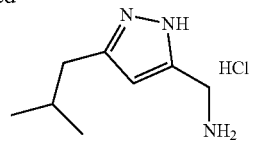

0.55 g (2.17 mmol) tert-Butyl N-{[3-(2-methylpropyl)-1H-pyrazol-5-yl]methyl}carb-amate (ex. XXXV.2) is suspended in 10 mL water, cooled in ice bath and treated with 5 mL conc. hydrogenchloride. The reaction mixture is stirred at RT for 3 h. Upon reaction completion, the solution is frozen and lyophilized to obtain the given product.

C$_8$H$_{15}$N$_3$*HCl (M=189.69 g/mol)

ESI-MS: 154 [M+H]$^+$

Preparation of Final Compounds

Example 1

Example 1.1 (General Route)

N-[(3S)-1-(6-{[(3-Cyanophenyl)methyl]amino}pyridine-3-carbonyl)pyrrolidin-3-yl]-N-methylacetamide

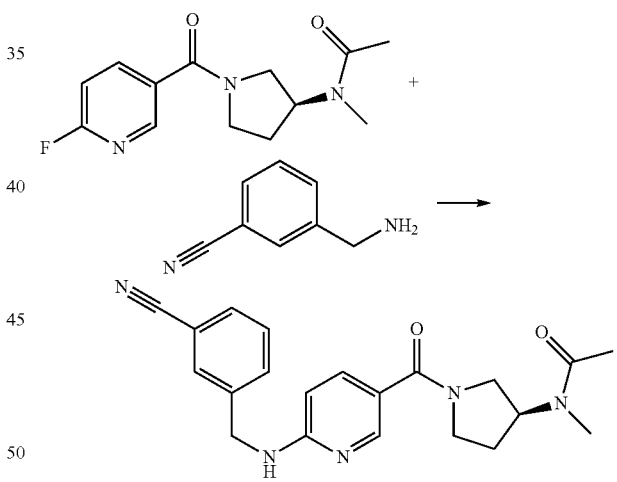

A mixture of 100 mg (0.19 mmol) N-[(3S)-1-(6-fluoropyridine-3-carbonyl)pyrrolidin-3-yl]-N-methylacetamide (ex. I.1), 50 mg (0.38 mmol) 3-aminomethylbenzonitril (CAS No. 10406-24-3) and 0.16 mL (0.95 mmol) DIPEA in 1 mL DMSO are stirred at 120° C. overnight. The reaction mixture is diluted with MeOH, filtered through a microdisk syringe filter and purified by preparative HPLC to give the product

C$_{21}$H$_{23}$N$_5$O$_2$ (M=377.44)

ESI-MS: 378 [M+H]$^+$

R$_t$ (HPLC) 0.77 min (method A)

The following compounds are prepared according to the general procedure (example 1.1) described above:

| Ex. | Starting materials | Structure | Reaction conditions | ESI-MS | HPLC Rt [min] (method) |
|---|---|---|---|---|---|
| 1.2 | I.1 | 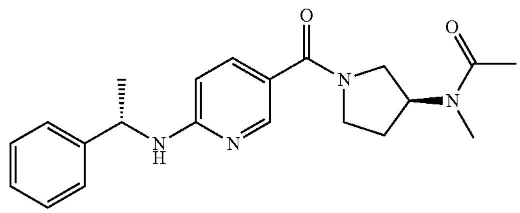 [SMILES: CC(=O)N(C)[C@H]1CCN(C(=O)c2ccc(N[C@@H](C)c3ccccc3)nc2)C1] | | 367 [M + H]⁺ | 0.73 (A) |
| 1.3 | I.1 | 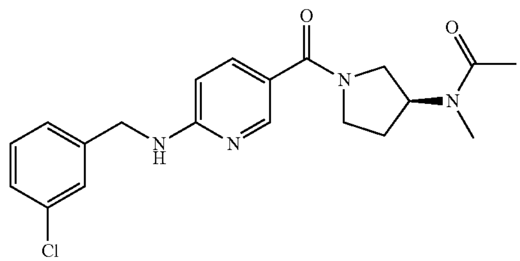 [SMILES: CC(=O)N(C)[C@H]1CCN(C(=O)c2ccc(NCc3cccc(Cl)c3)nc2)C1] | 4 eq of amine; 3.5 of DIPEA | 387 [M + H]⁺ | 0.76 (B) |
| 1.4 | I.1 | 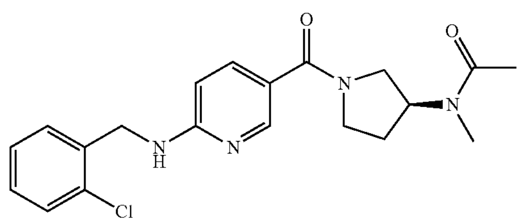 [SMILES: CC(=O)N(C)[C@H]1CCN(C(=O)c2ccc(NCc3ccccc3Cl)nc2)C1] | 4 eq of amine; 3.5 of DIPEA | 387 [M + H]⁺ | 0.75 (B) |
| 1.5 | III.1 | 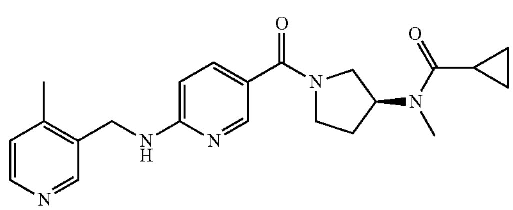 | | 394 [M + H]⁺ | 0.77 (C) |
| 1.6 | I.1 | 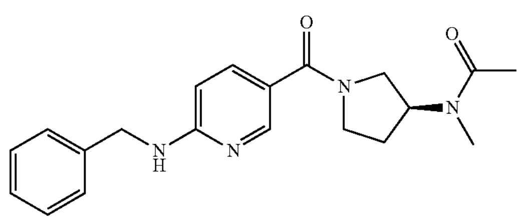 [SMILES: CC(=O)N(C)[C@H]1CCN(C(=O)c2ccc(NCc3ccccc3)nc2)C1] | 130° C.; 15 h | 353 [M + H]⁺ | 0.80 (C) |
| 1.7 | XVI.1 | 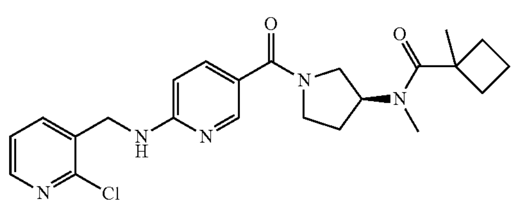 [SMILES: CN(C(=O)C1(C)CCC1)[C@H]1CCN(C(=O)c2ccc(NCc3cccnc3Cl)nc2)C1] | | 442 [M + H]⁺ | 0.86 (C) |
| 1.8 | III.1 | 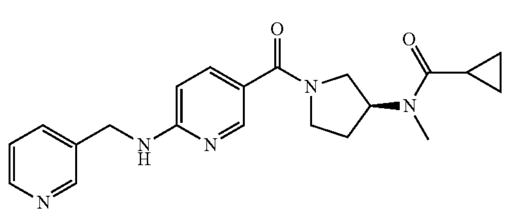 [SMILES: CN(C(=O)C1CC1)[C@H]1CCN(C(=O)c2ccc(NCc3cccnc3)nc2)C1] | | 380 [M + H]⁺ | 0.56 (A) |

-continued

| Ex. | Starting materials | | Structure | Reaction conditions | ESI-MS | HPLC Rt [min] (method) |
|---|---|---|---|---|---|---|
| 1.9 | XVI.1 | HCl, (3-methylpyridin-4-yl)methanamine | 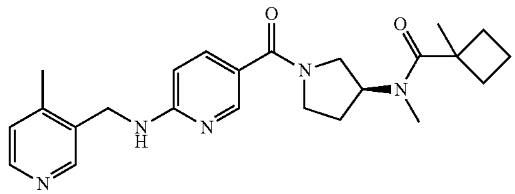 [SMILES: Cc1ccncc1CNc1ccc(C(=O)N2CC[C@H](N(C)C(=O)C3(C)CCC3)C2)cn1] | | 422 [M + H]+ | 0.83 (C) |
| 1.10 | III.1 | HCl, (4-methoxypyridin-3-yl)methanamine HCl | 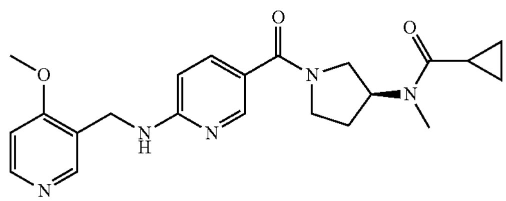 [SMILES: COc1ccncc1CNc1ccc(C(=O)N2CC[C@H](N(C)C(=O)C3CC3)C2)cn1] | | 410 [M + H]+ | 0.76 (C) |
| 1.11 | I.1 | HCl, (S)-1-(6-chloropyridin-3-yl)ethanamine | | | 2 d | 402 [M + H]+ | 0.79 (C) |
| 1.12 | I.1 | (S)-1-(3-cyanophenyl)ethanamine HCl | | | 2 d | 392 [M + H]+ | 0.80 (C) |
| 1.13 | III.1 | (6-chloropyridin-3-yl)methanamine | | | 1.3 eq amine | 414 [M + H]+ | 0.81 (C) |
| 1.14 | XVI.1 | pyridin-3-ylmethanamine | | | 2 h | 408 [M + H]+ | 0.64 (A) |

-continued

| Ex. | Starting materials | | Structure | Reaction conditions | ESI-MS | HPLC Rt [min] (method) |
|---|---|---|---|---|---|---|
| 1.15 | III.1 | (structure) | (structure) | | 394 [M + H]+ | 0.75 (C) |
| 1.16 | I.1 | HCl (structure) | (structure) | | 394 [M + H]+ | 0.75 (C) |
| 1.17 | I.1 | XXVI.1 | (structure) | 120° C. overnight and 140° C. overnight | 448 [M + H]+ | 0.71 (A) |
| 1.18 | XVI.1 | (structure) | (structure) | | 422 [M + H]+ | 0.82 (C) |
| 1.19 | I.1 | XXV.1 | (structure) | 1.5 eq amine; 3.0 eq DIPEA; 100° C., 2 d | 446 [M + H]+ | 0.60 (C) |
| 1.20 | I.1 | (structure) | (structure) | 120° C. overnight and 140° C. overnight | 448 [M + H]+ | 0.72 (A) |
| 1.21 | I.1 | (structure) | (structure) | 1.5 eq amine; 6.0 eq DIPEA | 460 [M + H]+ | 0.74 (C) |

-continued

| Ex. | Starting materials | | Structure | Reaction conditions | ESI-MS | HPLC Rt [min] (method) |
|---|---|---|---|---|---|---|
| 1.22 | XVI.1 | HCl HCl (4-methoxypyridin-3-yl)methanamine | [structure] | | 438 [M + H]+ | 0.83 (C) |
| 1.23 | I.1 | XXV.2 | [structure] | 120° C.; 2 d | 460 [M + H]+ | 0.65 (A) |
| 1.24 | III.1 | (6-aminopyridin-3-yl)methanamine and 4-aminobenzylamine | [structure] | | 395 [M + H]+ | 0.72 (C) |
| 1.25 | I.1 | XXV.3 | [structure] | | 424 [M + H]+ | 0.73 (C) |
| 1.26 | XVI.1 | X.3 | [structure] | | 423 [M + H]+ | 0.78 (C) |
| 1.27 | I.1 | 3-(1-aminoethyl)benzenesulfonamide | [structure] | 1.3 eq amine; 6.0 eq DIPEA | 446 [M + H]+ | 0.66 (C) |
| 1.28 | XVI.1 | (6-chloropyridin-3-yl)methanamine | [structure] | 1.3 eq amine; 5.0 eq DIPEA | 442 [M + H]+ | 0.87 (C) |

-continued
| Ex. | Starting materials | Structure | Reaction conditions | ESI-MS | HPLC Rt [min] (method) |
|---|---|---|---|---|---|
| 1.29 | I.1 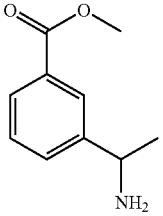 | 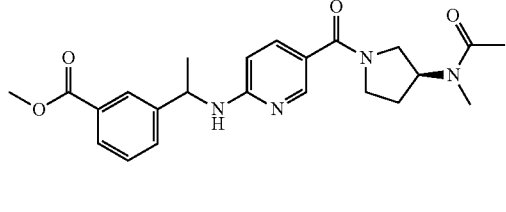 [SMILES: COC(=O)c1cccc(C(C)Nc2ccc(C(=O)N3CC[C@H](N(C)C(C)=O)C3)cn2)c1] | 1.48 eq amine; 6.0 eq DIPEA | 425 [M + H]⁺ | 0.84 (C) |
| 1.30 | XVI.1 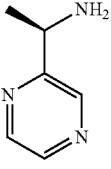 | 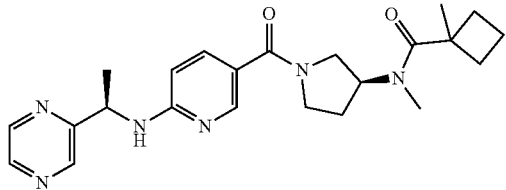 [SMILES: C[C@@H](Nc1ccc(C(=O)N2CC[C@H](N(C)C(=O)C3(C)CCC3)C2)cn1)c1cnccn1] | | 423 [M + H]⁺ | 0.81 (C) |
| 1.31 | XVI.1 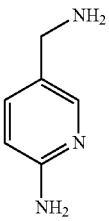 | 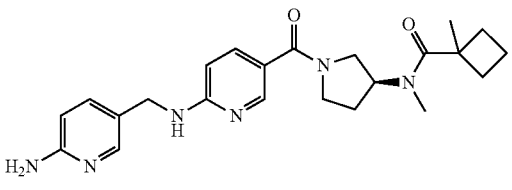 [SMILES: CN(C(=O)C1(C)CCC1)[C@H]1CCN(C(=O)c2ccc(NCc3ccc(N)nc3)nc2)C1] | | 423 [M + H]⁺ | 0.64 (A) |
| 1.33 | III.1 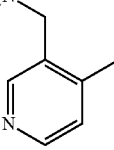 | 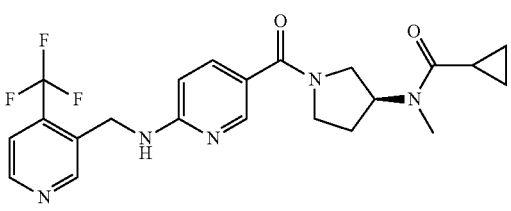 [SMILES: CN(C(=O)C1CC1)[C@H]1CCN(C(=O)c2ccc(NCc3cnccc3C(F)(F)F)nc2)C1] | | 448 [M + H]⁺ | 0.85 (C) |
| 1.34 | I.1 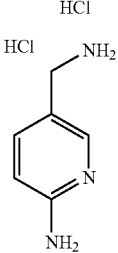 | 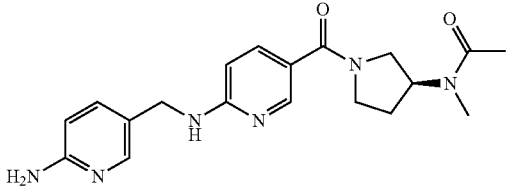 [SMILES: CC(=O)N(C)[C@H]1CCN(C(=O)c2ccc(NCc3ccc(N)nc3)nc2)C1] | | 369 [M + H]⁺ | 0.65 (C) |
| 1.35 | I.1   X.4 | 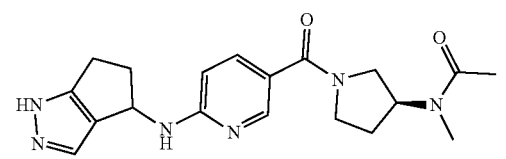 [SMILES: CC(=O)N(C)[C@H]1CCN(C(=O)c2ccc(NC3CCc4[nH]ncc43)nc2)C1] | 1.5 eq amine; 6.0 eq DIPEA; 100° C.; 4 d | 369 [M + H]⁺ | 0.65 (C) |

-continued

| Ex. | Starting materials | Structure | Reaction conditions | ESI-MS | HPLC Rt [min] (method) |
|---|---|---|---|---|---|
| 1.36 | I.1 | 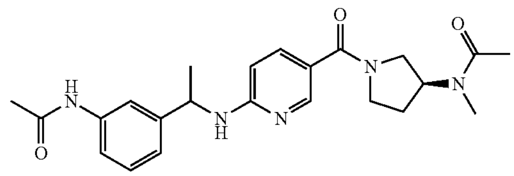 [SMILES: CC(=O)Nc1cccc(C(C)Nc2ccc(C(=O)N3CC[C@H](N(C)C(C)=O)C3)cn2)c1] | 1.5 eq amine; 6.0 eq DIPEA | 424 [M + H]⁺ | 0.74 (C) |
| 1.37 | I.1 | 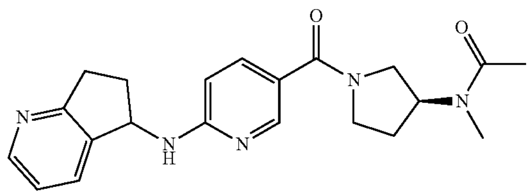 [SMILES: CC(=O)N(C)[C@H]1CCN(C(=O)c2ccc(NC3CCc4ncccc43)nc2)C1] | 1.5 eq amine; 6.0 eq DIPEA; 100° C.; 3 d | 380 [M + H]⁺ | 0.71 (C) |
| 1.38 | III.1 | 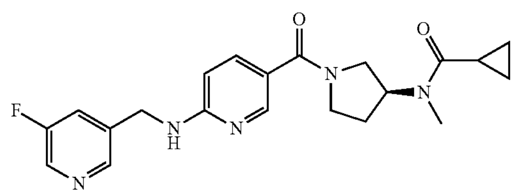 [SMILES: CN(C(=O)C1CC1)[C@H]1CCN(C(=O)c2ccc(NCc3cncc(F)c3)nc2)C1] | | 398 [M + H]⁺ | 0.76 (C) |
| 1.39 | XVI.1 | 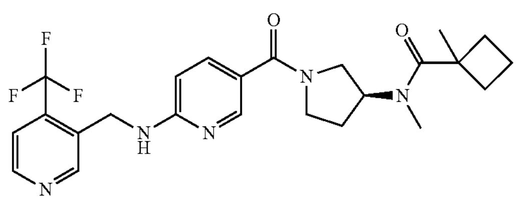 [SMILES: CN(C(=O)C1(C)CCC1)[C@H]1CCN(C(=O)c2ccc(NCc3cnccc3C(F)(F)F)nc2)C1] | | 476 [M + H]⁺ | 0.91 (C) |
| 1.40 | I.1 | 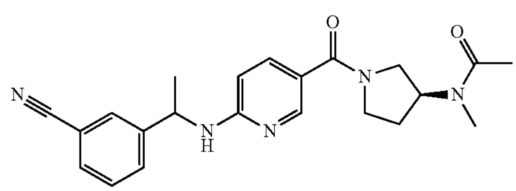 [SMILES: CC(=O)N(C)[C@H]1CCN(C(=O)c2ccc(NC(C)c3cccc(C#N)c3)nc2)C1] | | 392 [M + H]⁺ | 0.79 (C) |
| 1.41 | I.1 | 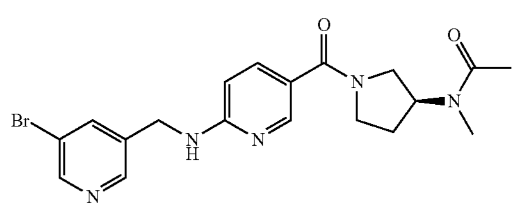 [SMILES: CC(=O)N(C)[C@H]1CCN(C(=O)c2ccc(NCc3cncc(Br)c3)nc2)C1] | | 432 [M + H]⁺ | 0.76 (C) |
| 1.42 | I.1 | 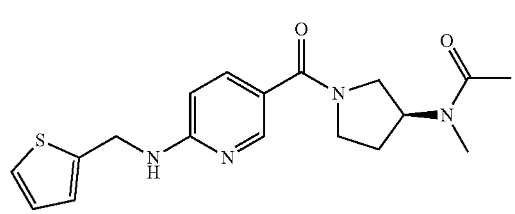 [SMILES: CC(=O)N(C)[C@H]1CCN(C(=O)c2ccc(NCc3cccs3)nc2)C1] | 1.5 eq amine; 6.0 eq DIPEA; 100° C.; overnight | 359 [M + H]⁺ | 0.77 (C) |

| Ex. | Starting materials | Structure | Reaction conditions | ESI-MS | HPLC Rt [min] (method) |
|---|---|---|---|---|---|
| 1.43 | I.1 | (5-fluoropyridin-3-yl)methylamine coupled structure | | 372 [M + H]+ | 0.71 (C) |
| 1.44 | III.1 | (6-(dimethylamino)pyridin-3-yl)methylamine coupled structure | | 423 [M + H]+ | 0.82 (C) |
| 1.45 | I.1, XXV.4 | dimethylsulfamoyl phenyl ethyl structure | | 474 [M + H]+ | 0.81 (C) |
| 1.46 | XVI.1 | (6-(dimethylamino)pyridin-3-yl)methylamine with methylcyclobutyl structure | | 451 [M + H]+ | 0.65 (A) |
| 1.47 | III.1 | (6-methoxypyridin-3-yl)methylamine coupled structure | | 410 [M + H]+ | 0.80 (C) |
| 1.48 | I.1 | HCl, 3-(3-(2,2,2-trifluoroethyl)-1,2,4-oxadiazol-5-yl)benzylamine structure | 2.25 eq amine; 6.0 eq DIPEA; 100° C.; 4 d | 503 [M + H]+ | 0.90 (C) |

-continued

| Ex. | Starting materials | Structure | Reaction conditions | ESI-MS | HPLC Rt [min] (method) |
|---|---|---|---|---|---|
| 1.49 | I.1 | 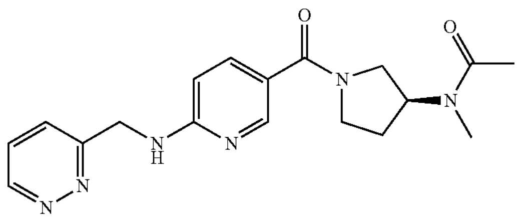 [SMILES: CC(=O)N(C)[C@H]1CCN(C(=O)c2ccc(NCc3cccnn3)nc2)C1] | 6 eq amine; 120° C.; overnight 100° C.; 5 d | 355 [M + H]+ | 0.62 (C) |
| 1.56 | I.1 | 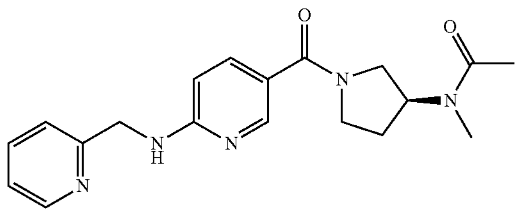 [SMILES: CC(=O)N(C)[C@H]1CCN(C(=O)c2ccc(NCc3ccccn3)nc2)C1] | 6 h | 354 [M + H]+ | 0.67 (C) |
| 1.62 | I.1 | 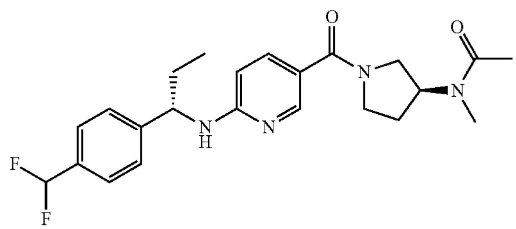 [SMILES: CC[C@H](Nc1ccc(C(=O)N2CC[C@H](N(C)C(C)=O)C2)cn1)c1ccc(C(F)F)cc1] | | 431 [M + H]+ | 0.91 (C) |
| 1.76 | XVI.1 | 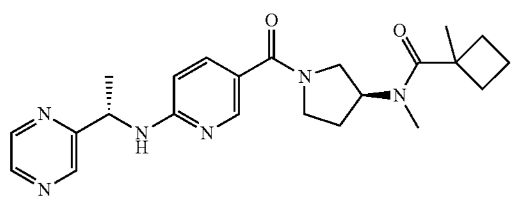 [SMILES: C[C@H](Nc1ccc(C(=O)N2CC[C@H](N(C)C(=O)C3(C)CCC3)C2)cn1)c1cnccn1] | 4.5 eq DIPEA | 423 [M + H]+ | 0.82 (C) |
| 1.81 | I.1 | 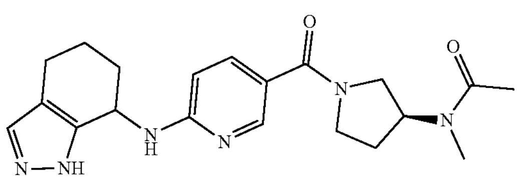 [SMILES: CC(=O)N(C)[C@H]1CCN(C(=O)c2ccc(NC3CCCc4cn[nH]c43)nc2)C1] | 1.5 eq amine; 6.0 DIPEA; 100° C., overnight | 383 [M + H]+ | 0.74 (C) |
| 1.87 | I.1 | 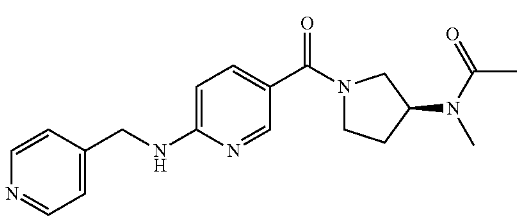 [SMILES: CC(=O)N(C)[C@H]1CCN(C(=O)c2ccc(NCc3ccncc3)nc2)C1] | 6 h | 354 [M + H]+ | 0.65 (C) |
| 1.88 | I.1 XXXXII.1 | 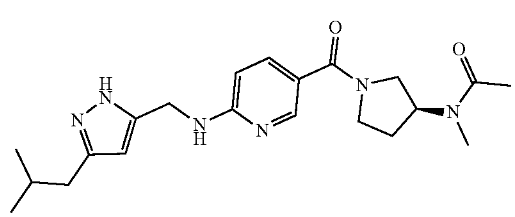 [SMILES: CC(=O)N(C)[C@H]1CCN(C(=O)c2ccc(NCc3cc(CC(C)C)n[nH]3)nc2)C1] | 3 h | 399 [M + H]+ | 0.79 (C) |

| Ex. | Starting materials | Structure | Reaction conditions | ESI-MS | HPLC Rt [min] (method) |
|---|---|---|---|---|---|
| 1.90 | I.1 | 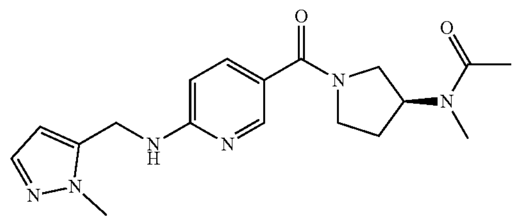 [SMILES: CC(=O)N(C)[C@H]1CCN(C(=O)c2ccc(NCc3ccnn3C)nc2)C1] | 1.2 eq amine; 3.0 eq DIPEA; 100° C.; overnight | 357 [M + H]⁺ | 0.29 (P) |

\* The stereochemistry at the chiral center of the enantiomerically and diastereomerically pure compound was not determined.

Example 2

Example 2.1 (General Route)

N-Methyl-N-[(3S)-1-{6-[(2-phenylpropan-2-yl)amino]pyridine-3-carbonyl}pyrrolidin-3-yl]cyclopropanecarboxamide

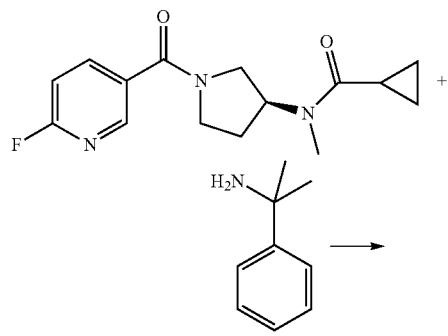

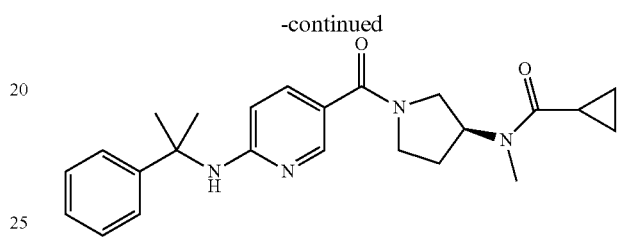

A mixture of 70 mg (0.24 mmol) N-[(3S)-1-(6-fluoropyridine-3-carbonyl)pyrrolidin-3-yl]-N-methylcyclopropanecarboxamide (ex. 111.1) and 0.14 mL (0.96 mmol) cumylamine (CAS No. 585-32-0) in 2 mL NMP is stirred in a microwave at 190° C. for 24 h. Afterwards it is filtered through a microdisk syringe filter and purified by HPLC to provide the product.

$C_{24}H_{30}N_4O_2$ (M=406.52)

ESI-MS: 407 [M+H]⁺

$R_t$ (HPLC) 0.75 min (method A)

The following compounds are prepared according to the general procedure (example 2.1) described above:

| Ex. | Starting materials | Structure | Reaction conditions | ESI-MS | HPLC Rt [min] (method) |
|---|---|---|---|---|---|
| 2.2 | III.2 | 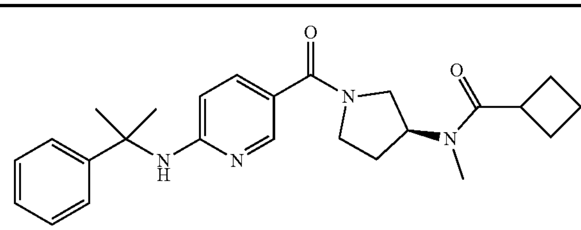 | in a heating block | 421 [M + H]⁺ | 0.96 (C) |
| 2.3 | III.3 | 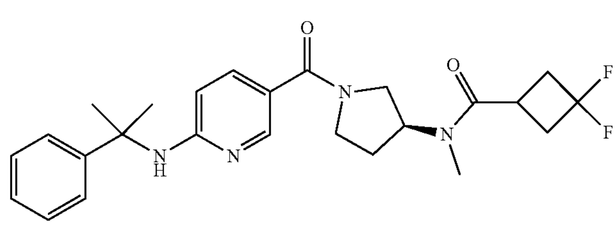 [SMILES: CN(C(=O)C1CC(F)(F)C1)[C@H]1CCN(C(=O)c2ccc(NC(C)(C)c3ccccc3)nc2)C1] | in a heating block | 457 [M + H]⁺ | 0.97 (C) |

Example 3

Example 3.1 (General Route)

N-Methyl-N-[(3S)-1-(6-{[(pyridin-3-yl)methyl]amino}pyridine-3-carbonyl)pyrrolidin-3-yl]cyclobutanecarboxamide

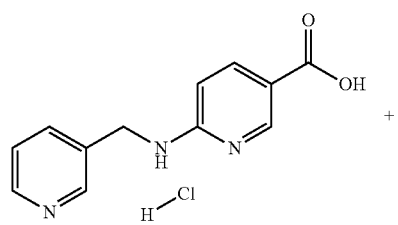

To a mixture of 26.6 mg (0.10 mmol) 6-{[(pyridin-3-yl)methyl]amino}pyridine-3-carboxylic acid hydrochloride (ex. V.1), 21.9 mg (0.10 mmol) N-methyl-N-[(3S)-pyrrolidin-3-yl]cyclobutanecarboxamide hydrochloride (ex. VI.1) and 56.8 µL (0.33 mmol) DIPEA in 1 mL DMF is added 41.8 mg (0.11 mmol) HATU. The reaction mixture is stirred at RT overnight, filtered through a microdisk syringe filter and purified by HPLC to provide the product.

$C_{22}H_{27}N_5O_2$ (M=393.48)

ESI-MS: 394 [M+H]$^+$ $R_t$ (HPLC) 0.50 min (method D)

The following compounds are prepared according to the general procedure (example 3.1) described above:

| Ex. | Starting materials | | Structure | Reaction conditions | ESI-MS | HPLC Rt [min] (method) |
|---|---|---|---|---|---|---|
| 3.2 | XXIII.1 | X.1 | 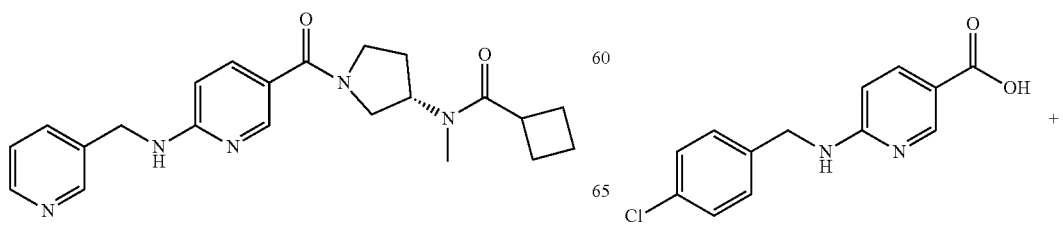 | | 335 [M + H]$^+$ | 0.90 (C) |
| 3.3 | V.1 | X.1 | 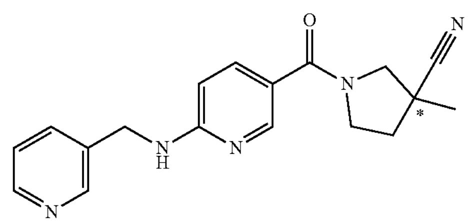 [SMILES: CC1(C#N)CCN(C(=O)c2ccc(NCc3cccnc3)nc2)C1] | | 322 [M + H]$^+$ | 0.70 (C) |

\* The stereochemistry at the chiral center of the enantiomerically and diastereomerically pure compound was not determined.

-continued

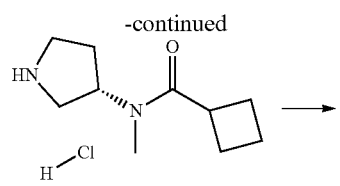

Example 4

Example 4.1 (General Route)

N-[(3S)-1-(6-{[(4-Chlorophenyl)methyl]amino}pyridine-3-carbonyl)pyrrolidin-3-yl]-N-methylacetamide -continued

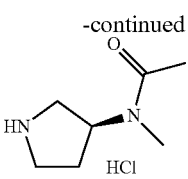

To a mixture of 1.25 g (4.76 mmol) 6-{[(4-chlorophenyl)methyl]amino}pyridine-3-carboxylic acid (ex. VII.1), 1.02 g (5.71 mmol) N-methyl-N-[(3S)-pyrrolidin-3-yl]acetamide hydrochloride (CAS No. 1215264-39-3) and 3.25 mL (19.03 mmol) DIPEA in 10 mL DMF is added 1.60 g (5.00 mmol) TBTU. The reaction mixture is stirred at RT for 10 min and purified by HPLC to provide the product.

$C_{20}H_{23}ClN_4O_2$ (M=386.88)
ESI-MS: 387 [M+H]$^+$
$R_t$ (HPLC) 0.88 min (method C)

The following compounds are prepared according to the general procedure (example 4.1) described above:

| Ex. | Starting materials | | Structure | Reaction conditions | ESI-MS | HPLC Rt [min] (method) |
|---|---|---|---|---|---|---|
| 4.2 | XI.1 | XII.1 | 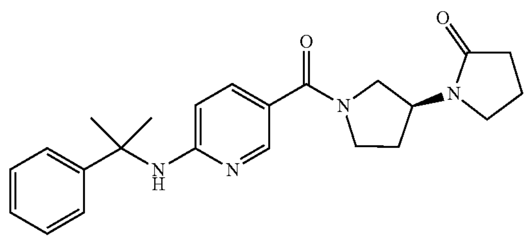 [SMILES: CC(C)(Nc1ccc(C(=O)N2CC[C@H](N3CCCC3=O)C2)cn1)c1ccccc1] | | 393 [M + H]$^+$ | 0.72 (A) |
| 4.3 | XI.1 | XII.2 | 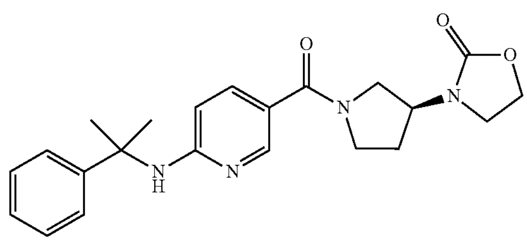 [SMILES: CC(C)(Nc1ccc(C(=O)N2CC[C@H](N3CCOC3=O)C2)cn1)c1ccccc1] | 1.1 eq amine; 1.15 eq TBTU; 3 eq DIPEA; 15 h | 395 [M + H]$^+$ | 0.71 (A) |
| 4.4 | XI.1 | | 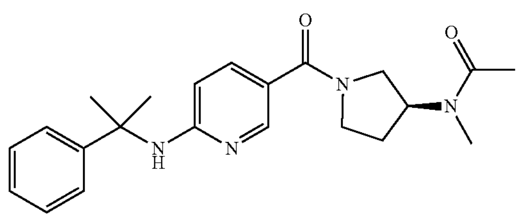 [SMILES: CC(=O)N(C)[C@H]1CCN(C(=O)c2ccc(NC(C)(C)c3ccccc3)nc2)C1] | | 381 [M + H]$^+$ | 0.67 (C) |
| 4.5 | XI.1 | X.2 | 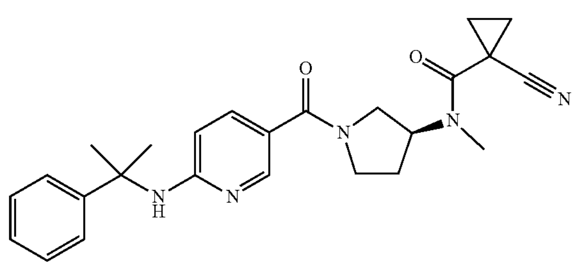 [SMILES: CN(C(=O)C1(C#N)CC1)[C@H]1CCN(C(=O)c2ccc(NC(C)(C)c3ccccc3)nc2)C1] | 1.1 eq amine; 1.15 eq TBTU; 3 eq DIPEA; 15 h | 432 [M + H]$^+$ | 0.53 (D) |

-continued

| Ex. | Starting materials | Structure | Reaction conditions | ESI-MS | HPLC Rt [min] (method) |
|---|---|---|---|---|---|
| 4.6 | XI.2 | 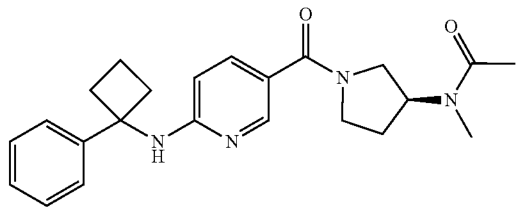 [SMILES: CC(=O)N(C)[C@H]1CCN(C(=O)c2ccc(NC3(c4ccccc4)CCC3)nc2)C1] | 1.01 eq. amine; 1.02 eq TBTU, 2.33 eq DIPEA; 15 h | 393 [M + H]+ | 0.74 (A) |
| 4.7 | XI.3 | 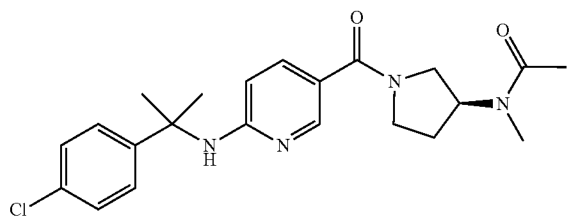 [SMILES: CC(=O)N(C)[C@H]1CCN(C(=O)c2ccc(NC(C)(C)c3ccc(Cl)cc3)nc2)C1] | 1.05 eq amine; 1.10 TBTU; 3 eq DIPEA; RT; 15 h | 415 [M + H]+ | 0.77 (A) |

Example 5

Example 5.1.A and Example 5.1.B

N-Methyl-N-[(3S)-1-(6-{[(1R)-1-(1,3-thiazol-2-yl)ethyl]amino}pyridine-3-carbonyl)pyrrolidin-3-yl]acetamide N-methyl-N-[(3S)-1-(6-{[(1S)-1-(1,3-thiazol-2-yl)ethyl]amino}pyridine-3-carbonyl)pyrrolidin-3-yl]acetamide

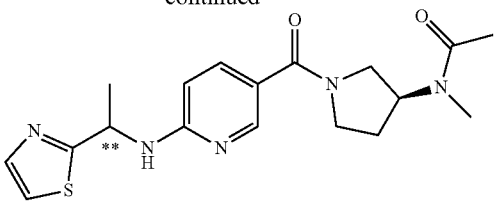

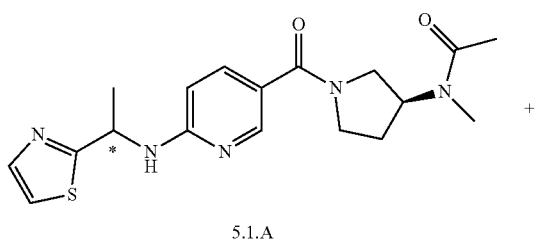

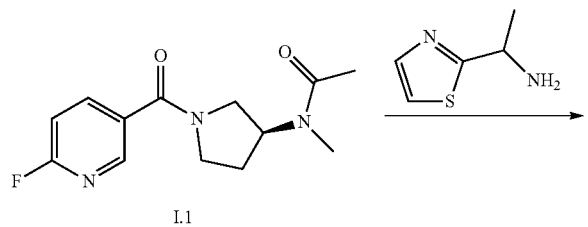

26.5 mg (0.10 mmol) N-[(3S)-1-(6-Fluoropyridine-3-carbonyl)pyrrolidin-3-yl]-N-methylacetamide (ex. I.1) is dissolved in 1 mL DMSO and 51.6 µL (0.30 mmol) DIPEA and 15.4 mg (0.12 mmol) 1-thiazol-2-yl-ethylamine (CAS No. 432047-36-4) are added. The reaction mixture is stirred at 100° C. overnight and additionally at 120° C. for 24 h. More1-thiazol-2-yl-ethylamine (15.4 mg, 0.12 mmol) is added to complete conversion at 120° C. for 24 h. The reaction mixture is filtered through a microdisk syringe filter and purified by HPLC. The isolated racemic product is purified by chiral SFC (CHIRAL ART® Cellulose-SB 10×250 mm; 5 µL; scCO$_2$/IPA+20 mM NH$_3$ 80:20) to obtain the enantiomeric pure products. The absolute stereochemistry at the chiral center of the enantiomerically and diastereomerically pure compound was not determined. Product 5.1.A (first eluting):

$C_{18}H_{23}N_5O_2S$ (M=373.47)
ESI-MS: 374 [M+H]+
R$_t$ (chiral HPLC) 2.99 min (method E)
Product 5.1.B (second eluting):
$C_{18}H_{23}N_5O_2S$ (M=373.47)
ESI-MS: 374 [M+H]+
R$_t$ (chiral HPLC) 3.49 min (method E)

Example 6

Example 6.1.A and Example 6.1.B

N-Methyl-N-[(3S)-1-(6-{[(1S)-1-(pyridin-3-yl)ethyl]amino}pyridine-3carbonyl)pyrrolidin-3-yl]acetamide N-Methyl-N-[(3S)-1-(6-{[(1R)-1-(pyridin-3-yl)ethyl]amino}pyridine-3carbonyl)pyrrolidin-3-yl]acetamide

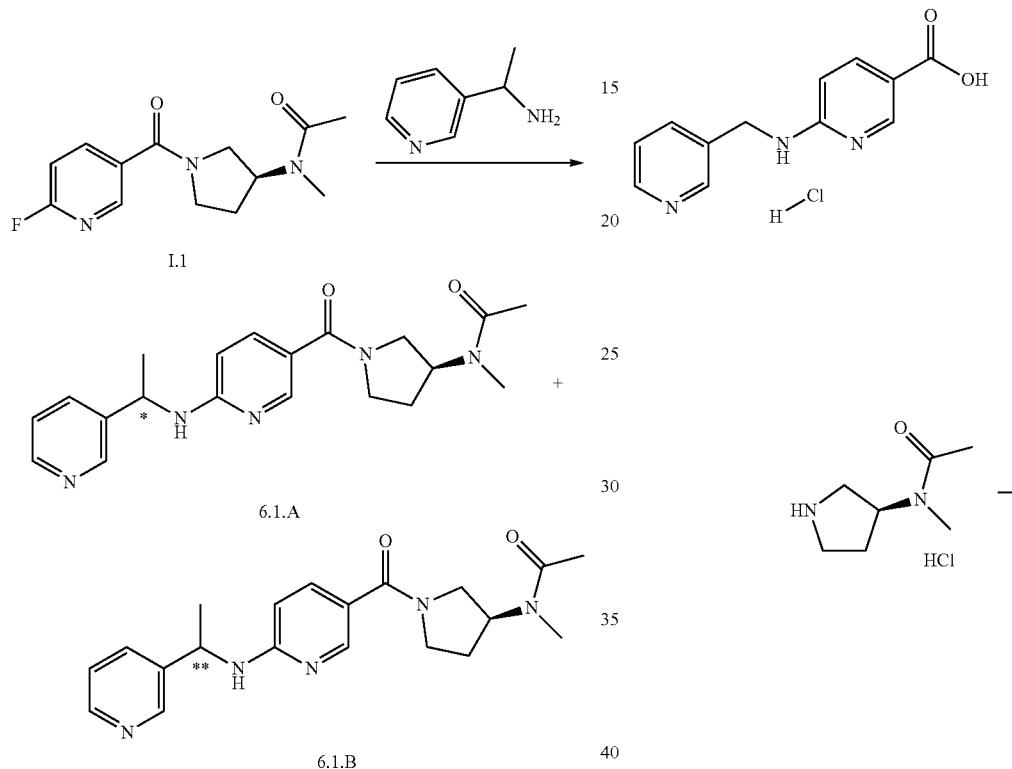

300 mg (1.13 mmol) N-[(3S)-1-(6-Fluoropyridine-3-carbonyl)pyrrolidin-3-yl]-N-methylacetamide (ex. I.1), 276 mg (2.26 mmol) 1-pyridin-3-ylethylamine (CAS No. 56129-55-6) and 0.97 mL (10.00 mmol) DIPEA are dissolved with 2.5 mL DMSO and stirred at 120° C. overnight. The reaction mixture is poured into an aq. $NaHCO_3$ solution and the water phase is extracted twice with DCM. The pooled organic phases are dried with PTK and reduced to dryness in vacuo. The residue is dissolved with MeOH, filtered and purified by HPLC. The racemic product is purified by chiral SFC (CHIRAL ART® Amylose-SA_10×250 mm; 5 μL; $scCO_2$/IPA+20 mM $NH_3$ 65:35) to obtain the enantiomeric pure products. The absolute stereochemistry at the chiral center of the enantiomerically and diastereomerically pure compound was not determined.

Product 6.1.A (first eluting)
$C_{20}H_{25}N_5O_2$ (M=367.45)
ESI-MS: 368 [M+H]+
$R_t$ (HPLC) 0.69 min (method C)
$R_t$ (chiral SFC) 5.57 min (method L)
Product 6.1.B (second eluting)
$C_{20}H_{25}N_5O_2$ (M=367.45)
ESI-MS: 368 [M+H]+
$R_t$ (HPLC) 0.69 min (method C)
$R_t$ (chiral SFC) 5.84 min (method L)

Example 7

Example 7.1 (General Route)

N-Methyl-N-[(3S)-1-(6-{[(pyridin-3-yl)methyl]amino}pyridine-3-carbonyl)pyrrolidin-3-yl]acetamide

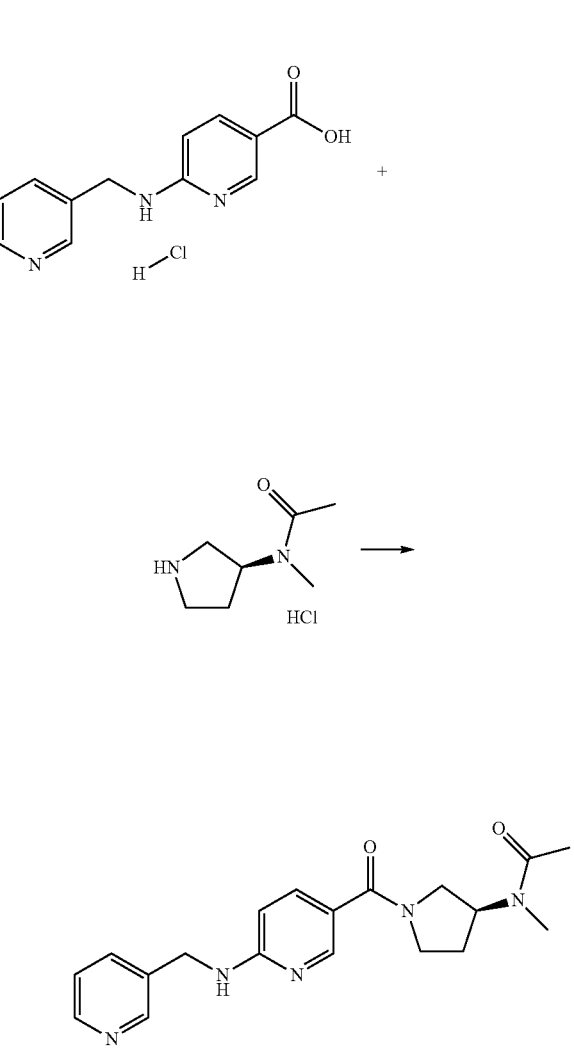

0.47 g (1.77 mmol) 6-{[(Pyridin-3-yl)methyl]amino}pyridine-3-carboxylic acid hydrochloride (ex. V.1), 0.47 g (2.65 mmol) N-methyl-N—(S)-pyrrolidin-3-yl-acetamide hydrogenchloride (CAS No. 1215264-39-3) and 1.21 mL (7.08 mmol) DIPEA are dissolved in 5 mL DMF and 1.01 g (2.65 mmol) HATU is added. The reaction mixture is stirred at RT for 10 min, poured into an aq. $NaHCO_3$ solution and the water phase is extracted twice with DCM. The pooled organic phases are dried with PTK and reduced to dryness in vacuo. The residue is purified by column chromatography (silica gel; DCM/MeOH, 2% to 20%) to obtain the product.

$C_{19}H_{23}N_5O_2$ (M=353.42)
ESI-MS: 354 [M+H]$^+$
$R_t$ (HPLC) 0.68 min (method C)

Example 8

Example 8.1 (General Route)

N,1-Dimethyl-N-[(3S)-1-(6-{[2-(pyridin-3-yl)propan-2-yl]amino}pyridine-3-carbonyl)pyrrolidin-3-yl]cyclobutane-1-carboxamide

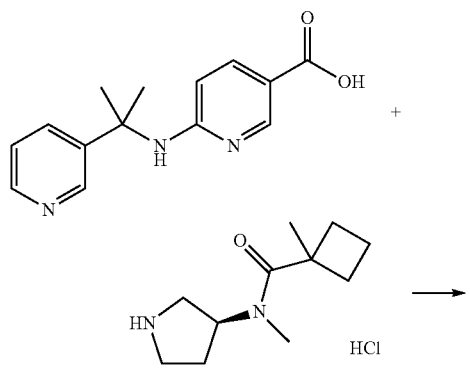

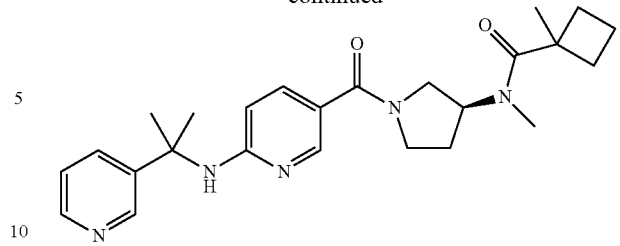

26.0 mg (0.10 mmol) 6-{[2-(Pyridin-3-yl)propan-2-yl]amino}pyridine-3-carboxylic acid (ex. VII.2) and 35.3 mg (0.15 mmol) N,1-dimethyl-N-[(3 S)-pyrrolidin-3-yl]cyclobutane-1-carboxamide hydrochloride (ex. XIV.1) are diluted with 1 mL DMF and 60.5 µL (0.35 mmol) DIPEA is added. The reaction mixture is treated with 57.6 mg (0.15 mmol) HATU. After stirring at RT for 10 min the reaction mixture is quenched with MeOH, filtered through a microdisk syringe filter and purified by HPLC to provide the product.

$C_{25}H_{33}N_5O_2$ (M=435.56)
ESI-MS: 436 [M+H]$^+$
$R_t$ (HPLC) 0.86 min (method C)

The following compounds are prepared according to the general procedure (example 8.1) described above:

| Ex. | Starting materials | | Structure | Reaction conditions | ESI-MS | HPLC Rt [min] (method) |
|---|---|---|---|---|---|---|
| 8.2 | VII.2 | VIII.1 | 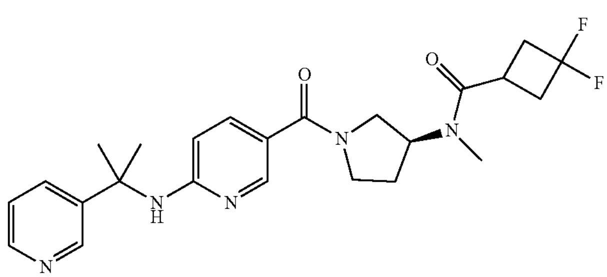 [SMILES: CN(C(=O)C1CC(F)(F)C1)[C@H]1CCN(C(=O)c2ccc(NC(C)(C)c3cccnc3)nc2)C1] | | 458 [M + H]$^+$ | 0.85 (C) |
| 8.3 | VII.2 | X.1 | 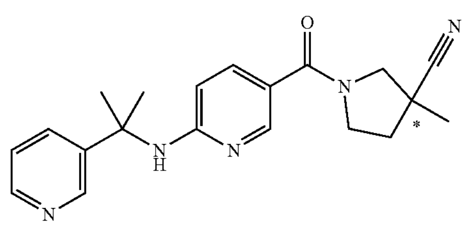 [SMILES: CC1(C#N)CCN(C(=O)c2ccc(NC(C)(C)c3cccnc3)nc2)C1] | purification: by HPLC (ACN/H$_2$O/ TFA) and (ACN/H$_2$O/ NH$_4$OH) | 350 [M + H]$^+$ | 0.80 (C) |
| 8.4 | V.1 | VIII.1 | 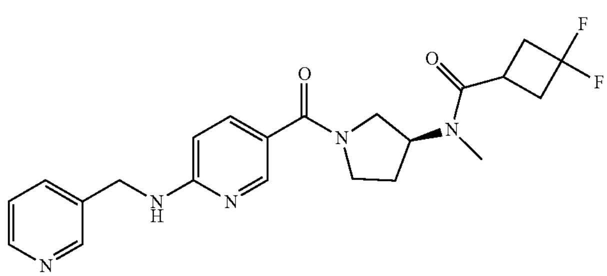 [SMILES: CN(C(=O)C1CC(F)(F)C1)[C@H]1CCN(C(=O)c2ccc(NCc3cccnc3)nc2)C1] | purification: HPLC (ACN/water/ TFA) and column chromatography (silica gel, DCM/ MeOH) | 430 [M + H]$^+$ | 0.61 (A) |

-continued

| Ex. | Starting materials | | Structure | Reaction conditions | ESI-MS | HPLC Rt [min] (method) |
|---|---|---|---|---|---|---|
| 8.5 | V.1 | XVII.1 | 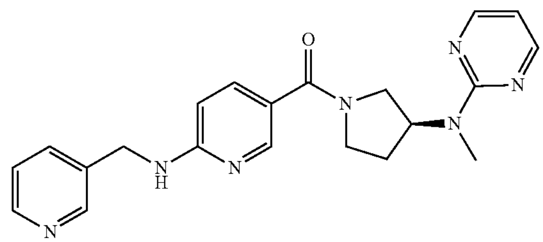 [SMILES: CN(c1ncccn1)[C@H]1CCN(C(=O)c2ccc(NCc3cccnc3)nc2)C1] | 4.5 eq DIPEA | 390 [M + H]⁺ | 0.80 (C) |
| 8.6 | VII.3 | VI.2 | 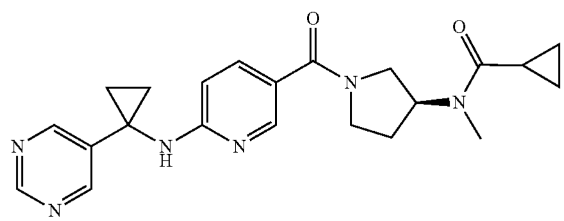 [SMILES: CN(C(=O)C1CC1)[C@H]1CCN(C(=O)c2ccc(NC3(c4cncnc4)CC3)nc2)C1] | | 407 [M + H]⁺ | 0.72 (C) |
| 8.7 | VII.2 | | 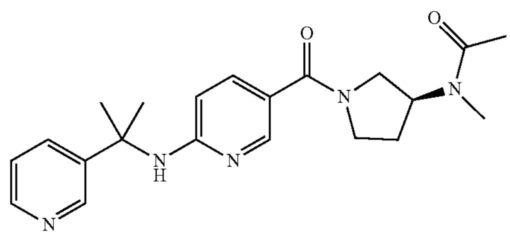 [SMILES: CC(=O)N(C)[C@H]1CCN(C(=O)c2ccc(NC(C)(C)c3cccnc3)nc2)C1] | 120° C.; overnight; purification: HPLC (ACN/water/ NH₄OH) and HPLC (ACN/water/ TFA) | 382 [M + H]⁺ | 0.56 (A) |
| 8.8 | XXII.1 | | 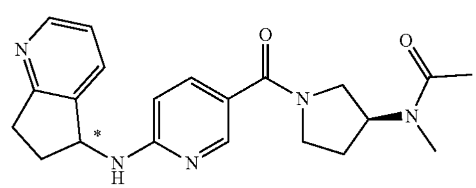 [SMILES: CC(=O)N(C)[C@H]1CCN(C(=O)c2ccc(NC3CCc4ncccc43)nc2)C1] | 6.0 eq DIPEA, 15 min | 380 [M + H]⁺ | 0.70 (C) |
| 8.9 | VII.1 | XII.1 | 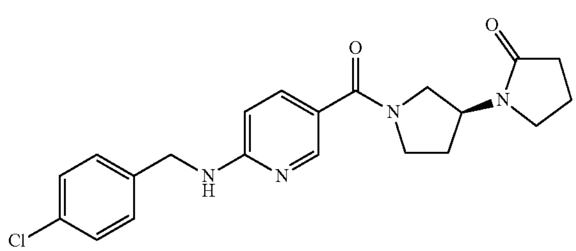 [SMILES: O=C(c1ccc(NCc2ccc(Cl)cc2)nc1)N1CC[C@H](N2CCCC2=O)C1] | | 399 [M + H]⁺ | 0.87 (C) |
| 8.10 | VII.3 | XIV.1 | 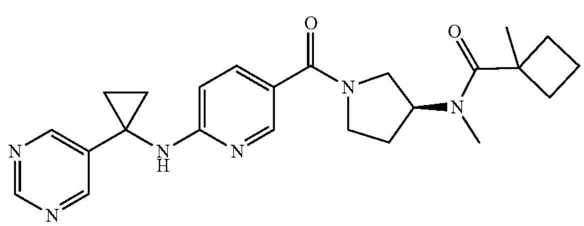 [SMILES: CN(C(=O)C1(C)CCC1)[C@H]1CCN(C(=O)c2ccc(NC3(c4cncnc4)CC3)nc2)C1] | | 435 [M + H]⁺ | 0.80 (C) |

| Ex. | Starting materials | Structure | Reaction conditions | ESI-MS | HPLC Rt [min] (method) |
|---|---|---|---|---|---|
| 8.11 | V.1 | 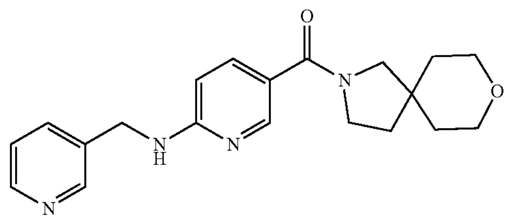 [SMILES: O=C(c1ccc(NCc2cccnc2)nc1)N1CCC2(CCOCC2)C1] | 1.2 eq amine; 1.5 eq HATU; 3.0 eq DIPEA | 353 [M + H]⁺ | 0.73 (C) |
| 8.12 | VII.1 XII.2 | 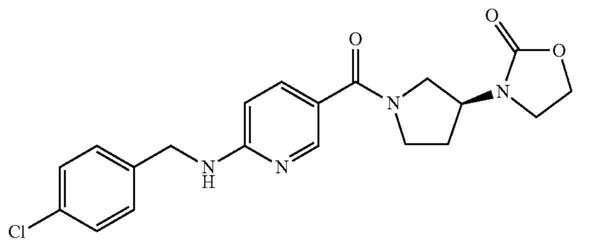 [SMILES: O=C(c1ccc(NCc2ccc(Cl)cc2)nc1)N1CC[C@H](N2CCOC2=O)C1] | | 401 [M + H]⁺ | 0.86 (C) |
| 8.13 | VII.3 | 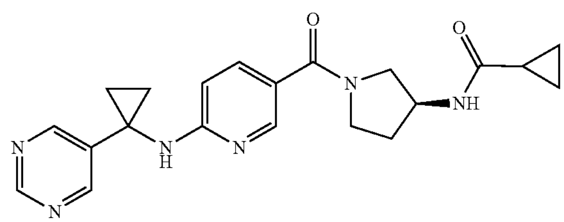 [SMILES: O=C(N[C@H]1CCN(C(=O)c2ccc(NC3(c4cncnc4)CC3)nc2)C1)C1CC1] | | 393 [M + H]⁺ | 0.68 (C) |
| 8.14 | XXII.2 | 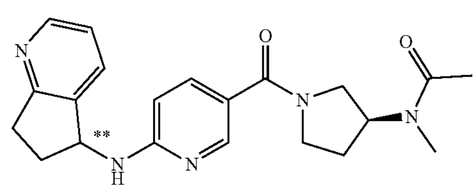 [SMILES: CC(=O)N(C)[C@H]1CCN(C(=O)c2ccc(NC3CCc4ncccc43)nc2)C1] | | 380 [M + H]⁺ | 0.70 (C) |

* and **: The stereochemistry at the chiral center of the enantiomerically and diastereomerically pure compound was not determined.

Example 9

Example 9.1 (General Route)

N-Methyl-N-[(3S)-1-(6-{[(1S)-1-[6-(trifluoromethyl)pyridin-3-yl]ethyl]amino}pyridine-3-carbonyl)pyrrolidin-3-yl]acetamide

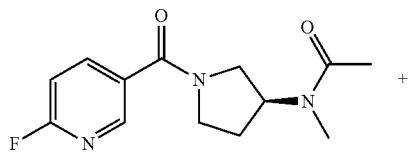

+

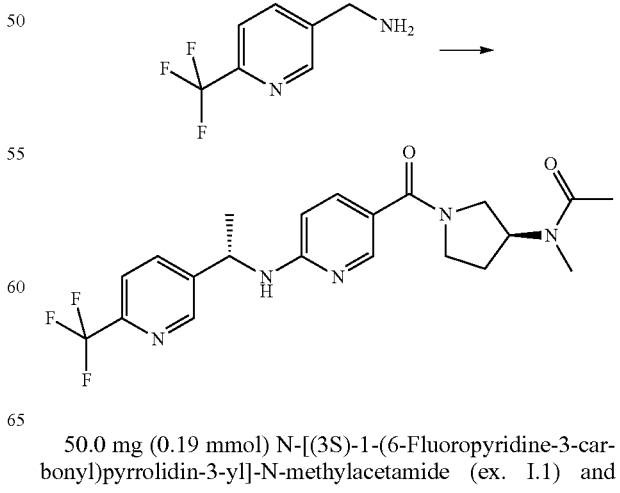

50.0 mg (0.19 mmol) N-[(3S)-1-(6-Fluoropyridine-3-carbonyl)pyrrolidin-3-yl]-N-methylacetamide (ex. I.1) and 107.5 mg (0.57 mmol) (1S)-1-[6-(trifluoromethyl)pyridin-3-yl]ethan-1-amine (CAS No. 1071435-52-5) are diluted with 1 mL NMP and stirred at 130° C. overnight. After cooling the reaction mixture is filtered through a microdisk syringe filter and purified by HPLC to obtain the product.

$C_{21}H_{24}F_3N_5O_2$ (M=435.44)
ESI-MS: 436 [M+H]$^+$
$R_t$ (HPLC) 0.71 min (method A)

The following compounds are prepared according to the general procedure (example 9.1) described above:

| Ex. | Starting materials | Structure | Reaction conditions | ESI-MS | HPLC Rt [min] (method) |
|---|---|---|---|---|---|
| 9.2 | I.1 | 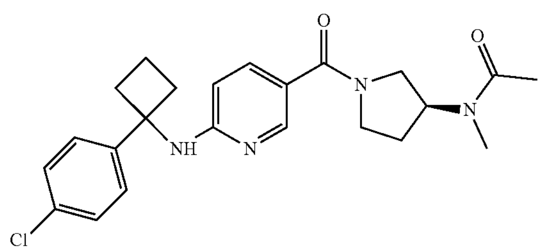 [SMILES: CC(=O)N(C)[C@H]1CCN(C(=O)c2ccc(NC3(c4ccc(Cl)cc4)CCC3)nc2)C1] | 150° C.; overnight | 427 [M + H]$^+$ | 0.79 (A) |
| 9.3 | I.1 | 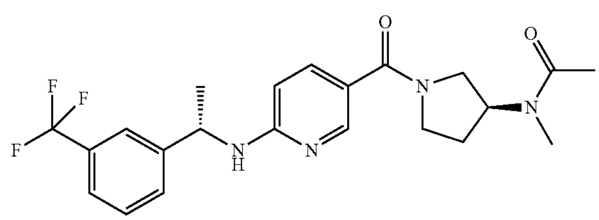 [SMILES: CC(=O)N(C)[C@H]1CCN(C(=O)c2ccc(N[C@@H](C)c3cccc(C(F)(F)F)c3)nc2)C1] | | 435 [M + H]$^+$ | 0.77 (A) |
| 9.4 | I.1 | 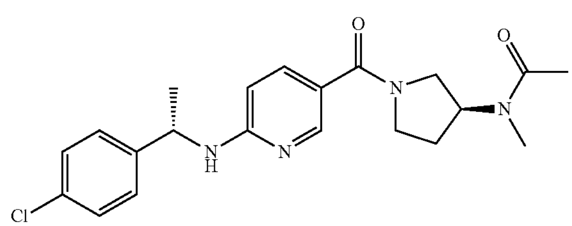 [SMILES: CC(=O)N(C)[C@H]1CCN(C(=O)c2ccc(N[C@@H](C)c3ccc(Cl)cc3)nc2)C1] | 150° C.; overnight | 401 [M + H]$^+$ | 0.91 (A) |
| 9.5 | I.1 | 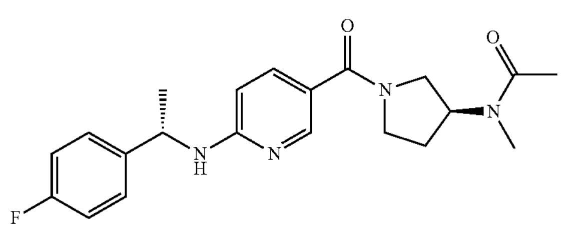 [SMILES: CC(=O)N(C)[C@H]1CCN(C(=O)c2ccc(N[C@@H](C)c3ccc(F)cc3)nc2)C1] | | 385 [M + H]$^+$ | 0.71 (A) |
| 9.6 | I.1 | 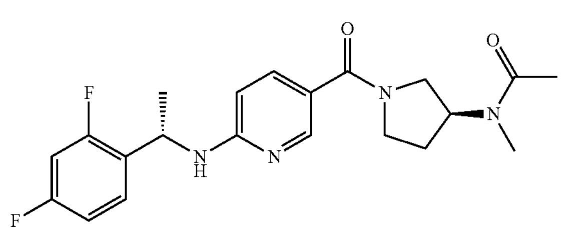 [SMILES: CC(=O)N(C)[C@H]1CCN(C(=O)c2ccc(N[C@@H](C)c3ccc(F)cc3F)nc2)C1] | 150° C. overnight | 403 [M + H]$^+$ | 0.73 (A) |
| 9.7 | I.1 | 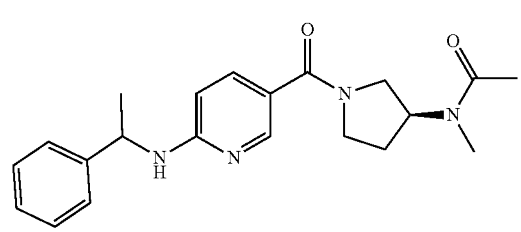 [SMILES: CC(=O)N(C)[C@H]1CCN(C(=O)c2ccc(NC(C)c3ccccc3)nc2)C1] | 2.0 eq amine; 3.5 eq DIPEA; 15 h | 367 [M + H]$^+$ | 0.74 (B) |

Example 10

Example 10.1

3-[1-({5-[(3S)-3-(N-Methylacetamido)pyrrolidine-1-carbonyl]pyridin-2-yl}amino)ethyl]benzamide

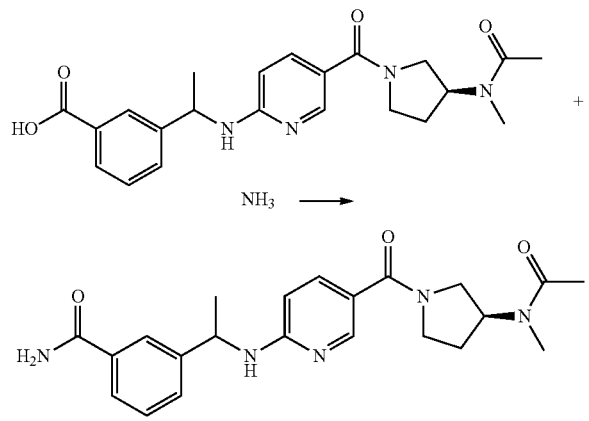

40.0 mg (0.10 mmol) 3-[1-({5-[(3S)-3-(N-Methylacetamido)pyrrolidine-1-carbonyl]pyridin-2-yl}amino)ethyl]benzoic acid (ex. XXXI.1) and 20.0 mg (0.10 mmol) CDI are dissolved with DMF, stirred at RT for 1 h, then cooled with an ice bath and 0.19 mL (0.10 mmol) conc. ammonia is added dropwise. The reaction mixture is warmed to RT and stirred for 1 h, then purified by HPLC (ACN/water/NH$_4$OH) to afford the product.

$C_{22}H_{27}N_5O_3$ (M=409.48)
ESI-MS: 410 [M+H]$^+$
R$_t$ (HPLC) 0.69 min (method C)

Example 11

Example 11.1

N-[(3S)-1-(6-{[(1S)-1-(6-cyanopyridin-3-yl)ethyl]amino}pyridine-3-carbonyl)pyrrolidin-3-yl]-N-methylacetamide

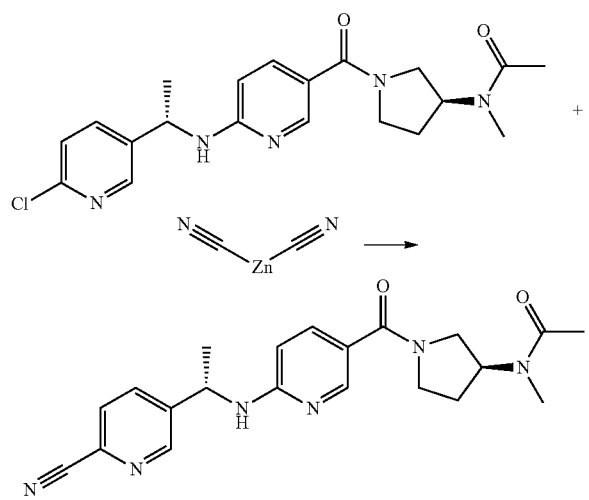

A mixture of 30.0 mg (0.07 mmol) N-[(3S)-1-(6-{[(1S)-1-(6-chloropyridin-3-yl)ethyl]-amino}pyridine-3-carbonyl)pyrrolidin-3-yl]-N-methylacetamide (ex. 1.11), 5.2 mg (0.04 mmol) zinc cyanide, 3.4 mg (0.01 mmol) tris(dibenzylideneacetone)dipalladium (0) and 4.1 mg (0.01 mmol) 1,1'-bis(diphenylphosphino)ferrocene in 2 mL DMF are stirred at 100° C. overnight. To achieve complete conversion, more zinc cyanide (10 mg, 0.08 mmol), more tris(dibenzylideneacetone)dipalladium (0) (3.4 mg, 0.01 mmol) and more 1,1'-bis(diphenylphosphino)-ferrocene (4.1 mg, 0.01 mmol) are added and further stirred at 120° C. for 3 h. The reaction mixture is diluted with ACN, filtered through a microdisk syringe filter and purified by HPLC to obtain the product.

$C_{21}H_{24}N_6O_2$ (M=392.45)
ESI-MS: 393 [M+H]$^+$
R$_t$ (HPLC) 0.64 min (method A)

Analytical HPLC Methods
Method A

| time (min) | Vol % water (incl. 0.1% TFA) | Vol % ACN | Flow [mL/min] |
|---|---|---|---|
| 0.00 | 97 | 3 | 2.2 |
| 0.20 | 97 | 3 | 2.2 |
| 1.20 | 0 | 100 | 2.2 |
| 1.25 | 0 | 100 | 3.0 |
| 1.40 | 0 | 100 | 3.0 |

Analytical column: Sunfire (Waters) 2.5 µm; 3.0×30 mm; column temperature: 60° C.
Method B

| time (min) | Vol % water (incl. 0.1% TFA) | Vol % ACN | Flow [mL/min] |
|---|---|---|---|
| 0.00 | 97 | 3 | 2.2 |
| 0.20 | 97 | 3 | 2.2 |
| 1.20 | 0 | 100 | 2.2 |
| 1.25 | 0 | 100 | 3.0 |
| 1.40 | 0 | 100 | 3.0 |

Analytical column: Stable Bond (Agilent) 1.8 µm; 3.0×30 mm; column temperature: 60° C.
Method C

| time (min) | Vol % water (incl. 0.1% NH$_4$OH) | Vol % ACN | Flow [mL/min] |
|---|---|---|---|
| 0.00 | 97 | 3 | 2.2 |
| 0.20 | 97 | 3 | 2.2 |
| 1.20 | 0 | 100 | 2.2 |
| 1.25 | 0 | 100 | 3 |
| 1.40 | 0 | 100 | 3 |

Analytical column: XBridge C18 (Waters) 2.5 µm; 3.0×30 mm; column temperature: 60° C.
Method D

| Gradient/Solvent Time [min] | % Sol [Water 0.1% NH3] | % Sol [Acetonitrile] | Flow [ml/min] | Temp [° C.] |
|---|---|---|---|---|
| 0.0 | 95.0 | 5.0 | 1.5 | 60.0 |
| 1.3 | 0.0 | 100.0 | 1.5 | 60.0 |
| 1.5 | 0.0 | 100.0 | 1.5 | 60.0 |
| 1.6 | 95.0 | 5.0 | 1.5 | 60.0 |

Preparative column: XBridge (Waters) C18_3.0×30 mm 2.5 µm

Method E

| Gradient Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 75.0 | 25.0 | 4.0 | 40.0 | 2175.0 |
| 10.0 | 75.0 | 25.0 | 4.0 | 40.0 | 2175.0 |

CHIRAL ART® Cellulose SB_4.6×250 mm_5 µm (YMC)
Method F

| Gradient Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 95.0 | 5.0 | 4.0 | 40.0 | 2175.0 |
| 10.0 | 95.0 | 5.0 | 4.0 | 40.0 | 2175.0 |

CHIRAL ART® Cellulose SC_4.6×250 mm_5 µm (YMC)
Method G

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 65.0 | 35.0 | 4.0 | 40.0 | 2175.0 |
| 10.0 | 65.0 | 35.0 | 4.0 | 40.0 | 2175.0 |

CHIRAL ART® Amylose SA_4.6×250 mm_5 µm (YMC)
Method H

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 75.0 | 25.0 | 4.0 | 40.0 | 2175.0 |
| 10.0 | 75.0 | 25.0 | 4.0 | 40.0 | 2175.0 |

Lux® Amylose-2_4.6×250 mm_5 µm (Phenomenex)
Method I

| Gradient/Solvent Time [min] | % Sol [Water 0.1% FA (v/v)] | % Sol [Acetonitrile] | Flow [ml min] | Temp [° C.] |
|---|---|---|---|---|
| 0.0 | 97.0 | 3.0 | 2.2 | 60.0 |
| 0.2 | 97.0 | 3.0 | 2.2 | 60.0 |
| 1.2 | 0.0 | 100.0 | 2.2 | 60.0 |
| 1.25 | 0.0 | 100.0 | 3.0 | 60.0 |
| 1.4 | 0.0 | 100.0 | 3.0 | 60.0 |

Analytical column: Sunfire C18 (Waters) 2.5 µm; 3.0×30 mm; column temperature: 60° C.
Method J

| Gradient/Solvent Time [min] | % Sol [Water 0.1% FA (v/v)] | % Sol [Acetonitrile] | Flow [ml/min] | Temp [° C.] |
|---|---|---|---|---|
| 0.0 | 98.0 | 2.0 | 2.0 | 60.0 |
| 1.2 | 0.0 | 100.0 | 2.0 | 60.0 |
| 1.4 | 0.0 | 100.0 | 2.0 | 60.0 |

Preparative column: XBridge (Waters) C18_3.0×30 mm_2.5 µm

Method K

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 85.0 | 15.0 | 4.0 | 40.0 | 2175.0 |
| 10.0 | 85.0 | 15.0 | 4.0 | 40.0 | 2175.0 |

Lux® Amylose-4_4.6×250 mm_5 µm (Phenomenex)
Method L

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 95.0 | 5.0 | 4.0 | 40.0 | 2175.0 |
| 9.0 | 40.0 | 60.0 | 4.0 | 40.0 | 2175.0 |
| 10.0 | 40.0 | 60.0 | 4.0 | 40.0 | 2175.0 |

Chiralpak® IB_4.6×250 mm_5 µm (Daicel)
Method M

| Gradient/Solvent Time [min] | % Sol [Water 0.032% NH3] | % Sol [MEOH] | Flow [ml/min] | Temp [° C.] |
|---|---|---|---|---|
| 0.0 | 95.0 | 5.0 | 1.5 | 40.0 |
| 2. | 0.0 | 100.0 | 1.5 | 40.0 |

Preparative column: XBridge C18 (Waters) 3.5 µm; 4.6×50 mm; column temperature: 40° C.
Method N

| Gradient/Solvent Time [min] | % Sol [Water 0.1% FA (v/v)] | % Sol [Acetonitrile] | Flow [ml/min] | Temp [° C.] |
|---|---|---|---|---|
| 0.0 | 97.0 | 3.0 | 2.2 | 60.0 |
| 0.2 | 97.0 | 3.0 | 2.2 | 60.0 |
| 1.2 | 0.0 | 100.0 | 2.2 | 60.0 |
| 1.25 | 0.0 | 100.0 | 3.0 | 60.0 |
| 1.4 | 0.0 | 100.0 | 3.0 | 60.0 |

Analytical column: Xbridge (Waters) 2.5 µm; 3.0×30 mm; column temperature: 60° C.
Method O

| Gradient/Solvent Time [min] | % Sol [Water 0.1% FA (v/v)] | % Sol [MeOH] | Flow [ml/min] | Temp [° C.] |
|---|---|---|---|---|
| 0.0 | 95.0 | 5.0 | 4.0 | 60.0 |
| 1.6 | 0.0 | 100.0 | 4.0 | 60.0 |
| 1.85 | 0.0 | 100.0 | 4.0 | 60.0 |
| 1.9 | 95.0 | 5.0 | 4.0 | 60.0 |

Analytical column: Xbridge (Waters) 3.5 µm; 4.6×30 mm; column temperature: 60° C.

Method P

| Gradient/Solvent Time [min] | % Sol [Water 0.1% FA (v/v)] | % Sol [Acetonitrile 0.08% TFA (v/v)] | Flow [ml/min] | Temp [° C.] |
|---|---|---|---|---|
| 0.0 | 95.0 | 5.0 | 1.5 | 60.0 |
| 1.3 | 0.0 | 100.0 | 1.5 | 60.0 |
| 1.5 | 0.0 | 100.0 | 1.5 | 60.0 |
| 1.6 | 95.0 | 5.0 | 1.5 | 60.0 |

Preparative column: Sunfire (Waters) C18_3.0×30 mm_2.5 µm

Description of Biological Properties

Vanin-1 Enzymatic Assay:

The test compounds are dissolved in 100% DMSO at a concentration of 10 mM and in a first step diluted in DMSO to a concentration of 5 mM, followed by serial dilution steps in 100% DMSO. Dilution factor and number of dilution steps may vary according to needs. Typically 8 different concentrations by 1:5 dilutions are prepared, a further intermediate dilutions of the substances is carried out with assay buffer resulting in 1% final DMSO concentration in the assay.

0.1 nM of FLAG-tagged Vanin-1 (AA 22-493, T26I, produced internally) and test compounds are incubated at room temperature for 20 minutes in assay buffer (1 mM DTT, 0.0025% Brij-35, 50 mM HEPES, pH7.5). D-Pantethine (Sigma, Cat #P2125-5G) in assay buffer is added (final concentration 3 µM) and incubated for additional 30 minutes at room temperature. Total assay volume typically is 40 µl but might be adjusted according to needs. Reaction is stopped by adding equal volume of stop solution as the reaction mixture to reach 100 nM HD-pantothenic acid (as an internal standard) and 1% TFA. Assay plates are centrifuged for 2 minutes and the formation of pantothenic acid is detected by RapidFire Mass Spectrometry (mobile phase A: 0.1% formic acid and 0.01% trifluoroacetic acid in water; mobile phase B: 47.5% acetonitrile, 47.5% methanol, 0.1% formic acid and 0.01% trifluoroacetic acid in water) using a C18, 12 µL cartridge (Agilent Cat #G9205A).

The values given in Table I result from measurements of one or more samples. In case of multiple measurements the geometric mean values are given.

Human Whole Blood assay: Pantetheinase (vanin) converts panteheine into pantothenic acid and cysteamine. Accordingly, in the described protocol vanin activity is quantified by formation of pantothenic acid after pantetheine supplementation via pantethine. The assay is applicable to identify vanin inhibitors. Compound stocks are dissolved in DMSO at 10 mM. Further dilutions are performed in RPMI 1640 medium (Gibco, #A-10491-01) and final concentrations in the assay are 0.032 nM-500 nM.

Human blood is drawn into a blood bag (1% heparin, 50 I.E./mL). Blood is aliquoted into cavities of 96-deep-well plates at 290 µL and mixed with 10 µL compound solution or vehicle (30 sec at 1400 rpm on a shaker). Equilibration follows at room temperature, 250 rpm and for 30 min. The assay is starts by adding 10 µL of substrate solution (20 µM pantethine in 1 mM DTT, 0.0025% Brij-35, 50 mM HEPES, pH7.5) to each well, except for some blank wells which receive 10 mL substrate buffer (1 mM DTT, 0.0025% Brij-35, 50 mM HEPES, pH7.5) only. Samples are thoroughly shaken (30 sec, 1400 rpm) and reaction is allowed to take place at room temperature, 250 rpm and for 5 min. The reaction is stopped by addition of a vanin tool inhibitor in excess (BI-1 total conc. 10 µM). Centrifugation of the plate follows at 4° C., 665 G for 10 min. Then the blood plasma samples (100 µL) are transferred into another 96-deep-well plate and proteins are precipitated (5 min on ice) by adding 100 µL of ice cold precipitation solution (1 µM labelled pantothenic acid (di-β-alanine-13C6,15N2 calcium salt, Sigma, #705837) in acetonitrile). Afterwards the plate is centrifuged (4° C., 3220 G, 10 min) and supernatants (50 µL) are collected into another 96-deep-well plate and mixed (10 sec, 1400 rpm) with 150 µL ice cold formic acid (0.1%, Carl Roth GmbH+Co.KG, #CP03.1). The formation of pantothenic acid is detected by RapidFire Mass Spectrometry. A TripleQuad 6500+ (ABSciex, Germany) is equipped with an LC-1290 system, a RapidFire autosampler (Agilent, Germany) and a C18 cartridge Type C 12 µL (Agilent Cat #G9526-80000). Mobile phase A is consisting of 0.09% formic acid and 0.01% trifluoroacetic acid in water and mobile phase B of 0.09% formic acid and 0.01% trifluoroacetic acid in acetonitrile/methanol/water=47.5/47.5/5.

Synthesis of Tool Inhibitor BI-1

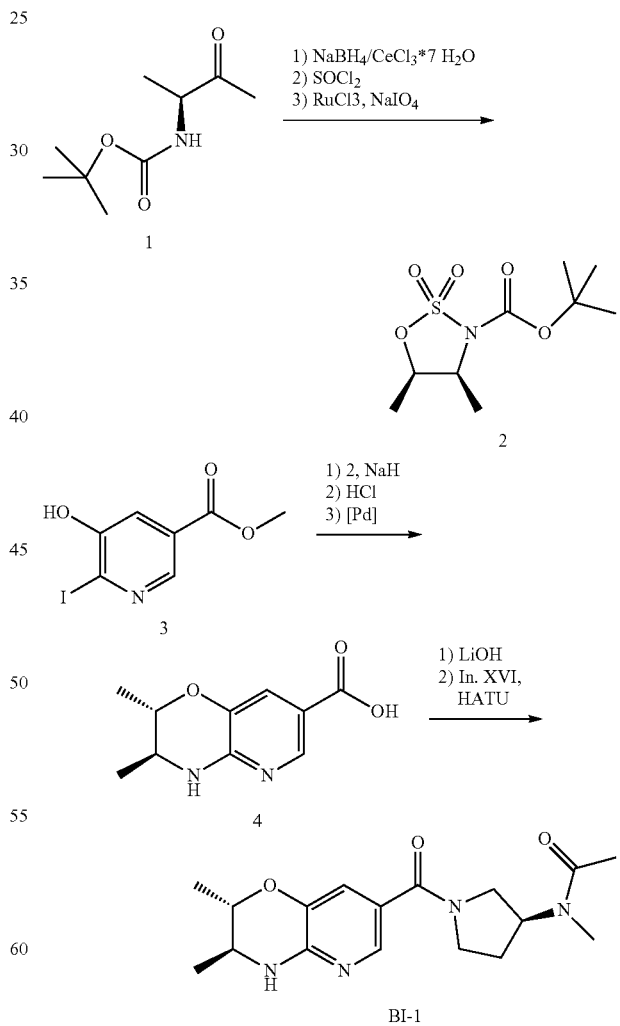

To 70 mL MeOH are added 5.40 g (28.8 mmol) ketone 1 (synthesis described in *Angew. Chem. Int. Ed.* 2010, 49, 6856) and 12.9 g (34.6 mmol) CeCl$_3$*7 H$_2$O. The reaction mixture is cooled to −15° C. before 2.18 g (57.7 mmol) NaBH₄ are added portion wise. The reaction mixture is stirred for 3 h at 0° C. The reaction is quenched by the addition of saturated aq. NH4C1 solution and extracted with EtOAc. The organic layers are combined, dried over Na₂SO₄ and the solvent is removed in vacuo.

A stirred solution of 6.29 g (52.8 mmol) thionyl chloride in 50 mL acetonitrile is cooled to the −50° C. and a solution of 4 g (21.1 mmol) in ACN of the above mentioned product is added drop wise. When addition completed then 258 mg (2.11 mmol) DMAP are added in one portion. The mixture is stirred for 15 min, keeping temperature below −40° C., and then 8.36 g (106 mmol) dry pyridine are added, keeping external temperature at −40° C. Stirring is continued for 1 h. EtOAc is added, stirred for 5 mins, suspension appeared (pyridine salt) which is filtered and washed with EtOAc. To the filtrate is added 12 mL saturated Na₂HPO₄ slowly. The resulting solution is stirred for 40 mins. Two layers are separated. The organic layer is washed with 10 mL 1M NaHSO₄ aqueous, dried over Na₂SO₄ and concentrated under reduced pressure. The crude compound is purified by column chromatography (silica gel, 8% EtOAc in hexane).

C₉H₁₇NO₄S (M=235.3 g/mol)
ESI-MS: 258 [M+Na]⁺
R$_f$ (TLC, silica gel) 0.4 (PE/EtOAc 3/1)

To a solution of 1.00 g (0.004 mol) of the above described product in 10,000 ml EtOAc are added 1.36 g (0.006 mol) NaIO4 in 10 mL H₂O Then 44 mg (0.2 mmol) RuCl₃ are added and the mixture is stirred at 0 to 15° C. for 12 h. The mixture is quenched with H₂O (20 mL) and extracted with EtOAc. Then the organic phase is washed with brine (20 mL), dried over Na₂SO₄, filtered and concentrated to dryness. The residue is purified by column chromatography (silica gel, PE/EtOAc=10:1 to 3:1).

C₉H₁₇NO₅S (M=251.3 g/mol)
ESI-MS: 252 [M+H]⁺
R$_f$ (TLC, silica gel) 0.55 (PE/EtOAc 3/1)

4.00 g (14.3 mmol) methyl 5-hydroxy-6-iodopyridine-3-carboxylate are added to 40 ml of DMF. To this are added 602 mg (15.1 mmol) sodium hydride. After gas evolution, 5.40 g (21.5 mmol) are added and the reaction mixture is stirred at 75 C for 1.5 h. After cooling down to RT, the reaction mixture is diluted with EtOAc and rinsed with water. The organics are dried, filtered, and evaporated.

The residue is purified by column chromatography (silica gel, 0-5% MeOH/CH₂Cl₂).

C₁₆H₂₃IN₂O₅ (M=450.3 g/mol)
ESI-MS: 451 [M+H]⁺

5.00 g (11.1 mmol) of the above mentioned product are added to in 50 ml of MeOH and 10 ml of CH₂C12. To this are added 50 ml of 4 M HCl in dioxane. After 3 h the volatiles are removed in vauo and the residue used without further purification.

3.28 g (9.37 mmol) of the above mentioned product, 105 mg (0.47 mmol) Pd(OAc)₂, 0.33 g (0.56 mmol), 9,9-dimethyl-4,5-bis(diphenylphosphino)xanthene (0.33 g; 0.56 mmol; 6.00 mol %) and 9.16 g (28.1 mmol) cesium carbonate are added to 100 ml dioxane and the mixture is degassed thoroughly. The reaction mixture is stirred at 90° C. under argon for 4 h. The solids are filtered through a plug of Celite® and evaporated. The residue is purified by column chromatography (silica gel, 0-5% MeOH/CH₂Cl₂).

1.50 g (6.75 mmol) of the above mentioned product are added to 5 ml of MeOH and 70 ml of water. To this are added 323 mg (13.5 mmol) LiOH and the reaction mixture is stirred at 50° C. for 1 h. The reaction is filtered and the MeOH is removed in vacuo. The aqueous layer is neutralized with 1 M HCl. The solids are filtered and allowed to dry and used without further purification.

C₁₀H₁₂N₂O₃ (M=208.2 g/mol)
ESI-MS: 209 [M+H]⁺
Rt (HPLC): 0.60 min (method A)

915 mg (4.39 mmol) of the above mentioned product are dissolved in 20 ml of DMF. To this are added 0.86 g (4.83 mmol) of intermediate XVI and 1.84 ml (13.2 mmol) TEA) followed by 1.84 g (4.83 mmol) HATU. The reaction mixture is stirred at RT for 16 h.

Volatiles are removed in vacuo and the residue is purified by column chromatography (Biotage KP-Nh cartridge, 0-10% MeOH/EtOAc).

C₁₇H₂₄N₄O₃ (M=332.4 g/mol)
ESI-MS: 333 [M+H]⁺
Rt (HPLC): 0.63 min (method A)

Other features and advantages of the present invention will become apparent from the following more detailed Examples which illustrate, by way of example, the principles of the invention.

TABLE I

Biological properties of representatives of the present invention

| Example | VNN-1 IC50 (nM) | HWB IC50 (nM) |
|---|---|---|
| 1.1 | 1.27 | 5.04 |
| 1.2 | 0.20 | 4.51 |
| 1.3 | 1.02 | 1.03 |
| 1.4 | 0.48 | 4.85 |
| 1.5 | 0.07 | 1.59 |
| 1.6 | 0.81 | 2.34 |
| 1.7 | 0.12 | |
| 1.8 | 0.12 | 1.69 |
| 1.9 | 0.12 | 1.90 |
| 1.10 | 0.14 | 1.24 |
| 1.11 | 0.15 | 1.90 |
| 1.12 | 0.16 | 6.13 |
| 1.13 | 0.17 | |
| 1.14 | 0.18 | 8.70 |
| 1.15 | 0.21 | 1.52 |
| 1.16 | 0.21 | 5.15 |
| 1.17 | 0.21 | 5.59 |
| 1.18 | 0.22 | 1.77 |
| 1.19 | 0.22 | 2.63 |
| 1.20 | 0.23 | 4.74 |
| 1.21 | 0.24 | 0.80 |
| 1.22 | 0.24 | 2.51 |
| 1.23 | 0.26 | 5.21 |
| 1.24 | 0.27 | 1.44 |
| 1.25 | 0.27 | |
| 1.26 | 0.29 | 1.98 |
| 1.27 | 0.30 | 4.39 |
| 1.28 | 0.32 | |
| 1.29 | 0.34 | |
| 1.30 | 0.40 | 3.28 |
| 1.31 | 0.44 | 2.63 |
| 1.32 | 0.46 | 2.05 |
| 1.34 | 0.47 | |
| 1.35 | 0.53 | |
| 1.36 | 0.54 | |
| 1.37 | 0.61 | 1.07 |
| 1.38 | 0.65 | 5.19 |
| 1.39 | 0.66 | |
| 1.40 | 0.67 | 2.10 |
| 1.41 | 0.77 | |
| 1.42 | 0.85 | 9.88 |
| 1.43 | 0.86 | 3.24 |
| 1.44 | 0.91 | 7.03 |
| 1.45 | 0.94 | |
| 1.46 | 0.96 | |
| 1.47 | 0.97 | 5.93 |
| 1.48 | 0.98 | |
| 1.49 | 1.04 | |

TABLE I-continued

Biological properties of representatives of the present invention

| Example | VNN-1 IC50 (nM) | HWB IC50 (nM) |
|---------|-----------------|---------------|
| 1.56 | 1.65 | |
| 1.62 | 2.36 | |
| 1.76 | 4.33 | |
| 1.81 | 6.99 | |
| 1.87 | 8.45 | |
| 1.88 | 8.83 | |
| 1.90 | 9.37 | |
| 2.1 | 0.06 | 3.57 |
| 2.2 | 0.07 | 4.49 |
| 2.3 | 0.09 | |
| 3.1 | 0.07 | 1.33 |
| 3.2 | 0.19 | 1.94 |
| 3.3 | 0.24 | 1.60 |
| 4.1 | 0.68 | 5.88 |
| 4.2 | 0.10 | 2.43 |
| 4.3 | 0.12 | 2.32 |
| 4.4 | 0.12 | 1.34 |
| 4.5 | 0.14 | 1.27 |
| 4.6 | 0.21 | |
| 4.7 | 0.22 | 3.68 |
| 5.1.A | 0.09 | 1.82 |
| 5.1.B | 0.94 | |
| 6.1.A | 0.09 | 2.59 |
| 6.1.B | 1.43 | |
| 7.1 | 0.13 | 1.78 |
| 8.1 | 0.11 | |
| 8.2 | 0.08 | 1.00 |
| 8.3 | 0.08 | 0.85 |
| 8.4 | 0.13 | 1.16 |
| 8.5 | 0.14 | 16.31 |
| 8.6 | 0.15 | 1.84 |
| 8.7 | 0.16 | 3.29 |
| 8.8 | 0.19 | 1.95 |
| 8.9 | 0.32 | 4.89 |
| 8.10 | 0.33 | 2.16 |
| 8.11 | 0.34 | 3.30 |
| 8.12 | 0.41 | 10.37 |
| 8.13 | 4.28 | |
| 8.14 | 8.56 | 76.39 |
| 9.1 | 0.39 | 2.78 |
| 9.2 | 0.15 | |
| 9.3 | 0.17 | 4.28 |
| 9.4 | 0.27 | 4.23 |
| 9.5 | 0.40 | 2.19 |
| 9.6 | 0.42 | 5.03 |
| 9.7 | 0.72 | |
| 10.1 | 0.35 | |
| 11.1 | 0.74 | |

The invention claimed is:
1. A compound of the formula I,

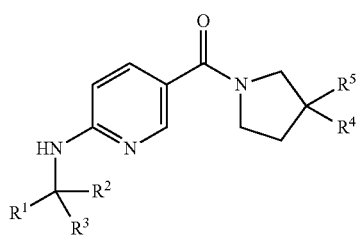

I wherein
R$^1$ is selected from the group consisting of
H,
phenyl substituted by both R$^{1.1}$ and R$^{1.3}$,
a 5-6 membered heteroaryl containing 1 to 3 heteroatoms selected from the group consisting of S, N and O and substituted by both R$^{1.2}$ and R$^{1.5}$, and
a 5-6 membered heterocyclyl containing 1 or 2 heteroatoms selected from the group consisting of S, N and O and substituted by R$^{1.4}$;
wherein
R$^{1.1}$ is selected from the group consisting of H, —CN, Br, Cl, F, C$_{1-4}$-alkyl, C$_{3-5}$-cycloalkyl, 5 membered heteroaryl optionally substituted by C$_{1-3}$-alkyl, CF$_3$, F$_3$C—CH$_2$, HF$_2$C—H$_2$N—S(O)$_2$—, H$_3$C—NH—S(O)$_2$—, (H$_3$C)$_2$N—S(O)$_2$—, H$_3$C—NH—CO—, C$_{1-4}$-alkyl-O—, H$_3$C—O—CO—, H$_2$N—, (H$_3$C)$_2$N—, H$_2$N—CO— and H$_3$C—CO—NH—;
R$^{1.2}$ is selected from the group consisting of H, —CN, Br, Cl, F, C$_{1-4}$-alkyl, C$_{3-5}$-cycloalkyl CF$_3$, F$_3$C—CH$_2$, HF$_2$C—H$_2$N—S(O)$_2$—, H$_3$C—NH—S(O)$_2$—, (H$_3$C)$_2$N—S(O)$_2$—, H$_3$C—NH—CO—, C$_{1-4}$-alkyl-O—, H$_3$C—O—CO—, H$_2$N—, (H$_3$C)$_2$N—, H$_2$N—CO— and H$_3$C—CO—NH—;
wherein in the definition of R$^{1.1}$ and R$^{1.2}$ mentioned alkyl is optionally substituted by 1-3 F-atoms
R$^{1.3}$ is selected from the group consisting of H, Cl, F, CN, C$_{1-4}$-alkyl, and C$_{1-4}$-alkyl-O—;
R$^{1.4}$ is selected from the group consisting of H, —CN, Br, Cl, F and C$_{1-4}$-alkyl optionally substituted by 1-3 F-atoms,
R$^{1.5}$ is H or C$_{1-4}$-alkyl,
R$^2$ and R$^3$ are independently from each other selected from the group consisting of H and C$_{1-3}$-alkyl,
or
R$^2$ and R$^3$ together form a 3 to 6 membered carbocycle, a 4 to 6 membered heterocycle containing 1O atom or 1N atom or a 5 to 9 membered heteroaryl containing 1-2N-atoms;
R$^4$ denotes R$^{4.1}$R$^{4.2}$N— or NC—;
R$^{4.1}$ is selected from the group consisting of C$_{1-4}$-alkyl-CO—, pyrimidinyl, and C$_{3-4}$-cycloalkyl-CO— substituted by both R$^{4.1.1}$ and R$^{4.1.2}$,
wherein
R$^{4.1.1}$ and R$^{4.1.2}$ independently from each other are selected from the group consisting of H, —CH$_3$, F, and —CN;
R$^{4.2}$ denotes H or methyl;
R$^5$ denotes H or methyl;
or a pharmaceutically acceptable salt thereof.
2. The compound according to claim 1,
wherein
R$^1$ is selected from the group consisting of H, pyrimidinyl, pyrazinyl, pyridazinyl, thiazolyl, thiophenyl, phenyl substituted by both R$^{1.1}$ and R$^{1.3}$ pyridinyl substituted by R$^{1.2}$; and pyrazolyl substituted by R$^{1.2}$ and R$^{1.5}$;
or a pharmaceutically acceptable salt thereof.
3. The compound according to claim 1,
wherein
R$^{1.1}$ is selected from the group consisting of H, —CN, Cl, F, CF$_3$, HF$_2$C—H$_2$N—S(O)$_2$—, H$_3$C—NH—S(O)$_2$—, (H$_3$C) 2N—S(O)$_2$—, H$_3$C—NH—CO—, H$_3$C—O—CO—, H$_2$N—CO—, H$_3$C—CO—NH— and 5-membered heteroaryl containing 1-3 heteroatoms selected from the group N and O optionally substituted by CF$_3$, F$_3$C—CH$_2$ or HF$_2$C—;
R$^{1.2}$ is selected from the group consisting of H, —CN, methyl, Br, Cl, F, H$_3$C—O—, CF$_3$, H$_2$N— and (H$_3$C)$_2$N—;
R$^{1.3}$ denotes H or F;
R$^{1.4}$ denotes H or F$_3$C—CH$_2$—; and
R$^{1.5}$ denotes H, methyl or butyl;
or a pharmaceutically acceptable salt thereof.

4. The compound according to claim 1, wherein R² denotes H or $C_{1\text{-}2}$-alkyl, or a pharmaceutically acceptable salt thereof.

5. The compound according to claim 1, wherein R³ denotes H or $C_{1\text{-}2}$-alkyl, or a pharmaceutically acceptable salt thereof.

6. The compound according to claim 1, wherein R² and R³ together form a $C_{3\text{-}4}$-cycloalkyl or 8 to 9 membered heteroaryl containing 1-2 N-atoms; or a pharmaceutically acceptable salt thereof.

7. The compound according to claim 1, wherein R¹ is selected from the group consisting of
H,
pyrimidinyl,
pyrazinyl,
pyridazinyl,
thiazolyl,
thiophenyl,
phenyl substituted by $R^{1.1}$ and $R^{1.3}$
pyridinyl substituted by $R^{1.2}$,
5-6 membered heterocyclyl containing 1 or 2 heteroatoms selected from the group consisting of S, N and O and substituted by $R^{1.4}$, and pyrazolyl substituted by $R^{1.5}$;
wherein
$R^{1.1}$ is selected from the group consisting of H, —CN, Cl, F, $CF_3$, $HF_2C$—, $H_2N$—$S(O)_2$—, $H_3C$—NH—$S(O)_2$—, $(H_3C)_2N$—$S(O)_2$—, $H_3C$—NH—CO—, $H_3C$—O—CO—, $H_2N$—CO—, $H_3C$—CO—NH—, and oxadiazolyl optionally substituted by $CF_3$, $F_3C$—$CH_2$ and $HF_2C$—;
$R^{1.2}$ is selected from the group consisting of H, —CN, methyl, Br, Cl, F, $H_3C$—O—, $CF_3$, $H_2N$— and $(H_3C)_2N$—;
$R^{1.3}$ denotes H or F;
$R^{1.4}$ denotes H or $F_3C$—$CH_2$—;
$R^{1.5}$ denotes H, methyl or butyl;
R² and R³ are independently from each other selected from the group consisting of H and $C_{1\text{-}2}$-alkyl, or
R² and R³ together form a $C_{3\text{-}4}$-cycloalkyl or a 8 to 9 membered heteroaryl containing 1-2N-atoms;
R⁴ denotes $R^{4.1}R^{4.2}N$— or NC—;
or a pharmaceutically acceptable salt thereof.

8. A compound selected from the group consisting of examples 1.11, 1.28, 1.44, 2.2, 2.3, 3.2, 4.1, 4.3, 7.1, 9.3, 9.4 and 9.6, Ex. 1.11

Ex. 1.28

Ex. 1.44

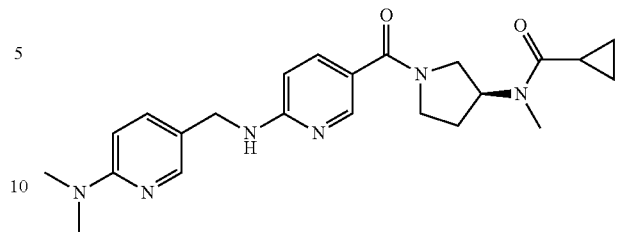

Ex. 2.2

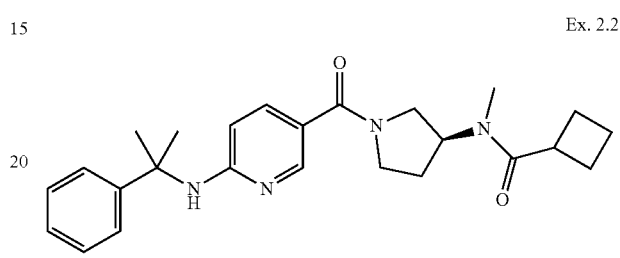

Ex. 2.3

Ex. 3.2

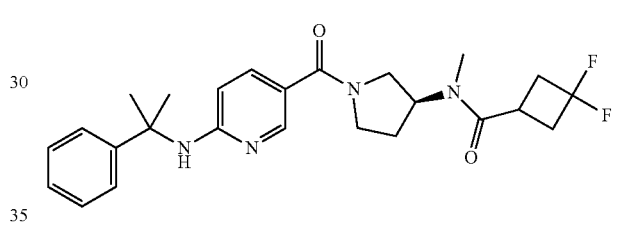

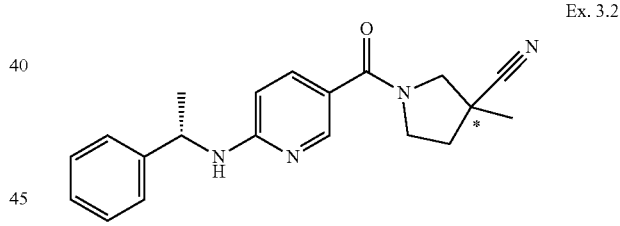

Ex. 4.1

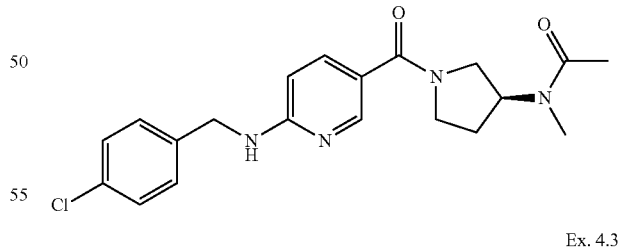

Ex. 4.3

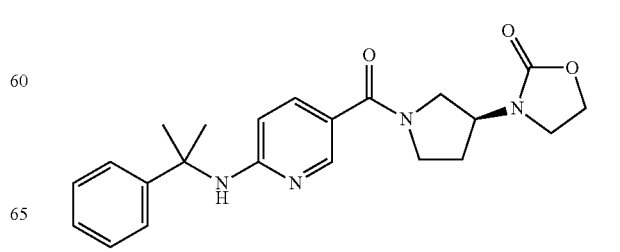

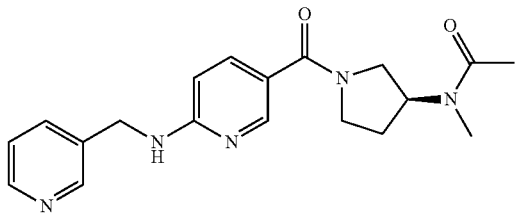

Ex. 7.1

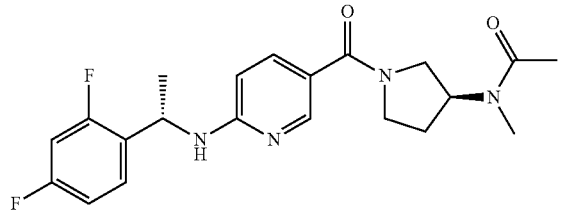

Ex. 9.6

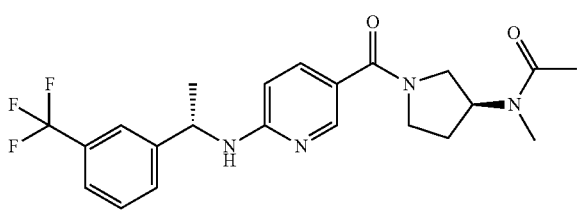

Ex. 9.3

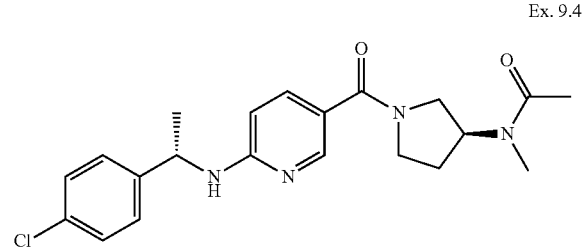

Ex. 9.4 wherein * denotes stereochemistry at the chiral center of the enantiomerically and diastereomerically pure compound was not determined, or a pharmaceutically acceptable salt thereof.

9. A pharmaceutical composition comprising a therapeutically effective amount of at least one compound of formula I according to claim 1 or a pharmaceutically acceptable salt thereof and one or more pharmaceutically acceptable excipients.

10. A method of treating a patient suffering from Crohn's disease, ulcerative colitis, atopic dermatitis, systemic sclerosis, Non-Alcoholic Steatohepathitis (NASH), psoriasis, chronic kidney disease, chronic obstructive pulmonary disease, idiopathic pulmonary fibrosis, rheumatoid arthritis, scleroderma, asthma, allergic rhinitis, allergic eczema, juvenile rheumatoid arthritis, juvenile idiopathic arthritis, graft versus host disease, psoriatic arthritis, Hyperlipidemia, colorectal cancer or pancreatic cancer related new onset diabetes, the method comprising administering to the patient a therapeutically effective amount of the compound according to claim 1.

11. A pharmaceutical composition comprising a compound of formula I according to claim 1, and additionally a pharmaceutically active compound selected from the group consisting of an immunomodulatory agent, anti-inflammatory agent or a chemotherapeutic agent.

* * * * *